(12) United States Patent
Chand et al.

(10) Patent No.: US 7,045,535 B2
(45) Date of Patent: May 16, 2006

(54) COMPOUNDS USEFUL FOR INHIBITING PARAMYXOVIRUS NEURAMINIDASE

(75) Inventors: Pooran Chand, Birmingham, AL (US); Yarlagadda S. Babu, Birmingham, AL (US); R. Scott Rowland, Hoover, AL (US); Tsu-Hsing Lin, Vestavia Hills, AL (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 17 days.

(21) Appl. No.: 10/275,763

(22) PCT Filed: Mar. 8, 2002

(86) PCT No.: PCT/US02/07052

§ 371 (c)(1),
(2), (4) Date: Nov. 8, 2002

(87) PCT Pub. No.: WO02/076971

PCT Pub. Date: Oct. 3, 2002

(65) Prior Publication Data

US 2003/0187063 A1 Oct. 2, 2003

Related U.S. Application Data

(60) Provisional application No. 60/273,952, filed on Mar. 8, 2001.

(51) Int. Cl.
*C07D 315/00* (2006.01)
*A01N 46/16* (2006.01)
*A61K 31/35* (2006.01)

(52) U.S. Cl. .................. 514/326; 514/359; 514/369; 514/370; 514/380; 514/397; 514/422; 514/444; 514/445; 514/459; 514/460; 546/207; 548/185; 548/243; 548/255; 548/311.1; 548/517; 549/60; 549/414; 549/419; 549/424

(58) Field of Classification Search ............ 514/326, 514/359, 369, 370, 380, 397, 422, 444, 445, 514/459, 460; 546/207; 548/185, 243, 255, 548/311.1, 517; 549/60, 414, 419, 424

See application file for complete search history.

(56) References Cited

PUBLICATIONS

Database CAPLUS on STN, Acc. No. 1984:22353, EP 81699 (Jun. 22, 1983) (abstract).*
Database CAPLUS on STN, Acc. No. 1952:51859, Ipatieff et al., Bulletin de la Societe Chimique de France (1951) p. 259–68 (abstract).*

* cited by examiner

*Primary Examiner*—Brian Davis
(74) *Attorney, Agent, or Firm*—Connolly, Bove, Lodge & Hutz, LLP

(57) ABSTRACT

Certain cyclic compounds are presented as well as their use for inhibiting paramyxovirus neuraminidase. The compounds are represented by the following formulas:

A

B

C

14 Claims, 22 Drawing Sheets

Scheme 4

Scheme 8

Scheme 9

Scheme 10

Scheme 12

P = protecting group

Scheme 17

Scheme 18

Scheme 19

Scheme 23

R may be $CH_2OH$, $CH_2N_3$, $CH_2NH_2$, $CH_2NHCOalkyl/aryl/arylalkyl$, or $CH_2NH\text{-}SO_2alkyl/aryl/arylalkyl$

US 7,045,535 B2

COMPOUNDS USEFUL FOR INHIBITING PARAMYXOVIRUS NEURAMINIDASE

TECHNICAL FIELD

The present invention relates to new compounds that are useful as inhibitors of paramyxovirus neuraminidase and pharmaceutical compositions containing the compounds. The represent invention also relates to a method of treating paramyxovirus infection and inhibiting paramyxovirus neuraminidase by administering a compound of the present invention.

BACKGROUND OF THE INVENTION

Viruses of the family Paramyxoviridae are enveloped negative-stranded RNA viruses which comprise two subfamilies, paramyxovirinae and Pneumoriniae. The subfamily Pararmyxovirinae includes Human Parainfluenza Viruses types 1, 2, 3 and 4, Mumps Virus, Newcastle Disease Virus, and Measles Virus. Human Respiratory Syncytial virus is a member of the subfamily Pneumovirinae.

As a group, these viruses are a leading cause of respiratory disease in humans, especially children. These paramyxoviruses are the causative agents of such respiratory diseases as croup, bronchitis, and pneumonia. Taken together the various stains of paramyxovirus are responsible for annual epidemics in humans. Re-infection in following years is common but less severe (Kass, ed., studies in *Infectious Diseases Research*, The University of Chicago Press, Chicago (1975), pp. 51–64). Although some immunity develops through infection by the various strains of paramyxoviruses it is not sufficient to provide complete protection. The vaccines that have been developed have been shown to have only limited efficacy in the short term so that long term usage is completely ineffective (Choppin and Schneid, *Rev. Infect, Dis* 2:40–61 (1980); Norrby et al., *J. Infect Dis.* 132:262–269 (1975). The lack of an effective vaccine together with the epidemiological evidence of the occurrence of annual epidemics of paramyxovirus infection indicates the urgent need for the development of therapeutic agents.

SUMMARY OF THE INVENTION

The present invention relates to novel compounds useful as therapeutic agents for paramyxovirus infection. In particular, compounds of the present invention are represented by the formula:

A

B

C wherein X is selected from the group consisting of:
CHR, O, NR, N—OR, NR(O), S, S(O) and S(O)O
$X_1$ is selected from the group consisting of CR, N, and N(O);
R is selected from the group consisting of:
H, alkyl, alkene, alkyne, CN, $NO_2$, $N_3$, halo and $NHR_{10}$;
$R_1$ is selected from the group consisting of:
H, $(CH_2)nCO_2R_{10}$, $(CH_2)$n-tetrazol, $(CH_2)nSO_3H$, $(CH_2)nSO_2H$, $(CH_2)nPO_3H_2$, $(CH_2)nCONR_{10}$, $(CH_2)nNO_2$, and $(CH_2)nCHO$;
$R_{1a}$ is selected from the group consisting of:
H, $(CH_2)nOR_{10}$, $(CH_2)nCN$, $(CH_2)nNR_{10}R_{10a}$, $(CH_2)nNHC(O)R_{10}$, $(CH_2)nC(O)NR_{10}R_{10a}$, and $(CH_2)nOC(O)R_{10}$;
$R_1$ and $R_{1a}$ both cannot be H each of $R_2$ and $R_{2a}$ is independently selected from the group consisting of H, halo, CN, $(CH_2)nCO_2R_{10}$, $(CH_2)nNR_{10}R_{10a}$ and $(CH_2)_n—OR_{10}$;
each of $R_3$ and $R_{3a}$ is independently selected from the group consisting of:
H, $NHSO_2R_{10}$, $N(O)—SO_2R_{10}$, $NR_{10}SO_2R_{10a}$, $(CH_2)mYR_{10}$, and $(CH_2)mR_6$;
at least one of $R_3$ and $R_{3a}$ is other than H
Y is selected from the group consisting of:
O, NH, NHC(O), C(O)NH, S, S(O), S(O)O, NHS(O)O, S(O)ONH, NHC(O)NH and heterocycle;
$R_3$ and $R_{3a}$ together may be
=O, =$CHR_6$, =$CHR_{10}$, =$NR_{10}$, and =N—$OR_{10}$
$R_4$ and $R_{4a}$ is independently selected from the group consisting of:
H, $(CH_2)mYR_{10}$, and $(CH_2)mR_6$
$R_4$ and $R_{4a}$ together may be:
=O, =$CHR_6$, =$CHR_{10}$, =$NR_{10}$ and =N—$OR_{10}$
each of $R_5$ and $R_{5a}$ is independently selected from the group consisting of $C(R_7)(R_{7a})$, $C(R_7)(R_{7a})C(R_8)(R_{8a})$, $C(R_7)(R_{7a})C(R_8)(R_{8a})C(R_9)(R_{9a})$, $OC(R_7)(R_{7a})$, $OC(R_7)(R_{7a})C(R_8)(R_{8a})$, $C(R_7)(R_{7a})OC(R_8)(R_{8a})$, $N(R_{10})C(R_7)(R_{7a})$, $N(R_{10})$ $C(R_7)(R_{7a})C(R_8)(R_{8a})$, $C(R_7)(R_{7a})N(R_{10})C(R_8)(R_{8a})$, and $C(O)NR_{10}R_{10a}$;
$R_6$ is selected from the group consisting of
H, halo, CN, $NO_2$, $N_3$, $CO_2R_{10}$, $R_{10}$ and $NR_{10}R_{10a}$;
$R_7$, $R_{7a}$, $R_8$, $R_{8a}$, $R_9$ and $R_{9a}$ is selected from the group from the group consisting of:
H, $(CH_2)mYR_{10}$ and $(CH_2)mR_6$
each of the $R_{10}$ and $R_{10a}$ is individually selected from the groups consisting of:
H, alkyl, substituted alkyl, aryl, substituted aryl, arylalkyl, substituted arylalkyl, heterocycle, substituted heterocycle, alkenyl, substituted alkenyl, alkynyl, and substituted alkynyl;
Each of m and n is individually 0, 1, 2, 3, or 4, and when $R_3$ or $R_{3a}$ is $(CH_2)Y_mR_{10}$ or $(CH_2)_mR_6$, m is preferably at least 1 for the $R_3$ or $R_{3a}$ moiety;
and pharmaceutically acceptable salt thereof; and prodrugs thereof.

The present invention also relates to pharmaceutical compositions for inhibiting paramyxovirus neuraminidase, which comprises a pharmaceutically acceptable carrier and an amount effective for inhibiting paramyxovirus neuraminidase of at least one of the above-disclosed compounds.

Another aspect of the present invention relates to inhibiting paramyxovirus neuraminidase which comprises administering to a patient in need thereof a composition comprising a pharmaceutically acceptable carrier and an amount effective for inhibiting neuraminidase of at least one of the above-disclosed compounds.

A still aspect of the present invention relates to treating paramyxovirus infection which comprises administering to a patient in need thereof a composition comprising a pharmaceutically acceptable carrier and an amount effective for inhibiting influenza virus neuraminidase of at least one of the above-disclosed compounds.

BEST AND VARIOUS MODES FOR CARRYING OUT INVENTION

Figure 1:
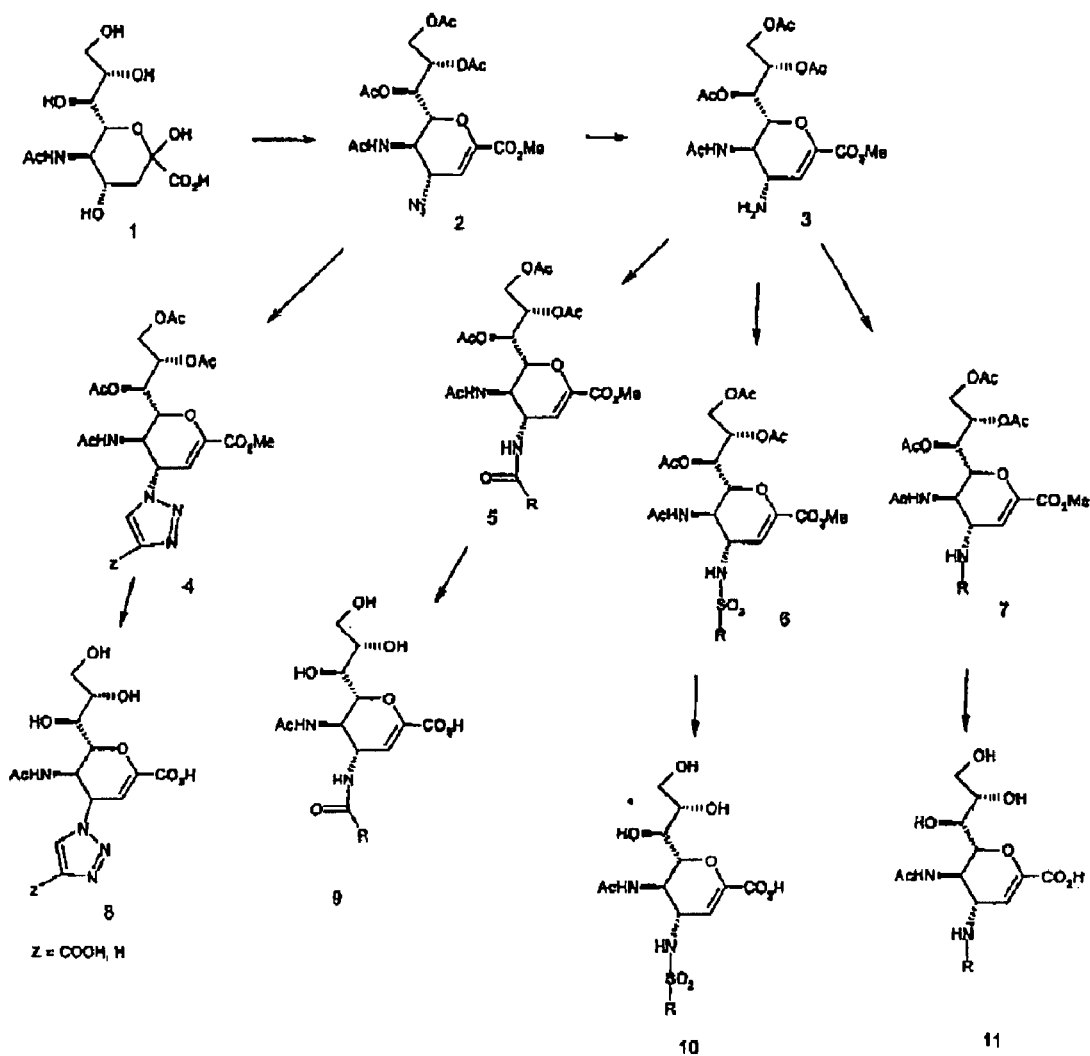
FIGS. 1–23 illustrate various methods for preparing compounds of the present invention.

Compounds of the present invention are presented by the following formulas:

A

B

C wherein X is selected from the group consisting of:
CHR, O,NR, N—OR, NR(O), S, S(O) and S(O)O
$X_1$ is selected from the group consisting of CR, N, and N(O);
R is selected from the group consisting of:
H, alkyl, alkene, alkyne, CN, $NO_2$, $N_3$, halo and $NHR_{10}$;
$R_1$ is selected from the group consisting of:
H, $(CH_2)nCO_2R_{10}$, $(CH_2)$n-tetrazol, $(CH_2)nSO_3H$, $(CH_2)nSO_2H$, $(CH_2)nPO_3H_2$, $(CH_2)nCONR_{10}$, $(CH_2)nNO_2$, and $(CH_2)nCHO$;
$R_{1a}$ is selected from the group consisting of:
H, $(CH_2)nOR_{10}$, $(CH_2)nCN$, $(CH_2)nNR_{10}R_{10a}$, $(CH_2)nNHC(O)R_{10}$, $(CH_2)nC(O)NR_{10}R_{10a}$, and $(CH_2)nOC(O)R_{10}$;
$R_1$ and $R_{1a}$ both cannot be H
each of $R_2$ and $R_{2a}$ is independently selected from the group consisting of H, halo, CN, $(CH_2)nCO_2R_{10}$, $(CH_2)nNR_{10}R_{10a}$ and $(CH_2)_n$—$OR_{10}$;
each of $R_3$ and $R_{3a}$ is independently selected from the group consisting of:
H, $NHSO_2R_{10}$, $N(O)$—$SO_2R_{10}$, $NR_{10}SO_2R_{10a}$, $(CH_2)mYR_{10}$, and $(CH_2)mR_6$;
at least one of $R_3$ and $R_{3a}$ is other than H
Y is selected from the group consisting of:
O, NH, NHC(O), C(O)NH, S, S(O), S(O)O, NHS(O)O, S(O)ONH, NHC(O)NH and heterocycle;
$R_3$ and $R_{3a}$ together may be
=O, =$CHR_6$, =$CHR_{10}$, =$NR_{10}$, and =N—$OR_{10}$
$R_4$ and $R_{4a}$ is independently selected from the group consisting of:
H, $(CH_2)mYR_{10}$, $(CH_2)mR_6$
$R_4$ and $R_{4a}$ together may be:
=O, =$CHR_6$, =$CHR_{10}$, =$NR_{10}$, and =N—$OR_{10}$
each of $R_5$ and $R_{5a}$ is independently selected from the group consisting of
$C(R_7)(R_{7a})$, $C(R_7)(R_{7a})C(R_8)(R_{8a})$, $C(R_7)(R_{7a})C(R_8)(R_{8a})$ $C(R_9)(R_{9a})$, $OC(R_7)(R_{7a})$, $OC(R_7)(R_{7a})C(R_8)(R_{8a})$, $C(R_7)(R_{7a})OC(R_8)(R_{8a})$, $N(R_{10})C(R_7)(R_{7a})$, $N(R_{10})C(R_7)(R_{7a})C(R_8)(R_{8a})$, $C(R_7)(R_{7a})N(R_{10})C(R_8)(R_{8a})$, and $C(O)NR_{10}R_{10a}$;
$R_6$ is selected from the group consisting of
H, halo, CN, $NO_2$, $N_3$, $CO_2R_{10}$, $R_{10}$ and $NR_{10}R_{10a}$;
$R_7$, $R_{7a}$, $R_8$, $R_{8a}$, $R_9$ and $R_{9a}$ is selected from the group from the group consisting of:
H, $(CH_2)mYR_{10}$ and $(CH_2)mR_6$
each of the $R_{10}$ and $R_{10a}$ is individually selected from the groups consisting of:
H, alkyl, substituted alkyl, aryl, substituted aryl, arylalkyl, substituted arylalkyl, heterocycle, substituted heterocycle, alkenyl, substituted alkenyl, alkynyl, and substituted alkynyl;
Each of m and n is individually 0, 1, 2, 3, or 4, and when $R_3$ or $R_{3a}$ is $(CH_2)_mYR_{10}$ or $(CH_2)_mR_6$ than m is preferably, but not necessarily, at least 1 for the $R_3$ or $R_{3a}$ moiety;
and pharmaceutically acceptable salt thereof; and prodrugs thereof.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 12 carbon atoms. The expression "lower alkyl" refers to unsubstituted alkyl groups of 1 to 4 carbon atoms.

The terms "substituted alkyl", "substituted alkenyl" or "substituted alkynyl" refer to an alkyl, alkenyl or alkynyl group substituted by, for example, one to four substituents, such as halo, trifluoromethyl, trifluoromethoxy, hydroxy, alkoxy, cycloalkyloxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, (arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as indolyl, imidazolyl, furyl, thienyl, thiazolyl, pyrrolidinyl, pyridyl, pyrimidyl and the like. Where noted above where the substituent is further substituted it will be with halogen, alkyl, alkoxyaryl or aralkyl. Preferred substitutions are halo, $SO_3H$, $CO_2H$, $NHR_{10}$, and $SO_2R_{10}$.

The term "halogens" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" or "alkylaryl" refers to an aryl group bonded directly through an alkyl group, such as benzyl or phenethyl.

The term "substituted aryl" or "substituted alkylaryl" refers to an aryl group or alkylaryl group substituted by, for example, one to four substituents such as alkyl, substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl. "Substituted benzyl" refers to a benzyl group substituted by, for example, any of the groups listed above for substituted aryl.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1, 1-dioxothienyl, dioxanyl, isothiazolidinyl, thietanyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl, or furo[2,3-b] pyridinyl), dihydroisoindolyl, diyhdroquinazolinyl (such as 3,4-dihydro-4-oxo-quinazolinyl), benzisothiazolyl, benzisoxazolyl, benzodiazinyl, benzofurazanyl, benzothiopyranyl, benzothiazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents.

The term "heteroatoms" shall include oxygen, sulfur and nitrogen.

Within the above-described definitions, certain embodiments are preferred. Preferred alkyl groups are lower alkyl groups containing 1 to 12 carbon, and more preferably 1 to about 5 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. An example of a suitable alkylaryl group is phenethyl. Examples of suitable cycloalkyl groups typically contain 3–8 carbon atoms and include cyclopropyl, cyclobutyl, cyclopentyl and cyclohexyl. The aromatic or aryl groups are preferably phenyl or alkyl substituted aromatic groups (aralkyl) such as phenyl $C_{1-3}$ alkyl such as benzyl.

The N-heterocyclic rings preferably contain 3–7 atoms in the ring and a heteroatom such as N, S or O in the ring. Examples of suitable preferred heterocyclic groups are pyrrolidino, azetidino, piperidino, 3,4-didehydropiperidino, 2-methylpiperidino and 2-ethylpiperidino. In addition, the above substitutions can include halo such as F, Cl, Br, lower alkyl, lower alkoxy and halo substituted lower alkoxy.

Pharmaceutically acceptable salts of the compounds of formula (I) include those identified from pharmaceutically acceptable, inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic, trifluoroacetic and benzenesulphonic acids.

Salts derived from appropriate bases include alkali such as sodium and ammonia.

It is of course understood that the compounds of the present invention relate to all optical isomers and stereo-isomers at the various possible atoms of the molecule.

Figure 2:
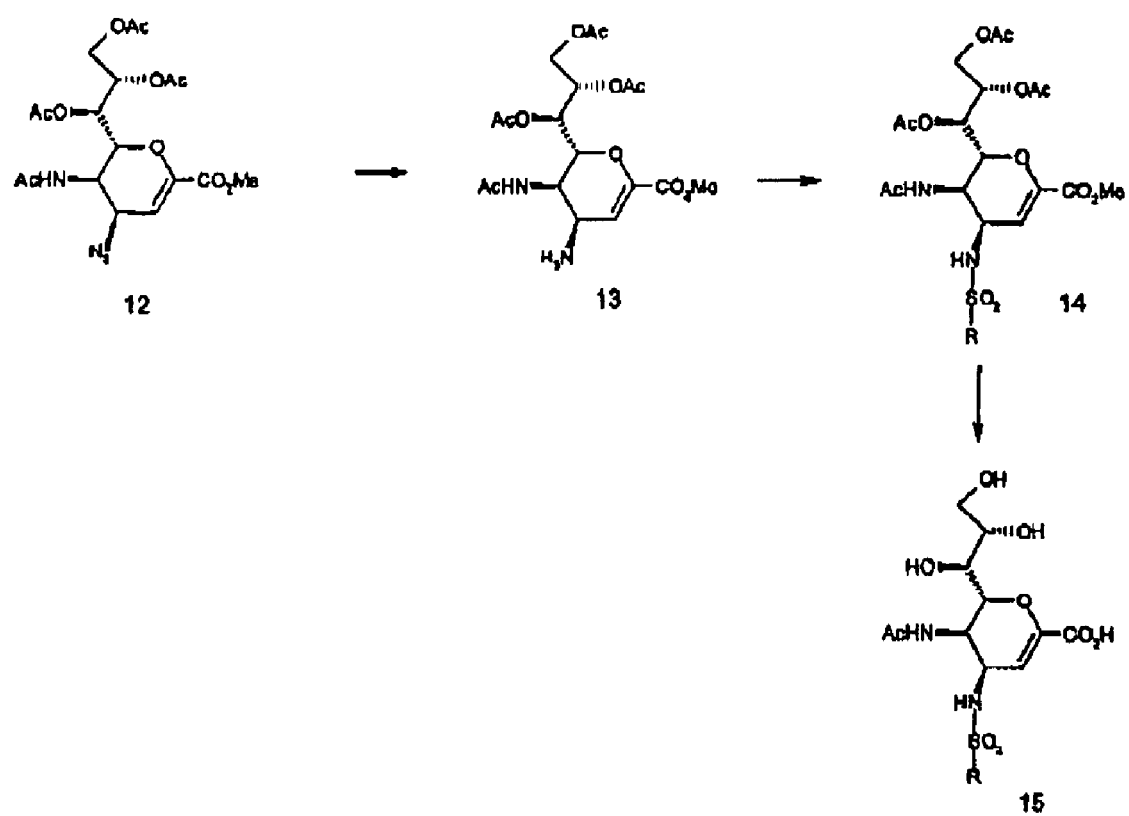
Figure 3:
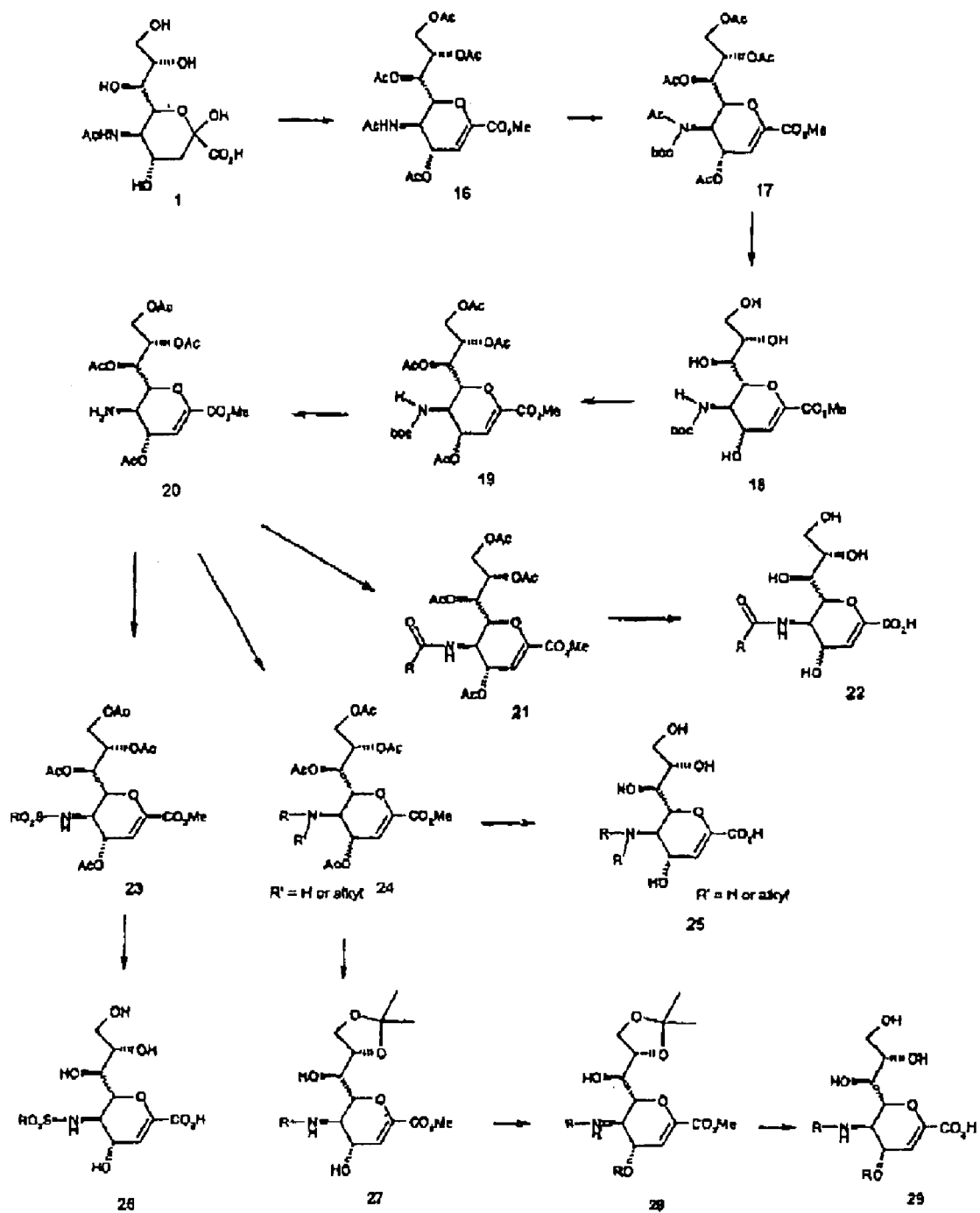
Figure 4:
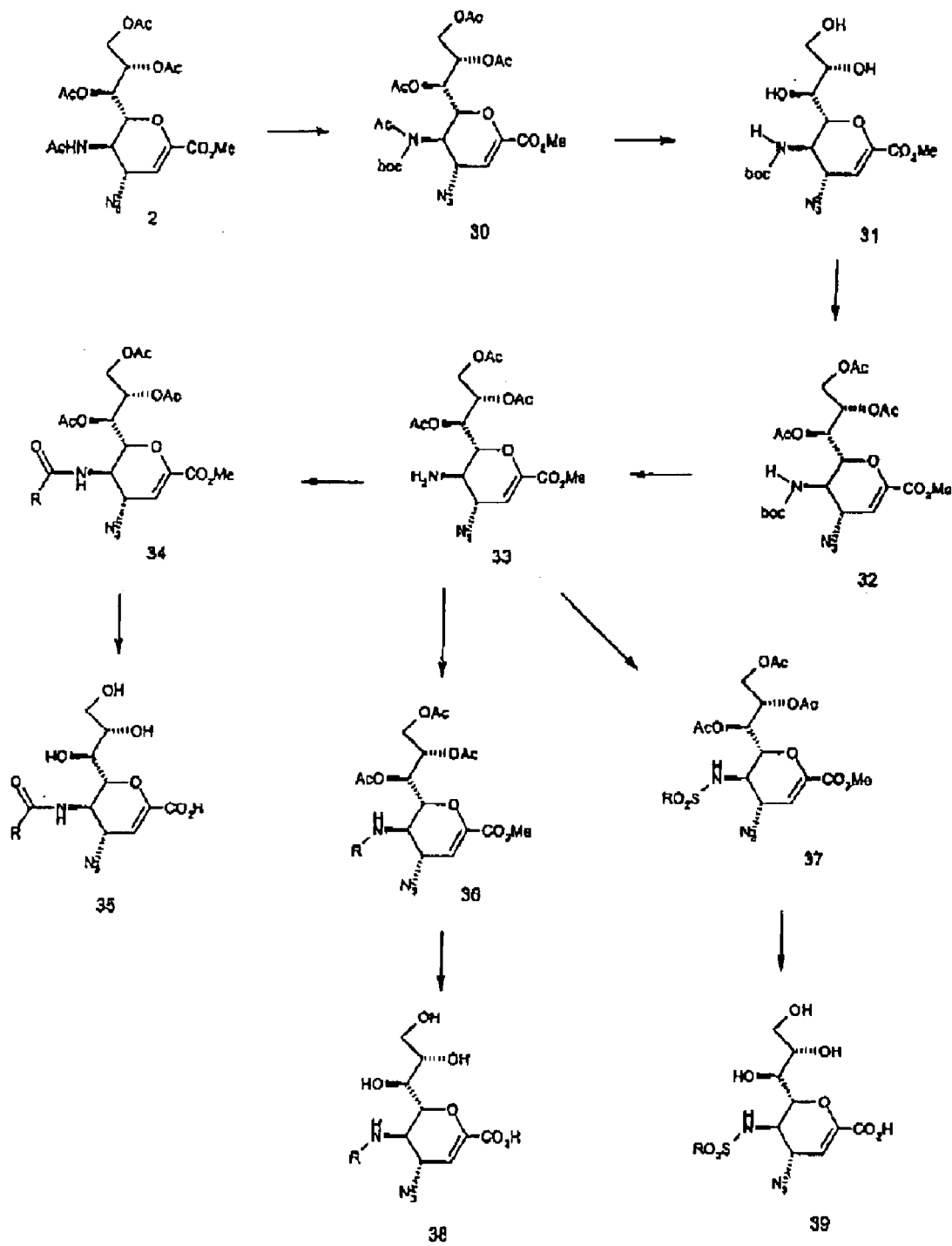
Figure 5:
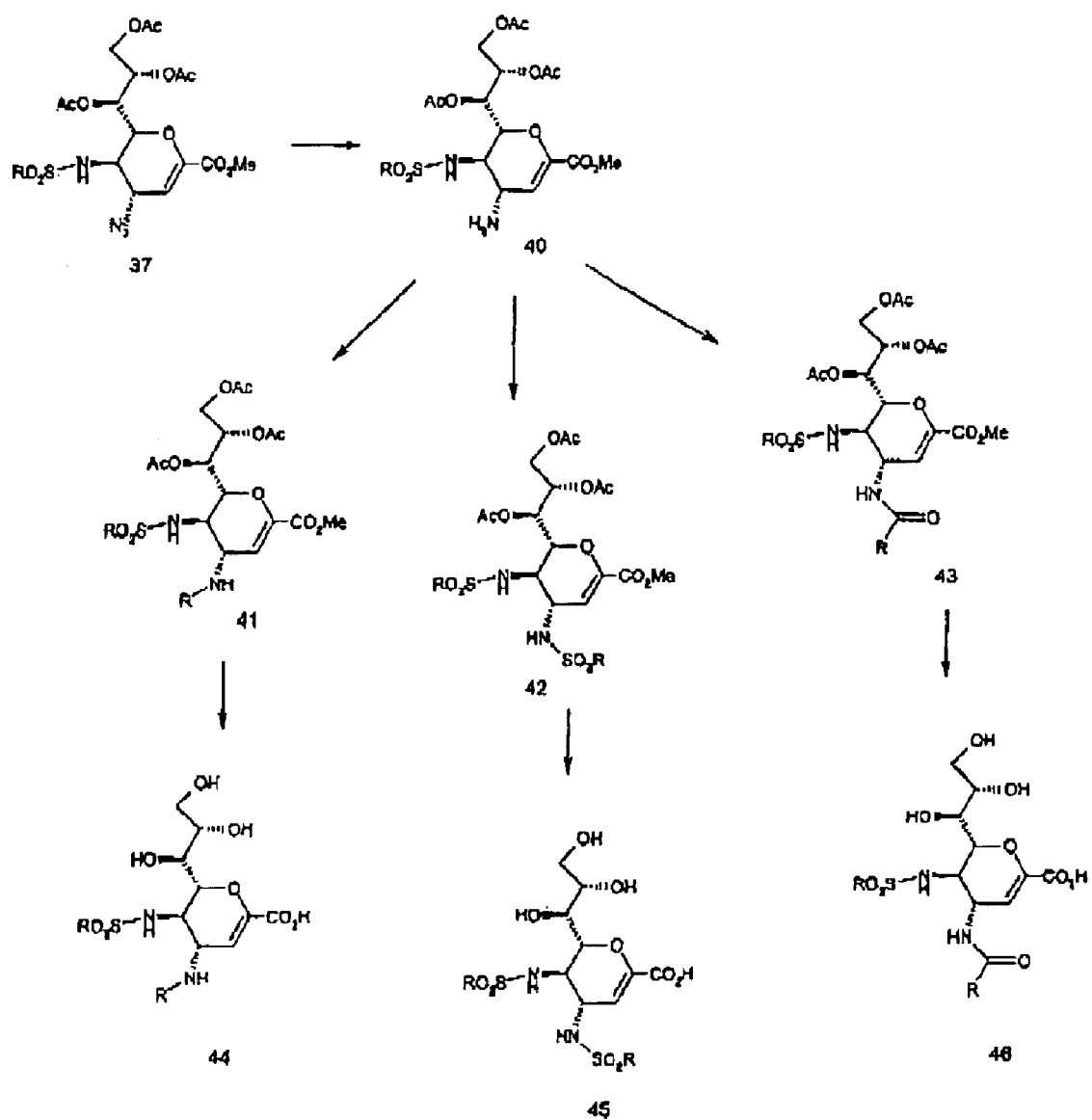
Figure 6:
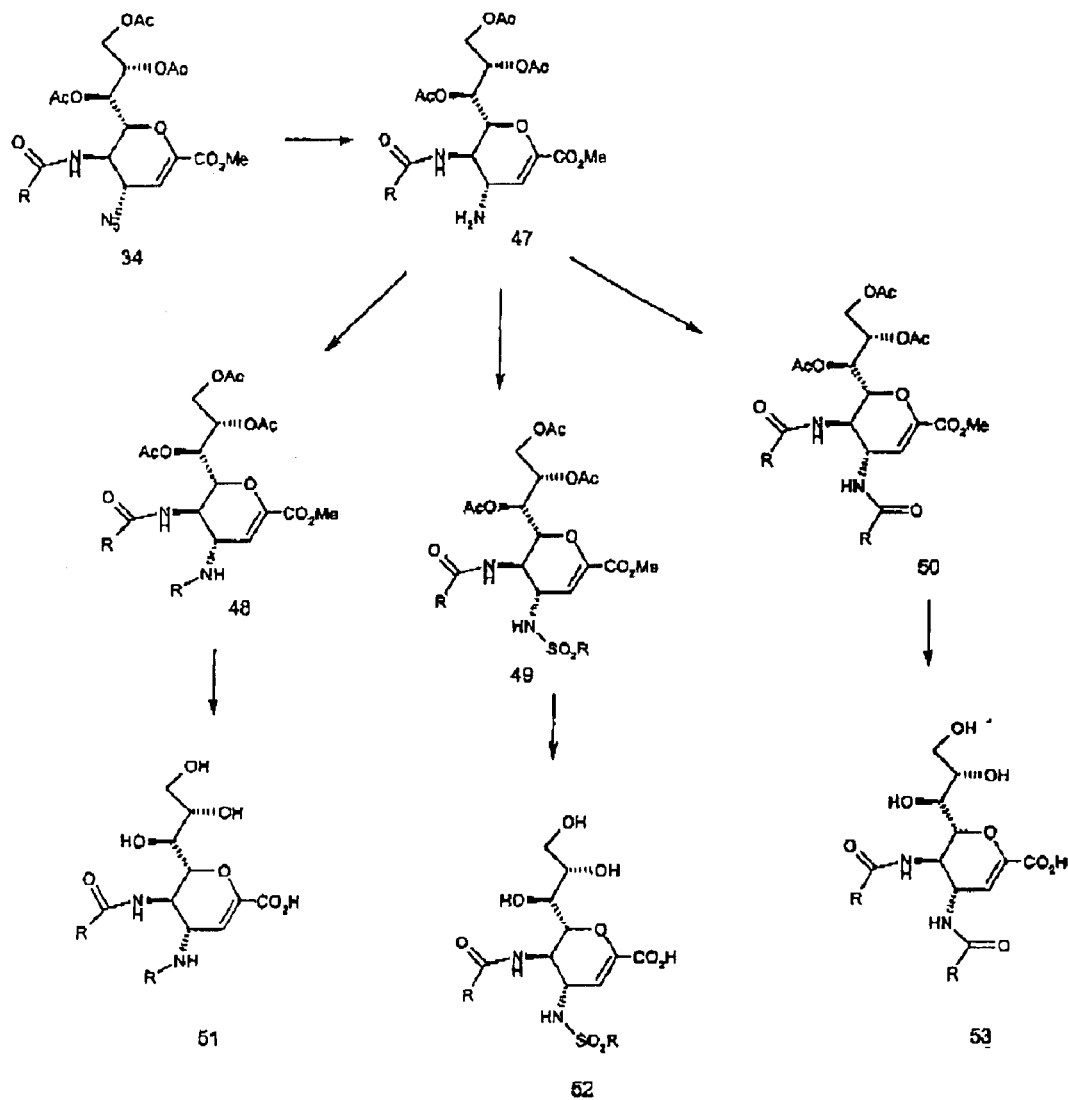
Figure 7:
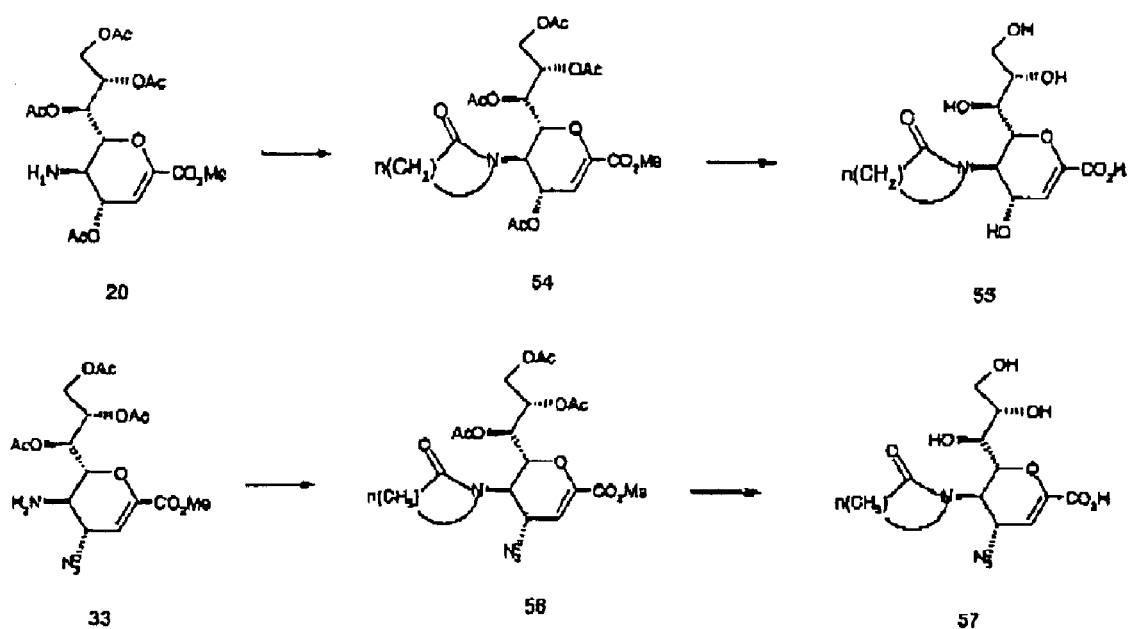
Figure 8:
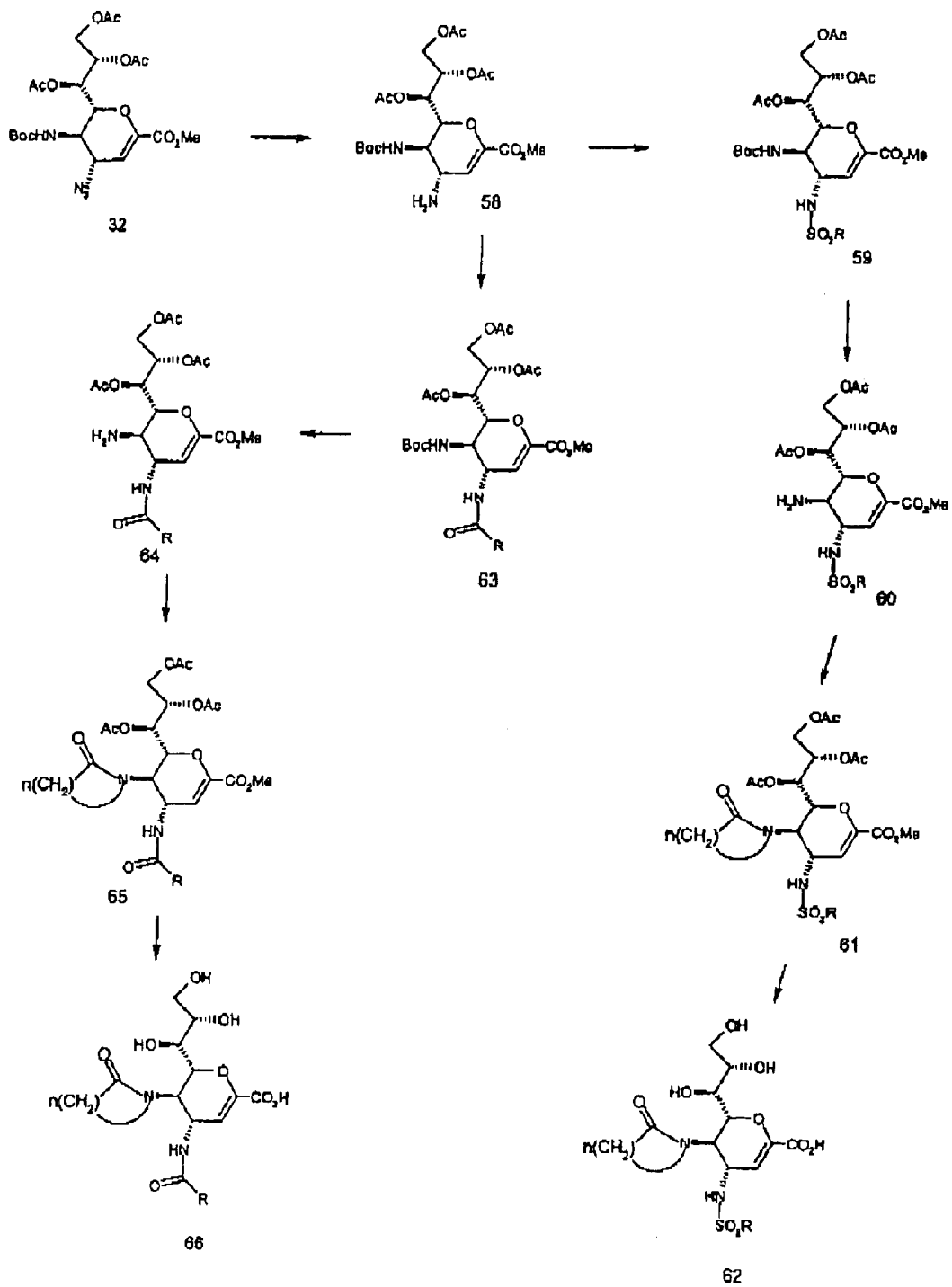
Figure 9:
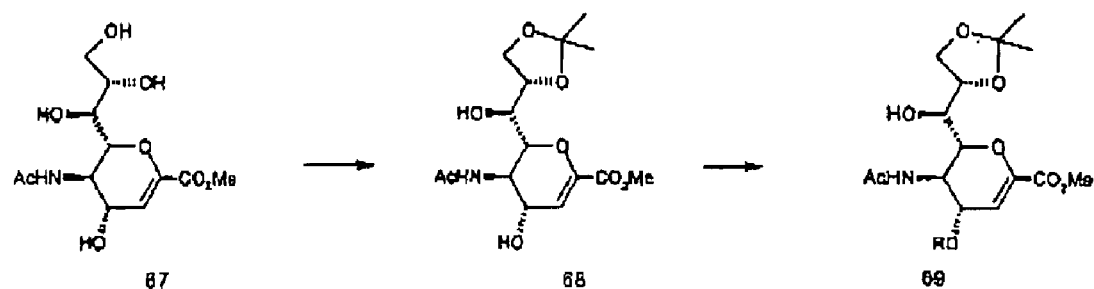
Figure 9:
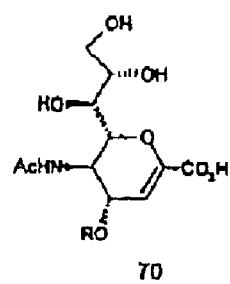
Figure 10:
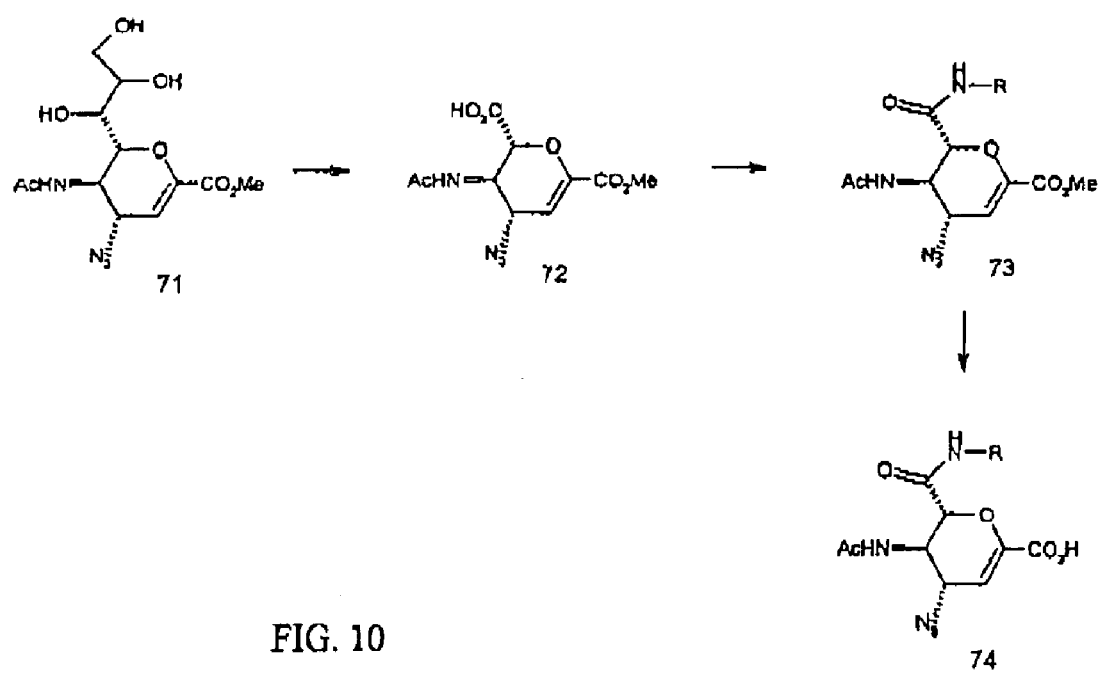
Figure 11:
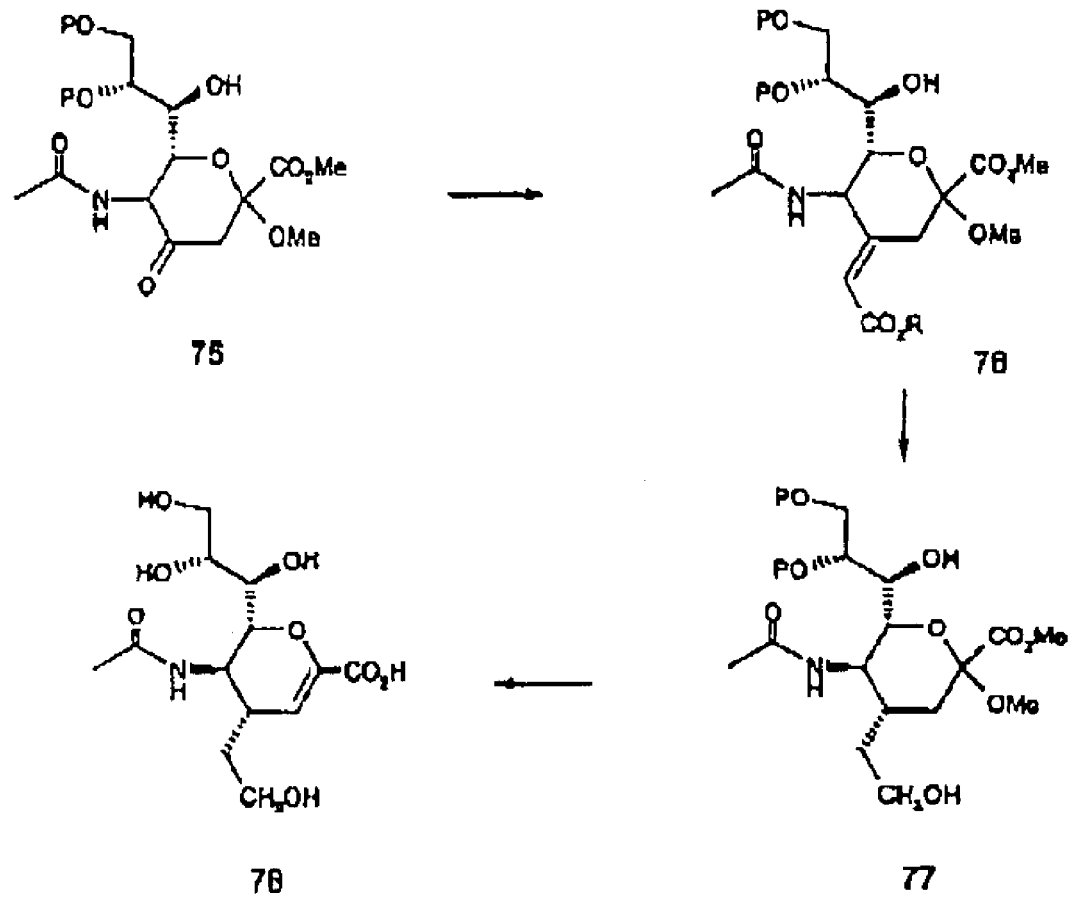
Figure 12:
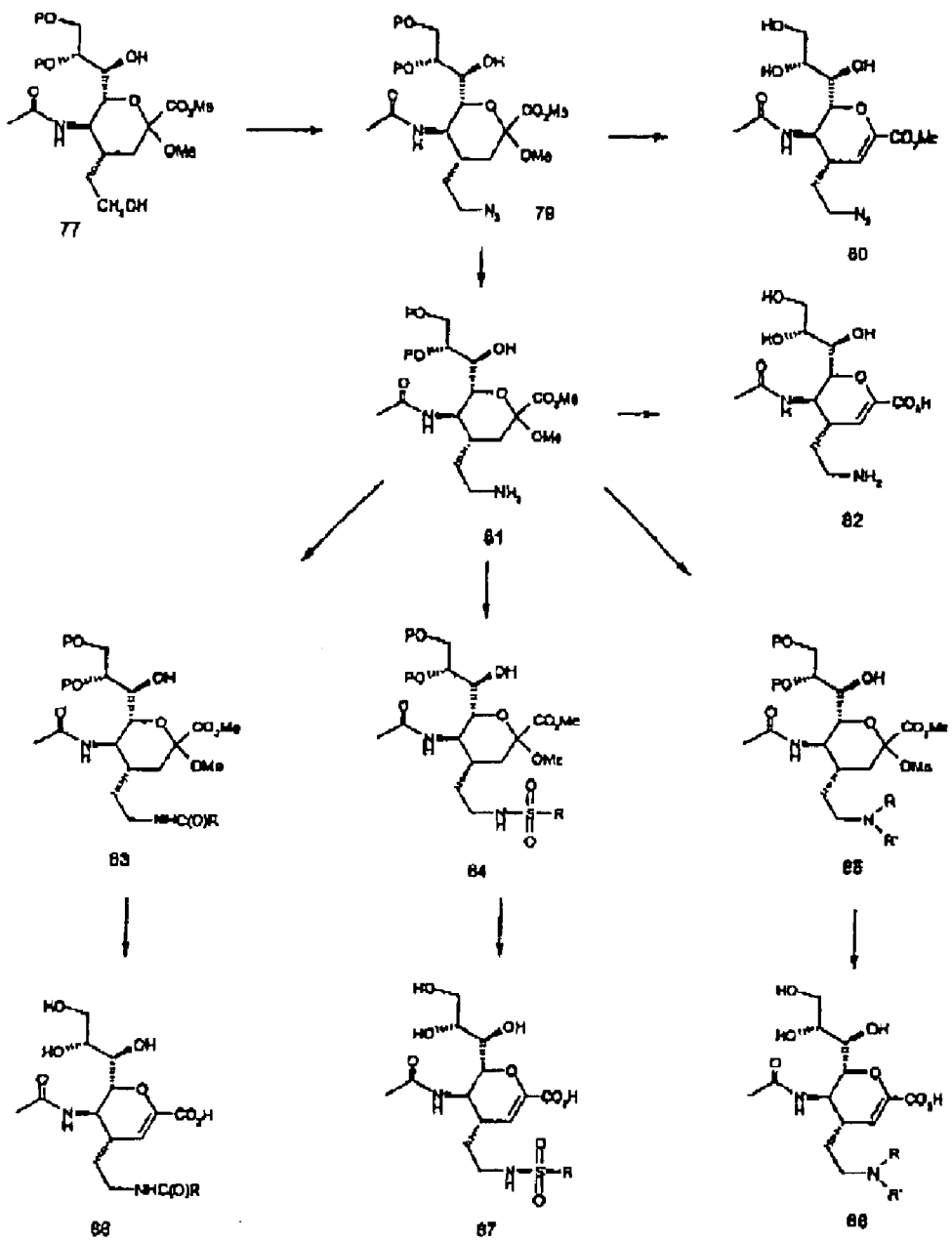
Figure 13:
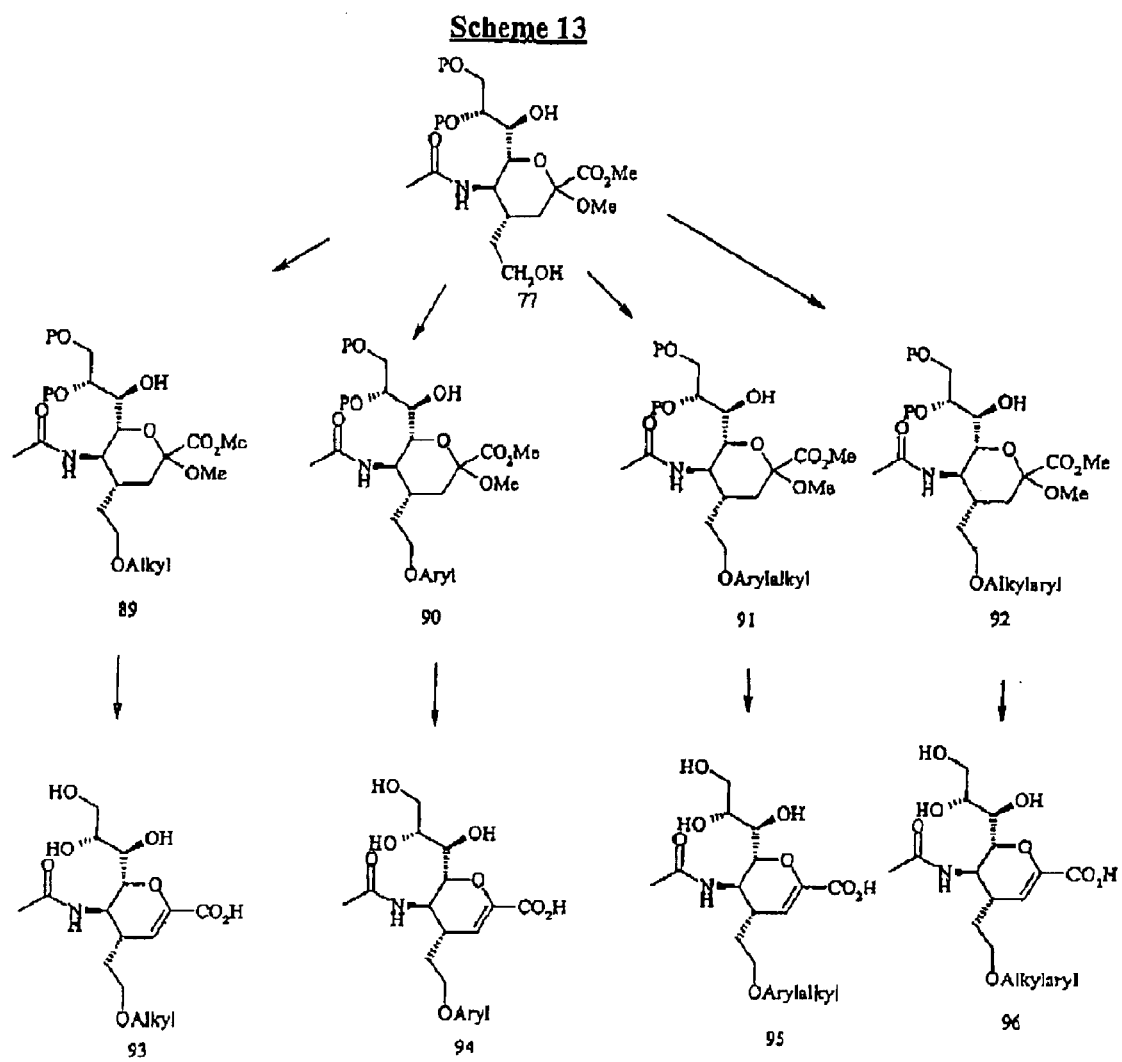
Figure 14:
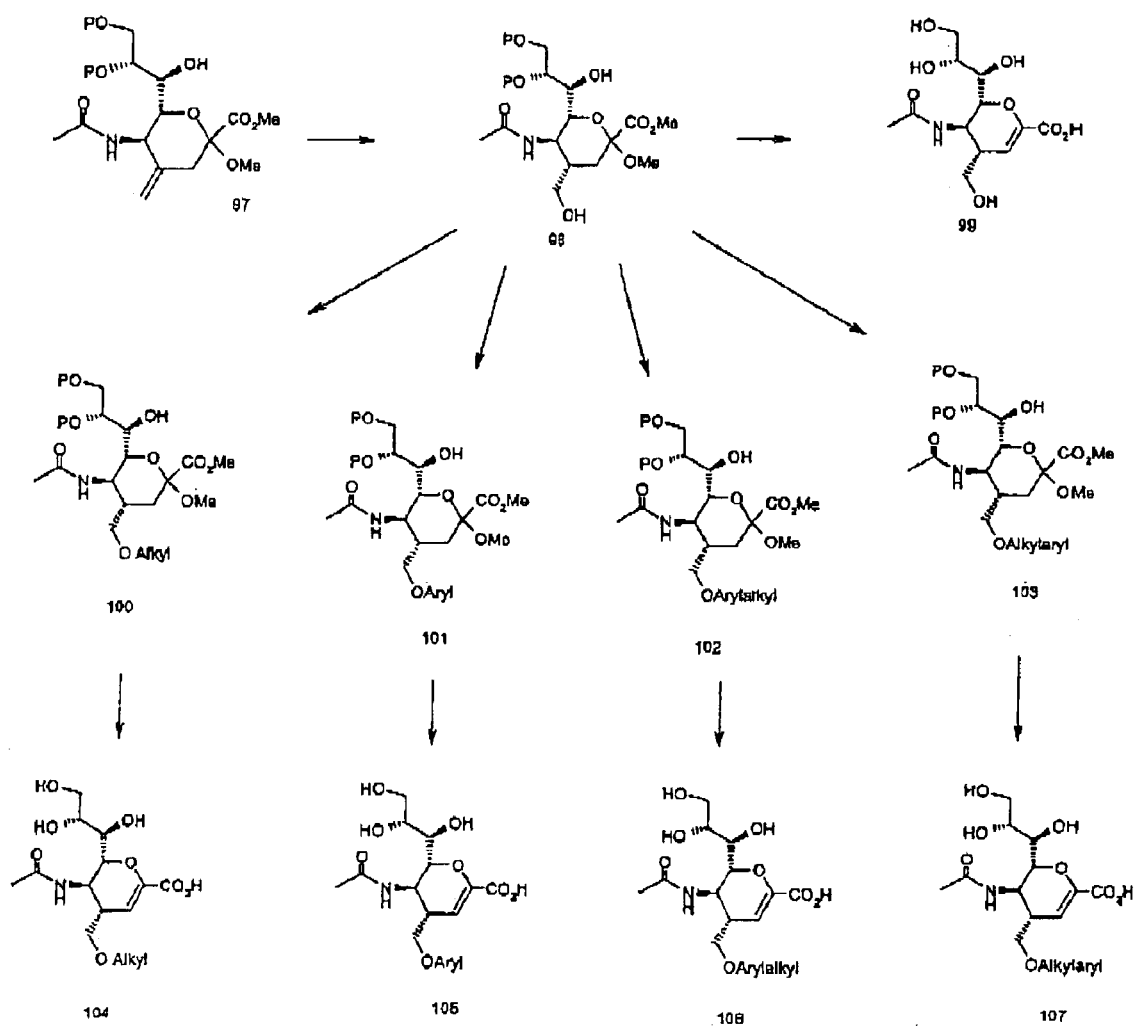
Figure 15:
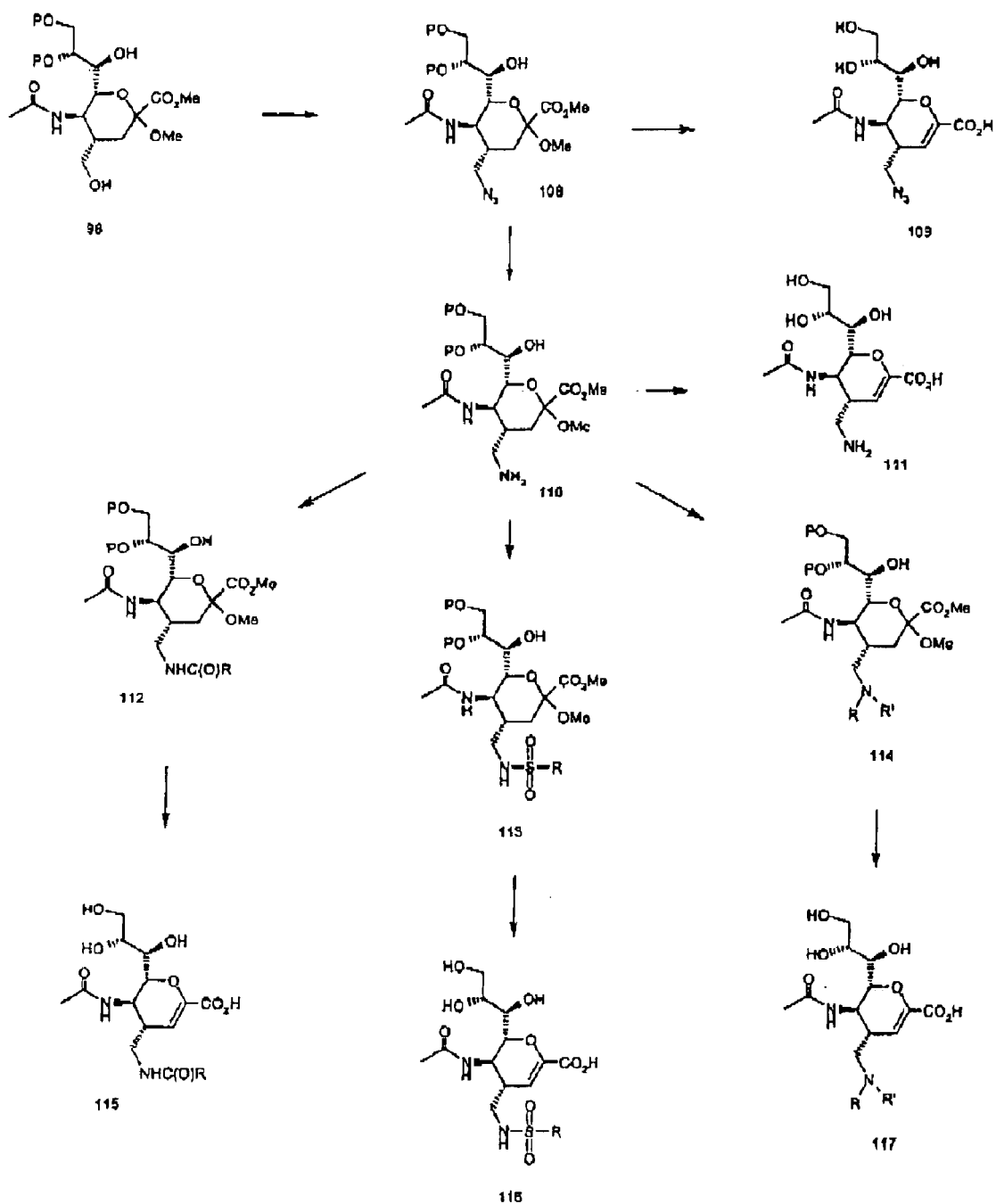
Figure 16:
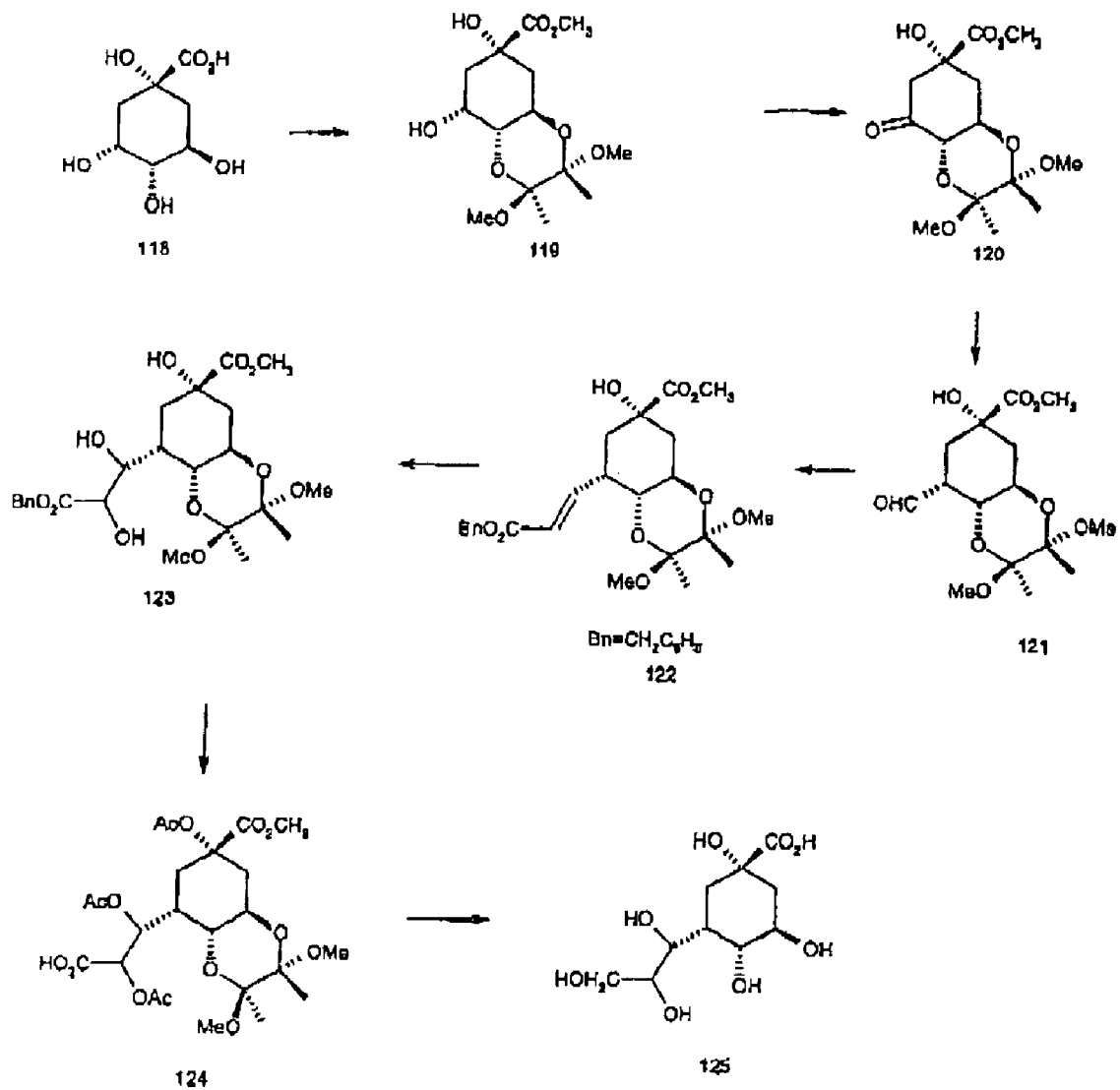
Figure 17:
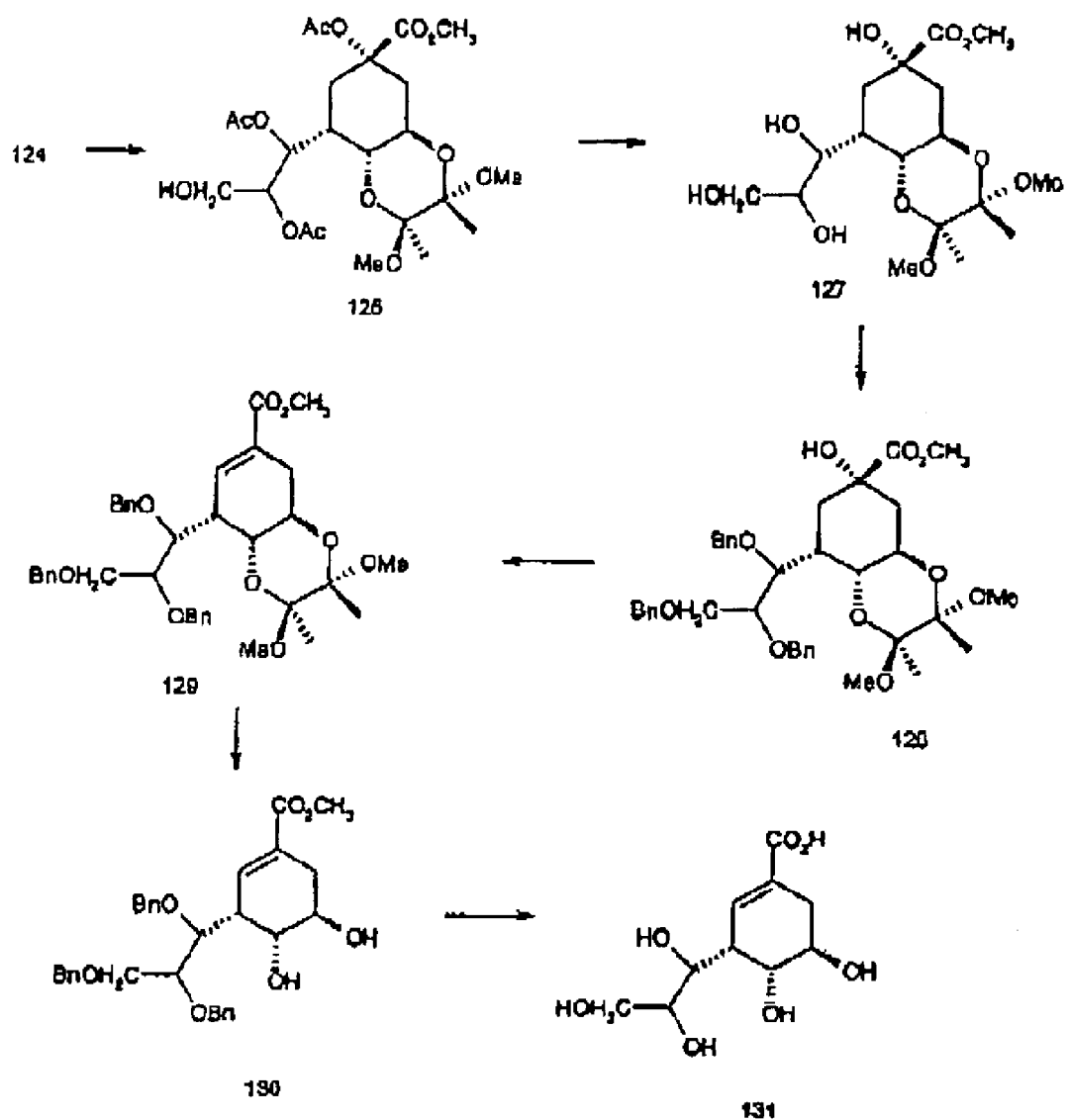
Figure 18:
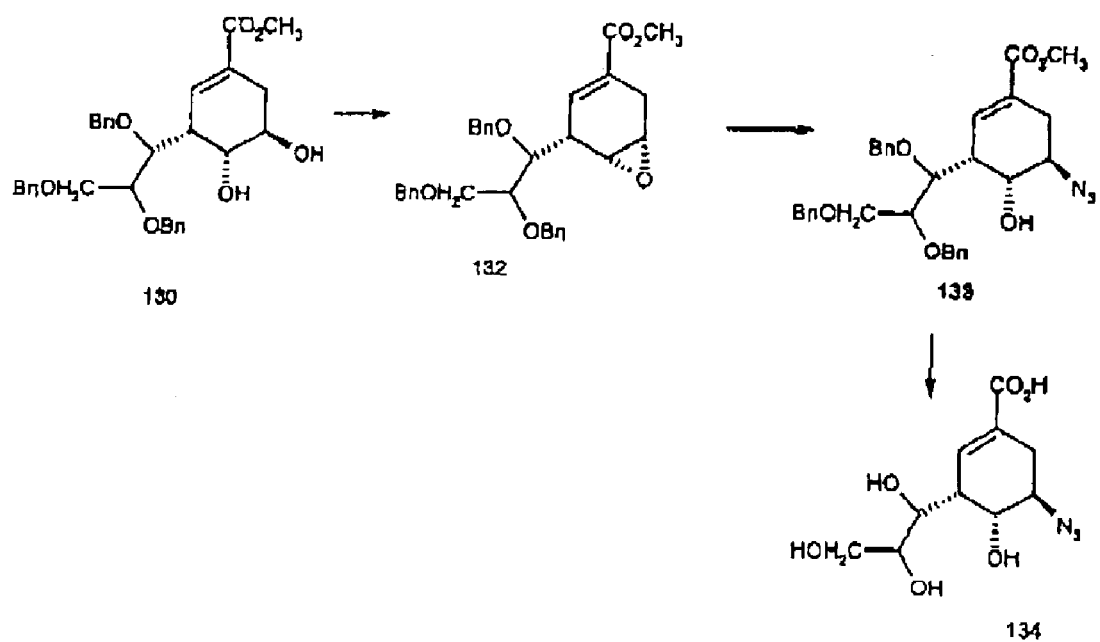
Figure 19:
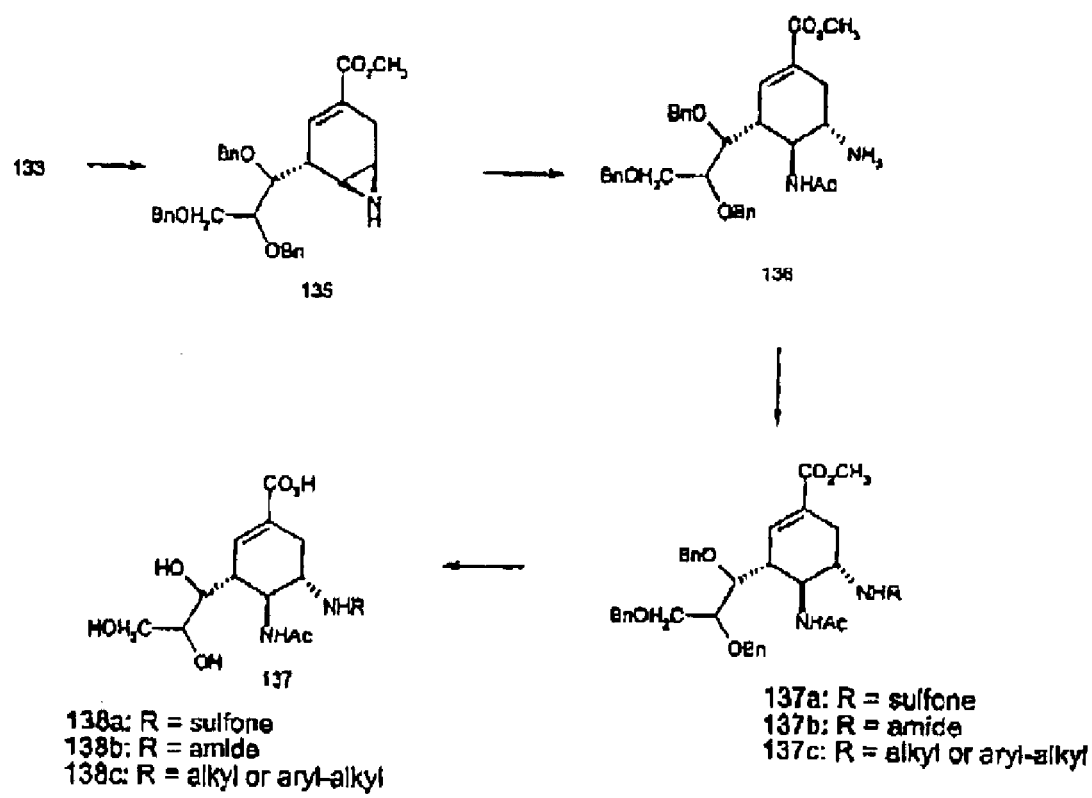
Figure 20:
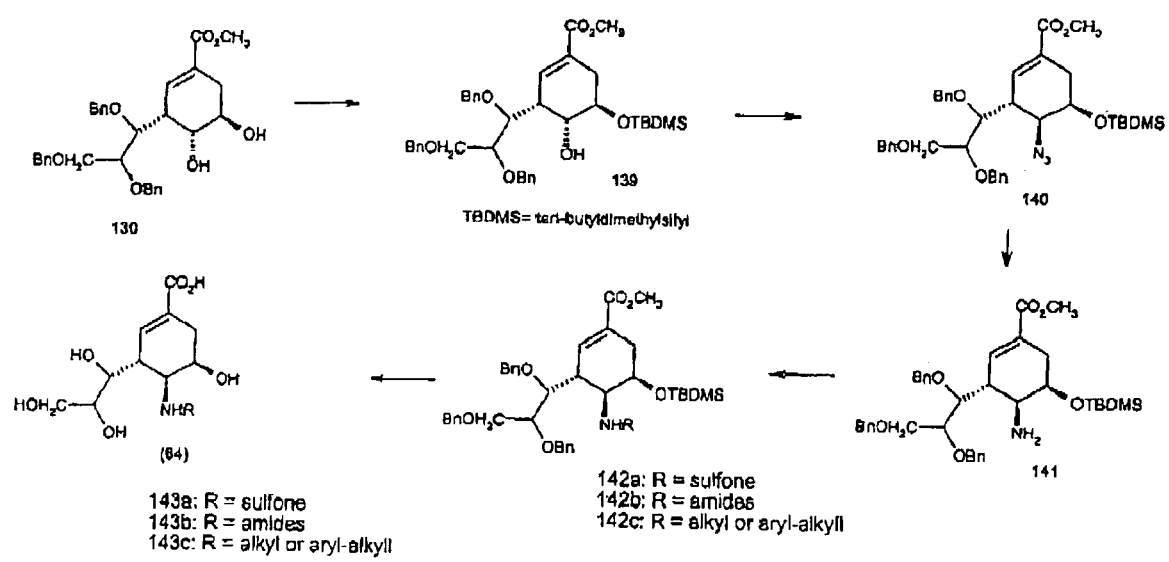
Figure 21:
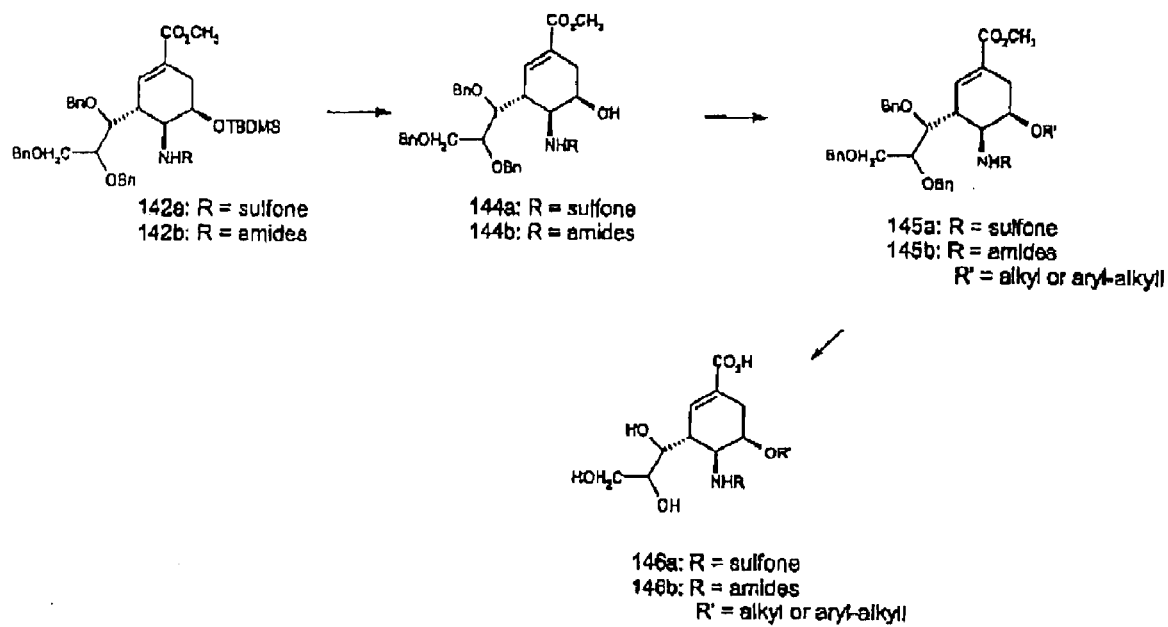
Figure 22:
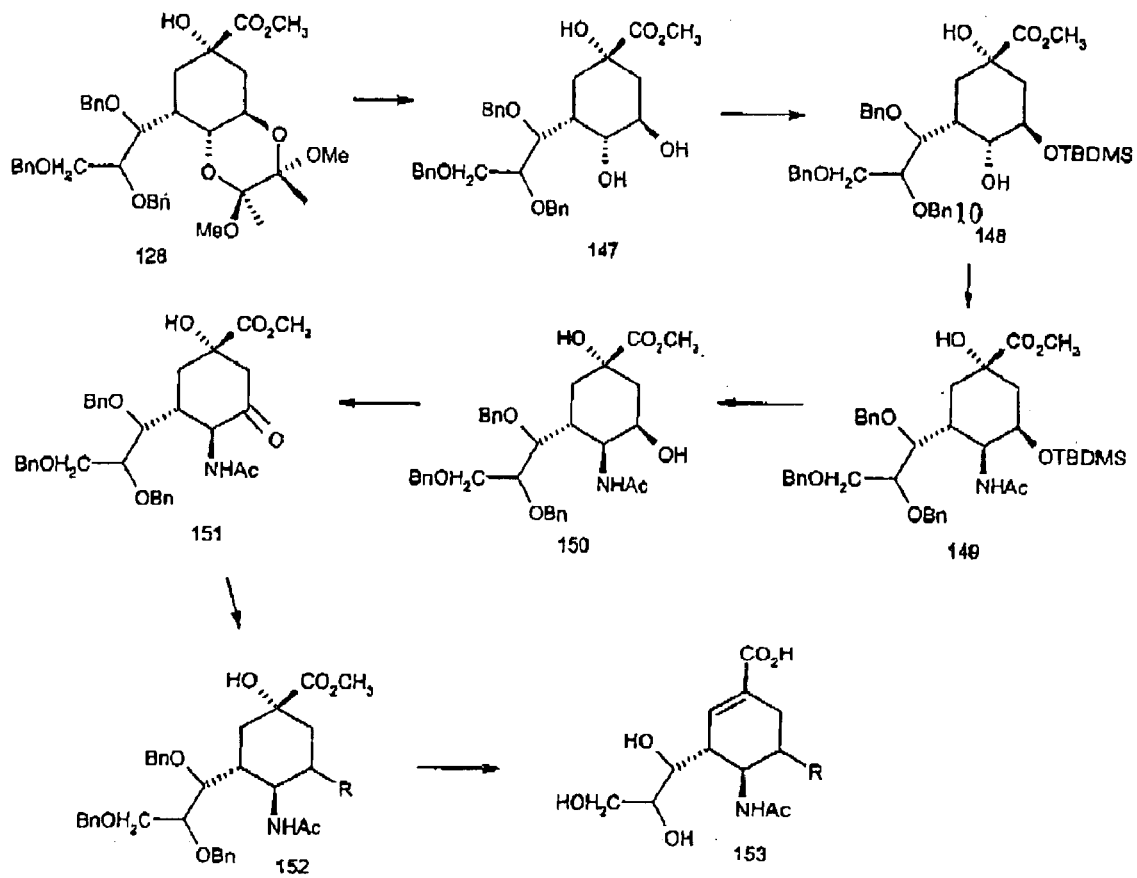
Figure 23:
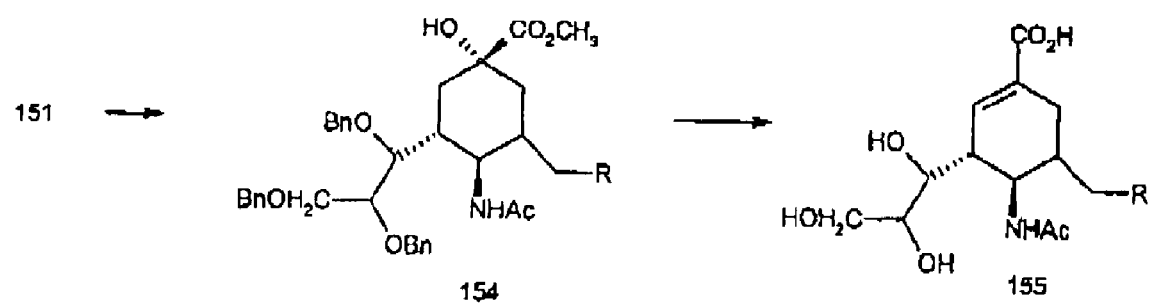

Examples of some specific compounds within the scope of the present invention are:

(2R,3R,4S)-3-(Acetylamino)-4-(benzoylamino)-2-[(1R, 2R)-1,2,3-trihydroxpropyl]-3,4-dihydro-2H-pyran-6-carboxylic acid (2R,3R,4S)-3-(Acetylamino)-4-[(3-methylbutanoyl)amino]-2-[(1R,2R)-1,2,3-trihydroxypropyl]-3,4-dihydro-2H-pyran-6-carboxylic acid (2R,3R,4S)-3-(Acetylamino)-4-(2-furoylamino)-2-[(1R, 2R)-1,2,3-trihydroxypropyl]-3,4-dihydro-2H-pyran-6-carboxylic acid (2R,3R,4S)-3,4-Bis(acetylamino)-2-[(1R,2R)-1,2,3-trihydroxypropyl]-3,4-dihydro-2H-pyran-6-carboxylic acid (2R,3R,4S)-3-(Acetylamino)-4-[(thien-2-ylacetyl)amino]-2-[(1R,2R)-1,2,3-trihydroxypropyl]-3,4-dihydro-2H-pyran-6-carboxylic acid (2R,3R,4S)-3-(Acetylamino)-4-[(thien-2-ylcarbonyl)amino]-2-[(1R,2R)-1,2,3-trihydroxypropyl]-3,4-dihydro-2H-pyran-6-carboxylic acid (2R,3R,4S)-3-(Acetylamino)-4-[(thien-3-ylacetyl)amino]-2-[(1R,2R)-1,2,3-trihydroxypropyl]-3,4-dihydro-2H-pyran-6-carboxylic acid (2R,3R,4S)-3-(Acetylamino)-4-[(phenylacetyl)amino]-2-[(1R,2R)-1,2,3-trihydroxypropyl]-3,4-dihydro-2H-pyran-6-carboxylic acid (2R,3R,4S)-3-(Acetylamino)-4-[(thien-2-ylmethyl)amino]-2-[(1R,2)-1,2,3-trihydroxypropyl]-3,4-dihydro-2H-pyran-6-carboxylic acid (2R,3R,4S)-3-(Acetylamino)-4-[(4-chlorobenzyl)amino]-2-[(1R,2R)-1,2,3-trihydroxypropyl]-3,4-dihydro-2H-pyran-6-carboxylic acid (2R,3R,4S)-3-(Acetylamino)-4-(benzylamino)-2-[(1R,2R)-1,2,3-trihydroxypropyl]-3,4-dihydro-2H-pyran-6-carboxylic acid 1-{(2R,3R,4S)-3-(Acetylamino)-6-carboxy-2-[(1R,2R)-1,2,3-trihydroxypropyl]-3,4-dihydro-2H-pyran-4-yl}-1H-1,2,3-triazole-4-carboxylic acid (2R,3R,4S)-3-(Acetylamino)-4-[(1-ethylpropyl)amino]-2-[(1R,2R)-1,2,3-trihydroxypropyl]-3,4-dihydro-2H-pyran-6-carboxylic acid (2R,3R,4S)-3-(Acetylamino)-4-(isopropylamino)-2-[(1R,2R)-1,2,3-trihydroxypropyl]-dihydro-2H-pyran-6-carboxylic acid (2R,3R,4S)-3-(Acetylamino)-4-(sec-butylamino)-2-[(1R,2R)-1,2,3-trihydroxypropyl]-3,4-dihydro-2H-pyran-6-carboxylic acid (2R,3R,48)-3-(Acetylamino)-4-[(1,3-dimethylbutyl)amino]-2-[(1R,2R)-1,2,3-trihydroxypropyl]-3,4-dihydro-2H-pyran-6-carboxylic acid (2R,3R,4S)-3-(Acetylamino)-4-[(1-methylpentyl)amino]-2-[(1R,2R)-1,2,3-trihydroxypropyl]-3,4-dihydro-2H-pyran-6-carboxylic acid (2R,3R,4S)-3-(Acetylamino)-4-[(1-isopropylbutyl)amino]-2-[(1R,2R)-1,2,3-trihydroxypropyl]-3,4-dihydro-2H-pyran-6-carboxylic acid (2R,3R,4S)-3-(Acetylamino)-4-[(1,4-dimethylpentyl)amino]-2-[(1R,2R)-1,2,3-trihydroxypropyl]-3,4-dihydro-2H-pyran-6-carboxylic acid (2R,3R,4S)-3-(Acetylamino)-4-[(3-carboxy-1-methylpropyl)amino]-2-[(1R,2R)-1,2,3-trihydroxypropyl]-3,4-dihydro-2H-pyran-6-carboxylic acid (2R,3R,4S)-3-(Acetylamino)-4-[(1,2-dimethylbutyl)amino]-2-[(1R,2R)-1,2,3-trihydroxypropyl]-3,4-dihydro-2H-pyran-6-carboxylic acid (2R,3R,4S)-3-(Acetylamino)-4-[(1-benzylpropyl)amino]-2-[(1R,2R)-1,2,3-trihydroxypropyl]-3,4-dihydro-2H-pyran-6-carboxylic acid (2R,3R,4S)-3-(Acetylamino)-4-[(2-methylbutyl)amino]-2-[(1R,2R)-1,2,3-trihydroxypropyl]-3,4-dihydro-2H-pyran-6-carboxylic acid (2R,3R,4S)-3-(Acetylamino)-4-[(3-phenylbutyl)amino]-2-[(1R,2R)-1,2,3-trihydroxypropyl]-3,4-dihydro-2H-pyran-6-carboxylic acid (2R,3R,4S)-3-(Acetylamino)-4-(isobutylamino)-2-[(1R,2R)-1,2,3-trihydroxypropyl]-3,4-dihydro-2H-pyran-6-carboxylic acid (2R,3R,4S)-3-(Acryloylamino)-4-hydroxy-2-[(1R,2R)-1,2,3-trihydroxypropyl]-3,4-dihydro-2H-pyran-6-carboxylic acid (2R,3R,4S)-3-[(Cyclobutylcarbonyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(propionylamino)-2-[(1R,2R)-1,2,3-trihydroxypropyl]-3,4-dihydro-2H-pyran-6-carboxylic acid (2R,3R,4S)-3-[(Cyclopentylcarbonyl)amino]-4-hydroxy-2-[(1R,2R)-1,2,3-trihydroxypropyl]-3,4-dihydro-2H-pyran-6-carboxylic acid (2R,3R,4S)-3-(2-Furoylamino)-4-hydroxy-2-[(1R,2R)-1,2,3-trihydroxypropyl]-3,4-dihydro-2H-pyran-6-carboxylic acid (2R,3R,4S)-4-Hydroxy-3-[(thien-2-ylcarbonyl)amino]-2-[(1R,2R)-1,2,3-trihydroxypropyl]-3,4-dihydro-2H-pyran-6-carboxylic acid (2R,3R,4S)-3-(Butyrylamino)-4-hydroxy-2-[(1R,2R)-1,2,3-trihydroxypropyl]-3,4-dihydro-2H-pyran-6-carboxylic acid (2R,3R,4S)-4-Hydroxy-3-[(3-methylbutanoyl)amino]-2-[(1R,2R)-1,2,3-trihydroxypropyl]-3,4-dihydro-2H-pyran-6-carboxylic acid (2R,3R,4S)-3-[(Cyclopropylcarbonyl)amino]-4-hydroxy-2-[(1R,2R)-1,2,3-trihydroxypropyl]-3,4-dihydro-2H-pyran-6-carboxylic acid (2R,3R,4S)-3-[(3,3-Dimethylbutanoyl)amino]-4-hydroxy-2-[(1R,2R)-1,2,3-trihydroxypropyl]-3,4-dihydro-2H-pyran-6-carboxylic acid (2R,3R,4S)-3-(Benzoylamino)-4-hydroxy-2-[(1R,2R)-1,2,3-trihydroxypropyl]-3,4-dihydro-2H-pyran-6-carboxylic acid (2R,3R,4S)-4-Hydroxy-3-(isobutyrylamino)-2-[(1R,2R)-1,2,3-trihydroxypropyl]-3,4-dihydro-2H-pyran-6-carboxylic acid (2R,3R,4S)-3-[(tert-Butoxycarbonyl)amino]-4-hydroxy-2-[(1R,2R)-1,2,3-trihydroxypropyl]-3,4-dihydro-2H-pyran-6-carboxylic acid (2R,3R,4S)-3-[(2,2-Dimethylpropanoyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-[(3-phenylpropanoyl)amino]-2-[(1R,2R)-1,2,3-trihydroxypropyl]-3,4-dihydro-2H-pyran-6-carboxylic acid (2R,3R,4S)-3-[(2-Chloropropanoyl)amino]-4-hydroxy-2-[(1R,2R)-1,2,3-trihydroxypropyl]-3,4-dihydro-2H-pyran-6-carboxylic acid (2R,3R,4S)-3-[(Chloroacetyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(methacryloylamino)-2-[(1R,2R)-1,2,3-trihydroxypropyl]-3,4-dihydro-2H-pyran-6-carboxylic acid (2R,3R,4S)-3-[(2-Ethylbutanoyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-[(phenylacetyl)amino]-2-[(1R,2R)-1,2,3-trihydroxypropyl]-3,4-dihydro-2H-pyran-6-carboxylic acid (2R,3R,4S)-4-Hydroxy-3-[(3-methylbut-2-enoyl)amino]-2-[(1R,2R)-1,2,3-trihydroxypropyl]-3,4-dihydro-2H-pyran-6-carboxylic acid (2R,3R,4S)-4-Hydroxy-3-[(thien-2-ylacetyl)amino]-2-[(1R,2R)-1,2,3-trihydroxypropyl]-3,4-dihydro-2H-pyran-6-carboxylic acid (2R,3R,4S)-4-Hydroxy-3-[(2-methylbutanoyl)amino]-2-[(1R,2R)-1,2,3-trihydroxypropyl]-3,4-dihydro-2H-pyran-6-carboxylic acid (2R,3R 4S)-3-[(4-Chlorobutanoyl)amino]-4-hydroxy-2-[(1R,2R)-1,2,3-trihydroxypropyl]-3,4-dihydro-2H-pyran-6-carboxylic acid (2R,3R,4S)-3-[(5-Chloropentanoyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(2-oxopiperidin-1-yl)-2-[(1R,2R)-1,2,3-trihydroxypropyl]-dihydro-2H-pyran-6-carboxylic acid (2R,3R,4S)-4-Hydroxy-3-(2-oxopyrrolidin-1-yl)-2-[(1R,2R)-1,2,3-trihydroxypropyl]-dihydro-2H-pyran-6-carboxylic acid (2R,3R,4S)-3-[(1-Ethylpropyl)amino]-4-hydroxy-2-[(1R,2R)-1,2,3-trihydroxypropyl]-dihydro-2H-pyran-6-carboxylic acid (2R,3R,4S)-4-Hydroxy-3-(isopropylamino)-2-[(1R,2R)-1,2,3-trihydroxypropyl]-3,4-dihydro-2H-pyran-6-carboxylic acid (2R,3R,4S)-3-[(1,3-Dimethylbutyl)amino]-4-hydroxy-2-[(1R,2R)-1,2,3-trihydroxypropyl]-3,4-dihydro-2H-pyran-6-carboxylic acid (2R,3R,4S)-3-(Diethylamino)-4-hydroxy-2-[(1R,2R)-1,2,3-trihydroxypropyl]-3,4-dihydro-2H-pyran-6-carboxylic acid (2R,3R,4S)-3-(sec-Butylamino)-4-hydroxy-2-[(1R,2R)-1,2,3-trihydroxypropyl]-3,4-dihydro-2H-pyran-6-carboxylic acid (2R,3R,4S)-3-[(1,4-Dimethylpentyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-[(1-methylpentyl)amino]-2-[(1R,2R)-1,2,3-trihydroxypropyl]-3,4-dihydro-2H-pyran-6-carboxylic acid (2R,3R,4S)-4-Hydroxy-3-[(2-hydroxy-1-methylethyl)amino]-2-[(1R,2R)-1,2,3-trihydroxypropyl]-3,4-dihydro-2H-pyran-6-carboxylic acid (2R,3R,4S)-3-[(1-Benzylpropyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(isopentylamino)-2-[(1R,2R)-1,2,3-trihydroxypropyl]-3,4-dihydro-2H-pyran-6-carboxylic acid (2R,3R,4S)-3-[(3,3-Dimethylbutyl)amino]-4-hydroxy-2-[(1R,2R)-1,2,3-trihydroxypropyl]-3,4-dihydro-2H-pyran-6-carboxylic acid (2R,3R,4S)-3-(Butylamino)-4-hydroxy-2-[(1R,2R)-1,2,3-trihydroxypropyl]-3,4-dihydro-2H-pyran-6-carboxylic acid (2R,3R,4S)-3-[(1,2-Dimethylbutyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(isobutylamino)-2-[(1R,2R)-1,2,3-trihydroxypropyl]-3,4-dihydro-2H-pyran-6-carboxylic acid (2R,3R,4S)-4-Hydroxy-3-pyrrolidin-1-yl-2-[(1R,2R)-1,2,3-trihydroxypropyl]-3,4-dihydro-2H-pyran-6-carboxylic acid (2R,3R,4S)-4-Hydroxy-3-(neopentylamino)-2-[(1R,2R)-1,2,3-trihydroxypropyl]-3,4-dihydro-2H-pyran-6-carboxylic acid (2R,3R,4S)-4-Azido-3-[(2-methylbutanoyl)amino]-2-[(1R,2R)-1,2,3-trihydroxypropyl]-3,4-dihydro-2H-pyran-6-carboxylic acid (2R,3R,4S)-4-Azido-3-(isobutylamino)-2-[(1R,2R)-1,2,3-trihydroxypropyl]-3,4-dihydro-2H-pyran-6-carboxylic acid (2R,3R,4S)-4-Azido-3-(isobutyrylamino)-2-[(1R,2R)-1,2,3-trihydroxypropyl]-3,4-dihydro-2H-pyran-6-carboxylic acid (2R,3R,4S)-4-Azido-3-[(cyclopropylcarbonyl)amino]-2-[(1R,2R)-1,2,3-trihydroxypropyl]-3,4-dihydro-2H-pyran-6-carboxylic acid (2R,3R,4S)-4-Azido-3-[(cyclobutylcarbonyl)amino]-2-[(1R,2R)-1,2,3-trihydroxypropyl]-3,4-dihydro-2H-pyran-6-carboxylic acid (2R,3R,4S)-4-(Benzylamino)-3-(isobutyrylamino)-2-[(1R,2R)-1,2,3-trihydroxypropyl]-3,4-dihydro-2H-pyran-6-carboxylic acid (2R,3R,4S)-4-[(4-Chlorobenzyl)amino]-3-(isobutyrylamino)-2-[(1R,2R)-1,2,3-trihydroxypropyl]-3,4-dihydro-2H-pyran-6-carboxylic acid (2R,3R,4S)-3-(Isobutyrylamino)-4-[(thien-2-ylmethyl)amino]-2-[(1R,2R)-1,2,3-trihydroxypropyl]-3,4-dihydro-2H-pyran-6-carboxylic acid (2R,3R,4S)-3-(Acetylamino)-4-(1H-1,2,3-triazol-1-yl)-2-[(1R,2R)-1,2,3-trihydroxypropyl]-3,4-dihydro-2H-pyran-6-carboxylic acid (2R,3R,4S)-3-(Acetylamino)-4-[(4-chlorobenzyl)oxy]-2-[(1R,2R)-1,2,3-trihydroxypropyl]-3,4-dihydro-2H-pyran-6-carboxylic acid (2R,3R,4S)-3-(Acetylamino)-4-butoxy-2-[(1R,2R)-1,2,3-trihydroxypropyl]-3,4-dihydro-2H-pyran-6-carboxylic acid (2R,3R,4S)-3-(Acetylamino)-4-(pent-4-enyloxy)-2-[(1R,2R)-1,2,3-trihydroxypropyl]-3,4-dihydro-2H-pyran-6-carboxylic acid (2R,3R,4S)-3-(Acetylamino)-4-(hex-5-enyloxy)-2-[(1R,2R)-1,2,3-trihydroxypropyl]-3,4-dihydro-2H-pyran-6-carboxylic acid (2R,3R,4S)-3-(Acetylamino)-4-(3-bromopropoxy)-2-[(1R,2R)-1,2,3-trihydroxypropyl]-3,4-dihydro-2H-pyran-6-carboxylic acid (2R,3R,4S)-3-(Acetylamino)-4-(but-2-ynyloxy)-2-[(1R,2R)-1,2,3-trihydroxypropyl]-3,4-dihydro-2H-pyran-6-carboxylic acid (2R,3R,4S)-3-(Acetylamino)-4-[(2-methylprop-2-enyl)oxy]-2-[(1R,2R)-1,2,3-trihydroxypropyl]-3,4-dihydro-2H-pyran-6-carboxylic acid (2R,3R,4S)-3-(Acetylamino)-4-[(2E)-but-2-enyloxy]-2-[(1R,2R)-1,2,3-trihydroxypropyl]-3,4-dihydro-2H-pyran-6-carboxylic acid (2R,3R,4S)-3-(Acetylamino)-4-(3-chloropropoxy)-2-[(1R,2R)-1,2,3-trihydroxypropyl]-3,4-dihydro-2H-pyran-6-carboxylic acid (2R,3R,4S)-3-(Acetylamino)-4-[(2-ethylhexyl)oxy]-2-[(1R,2R)-1,2,3-trihydroxypropyl]-3,4-dihydro-2H-pyran-6-carboxylic acid (2R,3R,4S)-3-(Acetylamino)-4-isobutoxy-2-[(1R,2R)-1,2,3-trihydroxypropyl]-3,4-dihydro-2H-pyran-6-carboxylic acid (2R,3R,4S)-3-(Acetylamino)-4-(cyclohexylmethoxy)-2-[(1R,2R)-1,2,3-trihydroxypropyl]-3,4-dihydro-2H-pyran-6-carboxylic acid (2R,3R,4S)-3-(Acetylamino)-4-(carboxymethoxy)-2-[(1R,2R)-1,2,3-trihydroxypropyl]-3,4-dihydro-2H-pyran-6-carboxylic acid (2R,3R,4S)-3-(Acetylamino)-4-(2-oxobutoxy)-2-[(1R,2R)-1,2,3-trihydroxypropyl]-3,4-dihydro-2H-pyran-6-carboxylic acid (2R,3R,4S)-3-(Acetylamino)-4-[(2-carboxyprop-2-enyl)oxy]-2-[(1R,2R)-1,2,3-trihydroxypropyl]-3,4-dihydro-2H-pyran-6-carboxylic acid (2R,3R,4S)-3-(Acetylamino)-4-(2-methoxyethoxy)-2-[(1R,2R)-1,2,3-trihydroxypropyl]-3,4-dihydro-2H-pyran-6-carboxylic acid (2R,3R,4S)-3-(Acetylamino)-4-[(2E)-pent-2-enyloxy]-2-[(1R,2R)-1,2,3-trihydroxypropyl]-3,4-dihydro-2H-pyran-6-carboxylic acid (2R,3R,4S)-3-(Acetylamino)-4-(cyclopropylmethoxy)-2-[(1R,2R)-1,2,3-trihydroxypropyl]-3,4-dihydro-2H-pyran-6-carboxylic acid (2R,3R,4S)-3-(Acetylamino)-4-ethoxy-2-[(1R,2R)-1,2,3-trihydroxypropyl]-3,4-dihydro-2H-pyran-6-carboxylic acid (2R,3R,4S)-3-(Acetylamino)-4-(benzyloxy)-2-[(1R,2R)-1,2,3-trihydroxypropyl]-3,4-dihydro-2H-pyran-6-carboxylic acid (2R,3R,4S)-3-(acetylamino)-4-propoxy-2-[(1R,2R)-1,2,3-trihydroxypropyl]-3,4-dihydro-2H-pyran-6-carboxylic acid (2R,3R,4S)-3-(Acetylamino)-4-(allyloxy)-2-[(1R,2R)-1,2,3-trihydroxypropyl]-3,4-dihydro-2H-pyran-6-carboxylic acid (2R,3R,4S)-3-(Acetylamino)-4-methoxy-2-[(1R,2R)-1,2,3-trihydroxypropyl]-3,4-dihydro-2H-pyran-6-carboxylic acid (2R,3R,4R)-4-(Benzyloxy)-3-(isobutyrylamino)-2-[(1R,2R)-1,2,3-trihydroxypropyl]-3,4-dihydro-2H-pyran-6-carboxylic acid (2R,3R,4R)-4-[(4-Chlorobenzyl)oxy]-3-(isobutyrylamino)-2-[(1R,2R)-1,2,3-trihydroxypropyl]-3,4-dihydro-2H-pyran-6-carboxylic acid (2R,3R,4R)-3-(Isobutyrylamino)-4-{[(2E)-3-phenylprop-2-enyl]oxy}-2-[(1R,2R)-1,2,3-trihydroxypropyl]-3,4-dihydro-2H-pyran-6-carboxylic acid (2R,3R,4R)-4-(Allyloxy)-3-(isobutyrylamino)-2-[(1R,2R)-1,2,3-trihydroxypropyl]-3,4-dihydro-2H-pyran-6-carboxylic acid (2R,3R,4R)-4-Isobutoxy-3-(isobutyrylamino)-2-[(1R,2R)-1,2,3-trihydroxypropyl]-3,4-dihydro-2H-pyran-6-carboxylic acid (2R,3R,4R)-3-(Isobutyrylamino)-4-propoxy-2-[(1R,2R)-1,2,3-trihydroxypropyl]-3,4-dihydro-2H-pyran-6-carboxylic acid (2R,3R,4R)-3-(Isobutyrylamino)-4-methoxy-2-[(1R,2R)-1,2,3-trihydroxypropyl]-3,4-dihydro-2H-pyran-6-carboxylic acid (2R,3R,4R)-4-Ethoxy-3-(isobutyrylamino)-2-[(1R,2R)-1,2,3-trihydroxypropyl]-3,4-dihydro-2H-pyran-6-carboxylic acid (2R,3R,4R)-3-(Isobutyrylamino)-4-(thien-2-ylmethoxy)-2-[(1R,2R)-1,2,3-trihydroxypropyl]-3,4-dihydro-2H-pyran-6-carboxylic acid (2R,3R,4S)-3-(Acetylamino)-4-methoxy-2-[(1R,2R)-1,2,3-trihydroxypropyl]-3,4-dihydro-2H-pyran-6-carboxylic acid (2R,3R,4S)-3-(Acetylamino)-4-azido-2-[(butylamino)carbonyl]-3,4-dihydro-2H-pyran-6-carboxylic acid (2R,3R,4S)-3-(Acetylamino)-4-azido-2-[(isobutylamino)carbonyl]-3,4-dihydro-2H-pyran-6-carboxylic acid (2R,3R,4S)-3-(Acetylamino)-4-azido-2-[(dimethylamino)carbonyl]-3,4-dihydro-2H-pyran-6-carboxylic acid (2R,3R,4S)-3-(Acetylamino)-4-azido-2-[(benzylamino)carbonyl]-3,4-dihydro-2H-pyran-6-carboxylic acid (2R,3R,4S)-3-(Acetylamino)-4-azido-2-[(isopropylamino)carbonyl]-3,4-dihydro-2H-pyran-6-carboxylic acid (2R,3R,4S)-3-(Acetylamino)-4-azido-2-[(methylamino)carbonyl]-3,4-dihydro-2H-pyran-6-carboxylic acid (2R,3R,4S)-3-(Acetylamino)-4-[(thien-2-ylsulfonyl)amino]-2-[(1R,2R)-1,2,3-trihydroxypropyl]-3,4-dihydro-2H-pyran-6-carboxylic acid (2R,3R,4S)-3-(Acetylamino)-4-[(methylsulfonyl)amino]-2-[(1R,2R)-1,2,3-trihydroxypropyl]-3,4-dihydro-2H-pyran-6-carboxylic acid (2R,3R,4S)-3-(Acetylamino)-4-[(phenylsulfonyl)amino]-2-[(1R,2R)-1,2,3-trihydroxypropyl]-3,4-dihydro-2H-pyran-6-carboxylic acid (2R,3R,4S)-3-(Acetylamino)-4-{[(2,2,2-trifluoroethyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(benzylsulfonyl)amino]-2-[(1R,2R)-1,2,3-trihydroxypropyl]-3,4-dihydro-2H-pyran-6-carboxylic acid (2R,3R,4S)-3-(Acetylamino)-4-[(propylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(methylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(phenylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(benzylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(thien-2-ylsulfonyl)amino]-2-[(1R,2R)-1,2,3-trihydroxypropyl]-3,4-dihydro-2H-pyran-6-carboxylic acid (2R,3R,4S)-3-(Acetylamino)-4-({[(E)-2-phenylethenyl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-{[(2-nitrobenzyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(2-nitrophenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-nitrophenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-fluorophenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-chlorophenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(2-naphthylsulfonyl)amino]-2-[(1R,2R)-1,2,3-trihydroxypropyl]-3,4-dihydro-2H-pyran-6-carboxylic acid (2R,3R,4S)-3-(Acetylamino)-4-{[(4-methoxyphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-tert-butylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(1-naphthylsulfonyl)amino]-2-[(1R,2R)-1,2,3-trihydroxypropyl]-3,4-dihydro-2H-pyran-6-carboxylic acid (2R,3R,4S)-3-(Acetylamino)-4-{[(4-carboxyphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-methylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(ethylsulfonyl)amino]-2-[(1R,2R)-1,2,3-trihydroxypropyl]-3,4-dihydro-2H-pyran-6-carboxylic acid (2R,3R,4S)-3-(Acetylamino)-2-[(1R,2R)-1,2,3-trihydroxypropyl]-4-[(vinylsulfonyl)amino]-3,4-dihydro-2H-pyran-6-carboxylic acid (2R,3R,4S)-3-(Acetylamino)-4-({[2-(acetylamino)-4-methyl-1,3-thiazol-5-yl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-({[4-(acetylamino)phenyl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-{[(2-methylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[({4-[(methoxycarbonyl)amino]phenyl}sulfonyl)amino]-2-[(1R,2R)-1,2,3-trihydroxypropyl]-3,4-dihydro-2H-pyran-6-carboxylic acid (2R,3R,4S)-3-(Acetylamino)-4-({[(methylsulfonyl)methyl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-{[(1,2-dimethyl-1H-imidazol-4-yl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-chloro-4-methylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3,5-dimethylisoxazol-4-yl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-carboxy-4-hydroxyphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(dichloromethyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-chloropropyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-isopropylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-ethylphenyl)sulfonyl]amino}-2-[(1R,2R)-1,2,3-trihydroxypropyl]-3,4-dihydro-2H-pyran-6-carboxylic acid (2R,3R,4S)-4-{[(Dichloromethyl)sulfonyl]amino}-3-(isobutyrylamino)-2-[(1R,2R)-1,2,3-trihydroxypropyl]-3,4-dihydro-2H-pyran-6-carboxylic acid (2R,3R,4S)-4-{[(4-Chlorophenyl)sulfonyl]amino}-3-(isobutyrylamino)-2-[(1R,2R)-1,2,3-trihydroxypropyl]-3,4-dihydro-2H-pyran-6-carboxylic acid (2R,3R,4S)-3-(Isobutyrylamino)-4-{[(4-methylphenyl)sulfonyl]amino}-2-[(1R,2R)-1,2,3-trihydroxypropyl]-3,4-dihydro-2H-pyran-6-carboxylic acid (2R,3R,4S)-4-{[(3-Chloro-4-methylphenyl)sulfonyl]amino}-3-(isobutyrylamino)-2-[(1R,2R)-1,2,3-trihydroxypropyl]-3,4-dihydro-2H-pyran-6-carboxylic acid (2R,3R,4S)-3-(Isobutyrylamino)-4-[(thien-2-ylsulfonyl)amino]-2-[(1R,2R)-1,2,3-trihydroxypropyl]-3,4-dihydro-2H-pyran-6-carboxylic acid (2R,3R,4S)-3-(Isobutyrylamino)-4-({[(E)-2-phenylethenyl]sulfonyl}amino)-2-[(1R,2R)-1,2,3-trihydroxypropyl]-3,4-dihydro-2H-pyran-6-carboxylic acid (2R,3R,4S)-3-[(Cyclopropylcarbonyl)amino]-4-{[(dichloromethyl)sulfonyl]amino}-2-[(1R,2R)-1,2,3-trihydroxypropyl]-3,4-dihydro-2H-pyran-6-carboxylic acid (2R,3R,4S)-4-{[(4-Chlorophenyl)sulfonyl]amino}-3-[(cyclopropylcarbonyl)amino]-2-[(1R,2R)-1,2,3-trihydroxypropyl]-3,4-dihydro-2H-pyran-6-carboxylic acid (2R,3R,4S)-3-[(Cyclopropylcarbonyl)amino]-4-{[(4-methylphenyl)sulfonyl]amino}-2-[(1R,2R)-1,2,3-trihydroxypropyl]-3,4-dihydro-2H-pyran-6-carboxylic acid (2R,3R,4S)-4-{[(3-Chloro-4-methylphenyl)sulfonyl]amino}-3-[(cyclopropylcarbonyl)amino]-2-[(1R,2R)-1,2,3-trihydroxypropyl]-3,4-dihydro-2H-pyran-6-carboxylic acid (2R,3R,4S)-3-[(Cyclopropylcarbonyl)amino]-4-({[(E)-2-phenylethenyl]sulfonyl}amino)-2-[(1R,2R)-1,2,3-trihydroxypropyl]-3,4-dihydro-2H-pyran-6-carboxylic acid (2R,3R,4S)-3-[(Cyclopropylcarbonyl)amino]-4-[(thien-2-ylsulfonyl)amino]-2-[(1R,2R)-1,2,3-trihydroxypropyl]-3,4-dihydro-2H-pyran-6-carboxylic acid (2R,3R,4S)-4-Hydroxy-3-[(methylsulfonyl)amino]-2-[(1R,2R)-1,2,3-trihydroxypropyl]-3,4-dihydro-2H-pyran-6-carboxylic acid The schemes shown in FIGS. 1–23 illustrate methods for preparing compounds of the present invention. In order to facilitate an understanding of the present invention, the methods will be discussed with respect to preparing various preferred compounds of the present invention.

Scheme 1

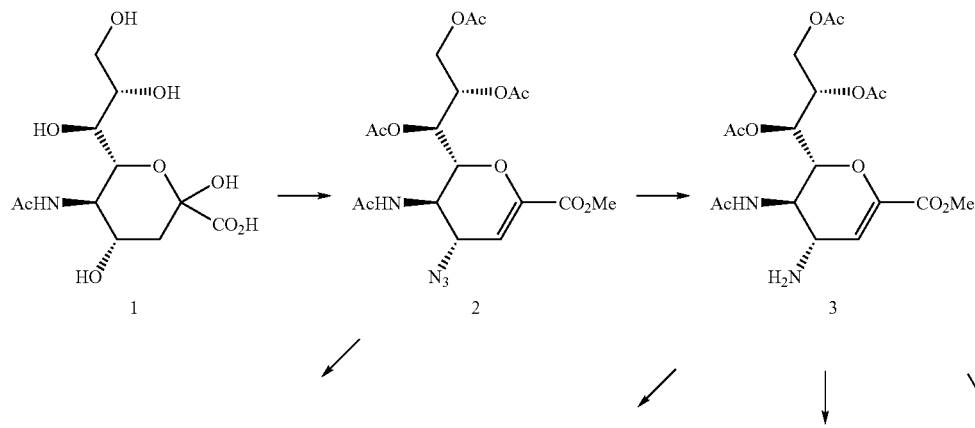

-continued
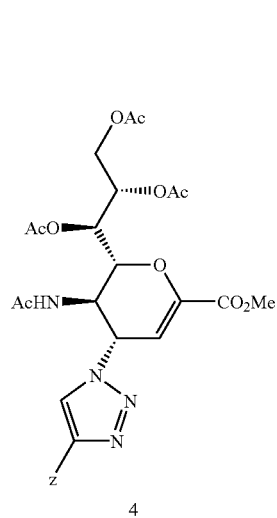
4
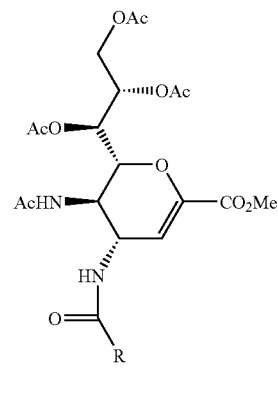
5
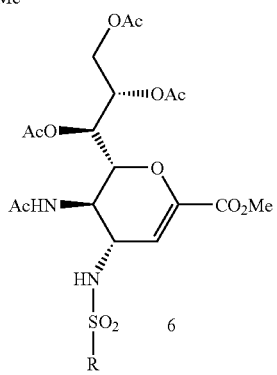
6
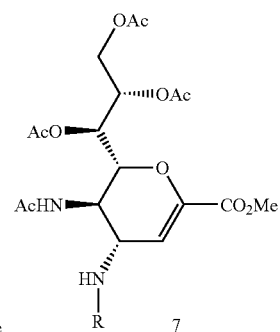
7
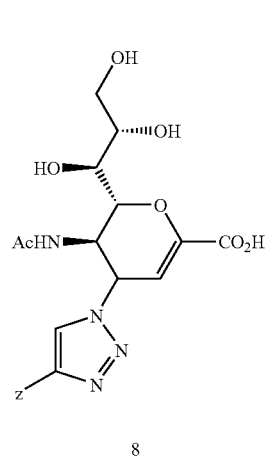
8
z = COOH, H
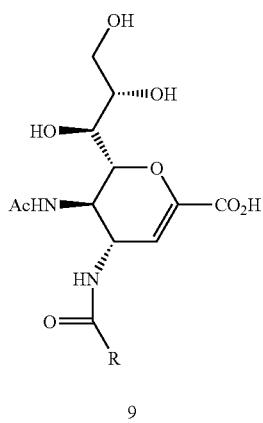
9
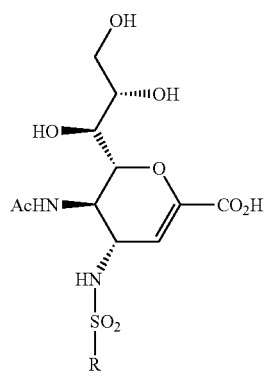
10
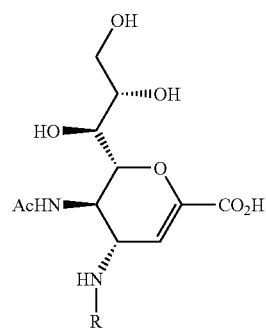
11

Scheme 2
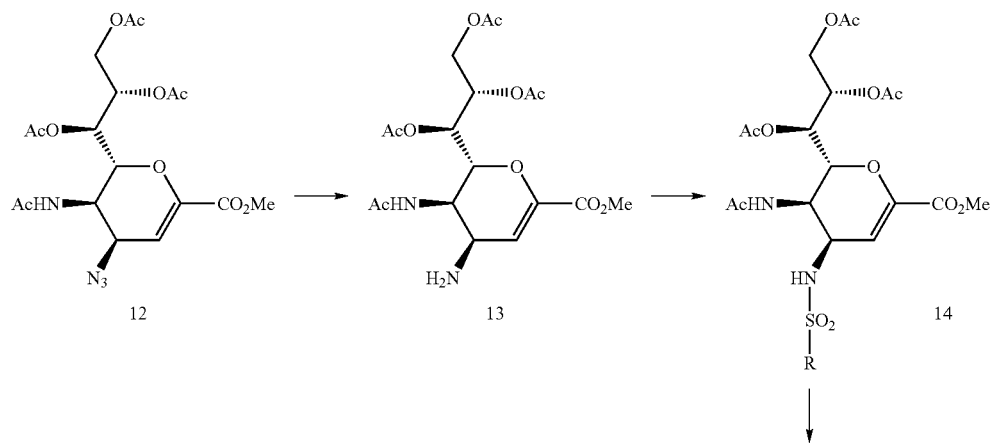
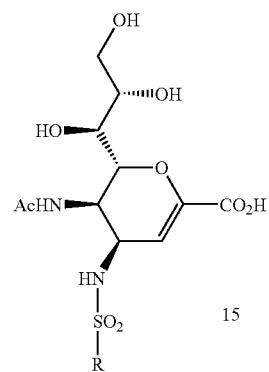
Scheme 3
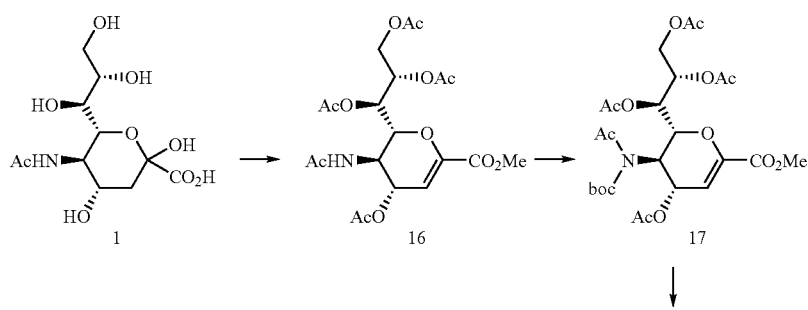

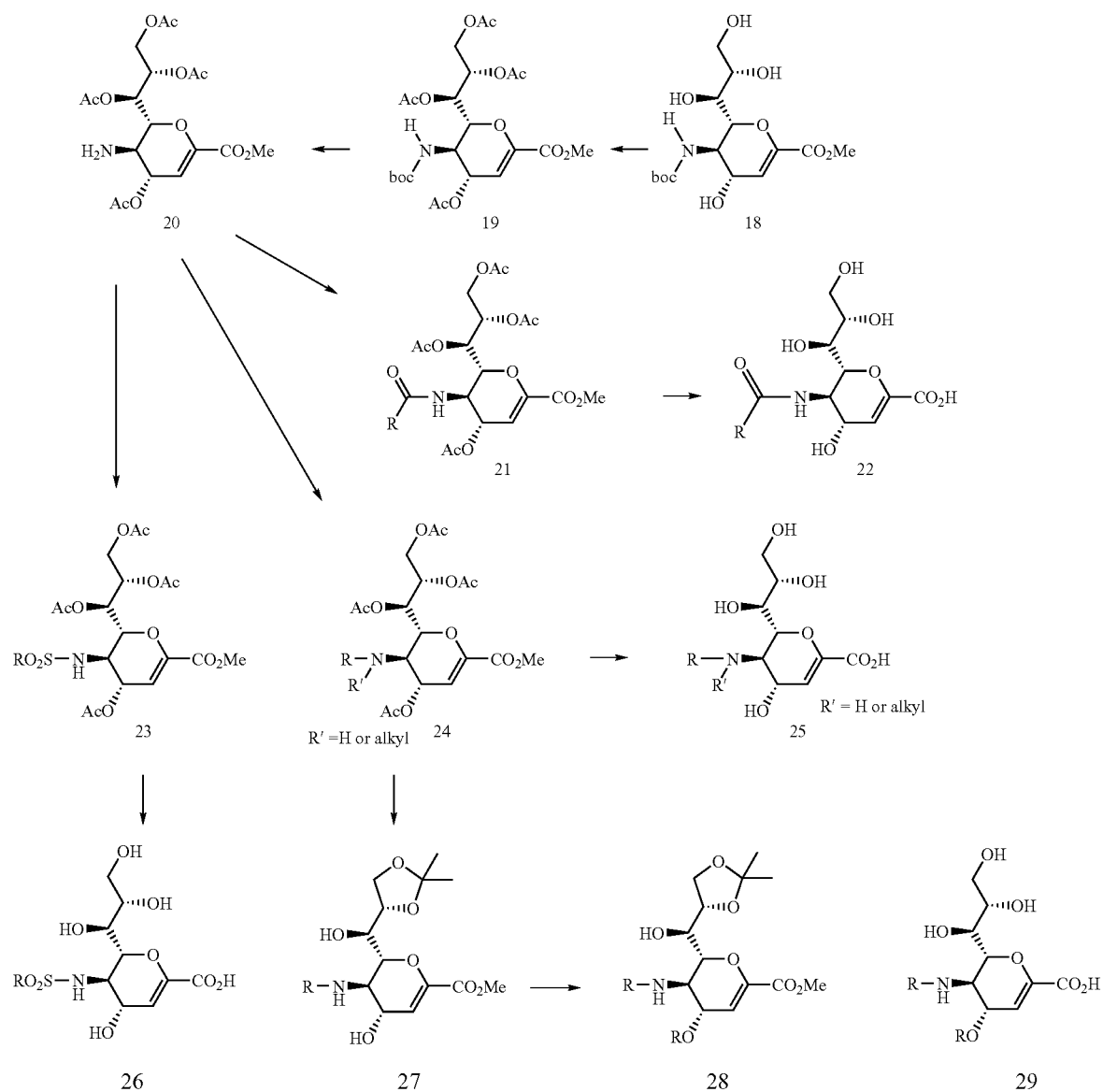
Scheme 4
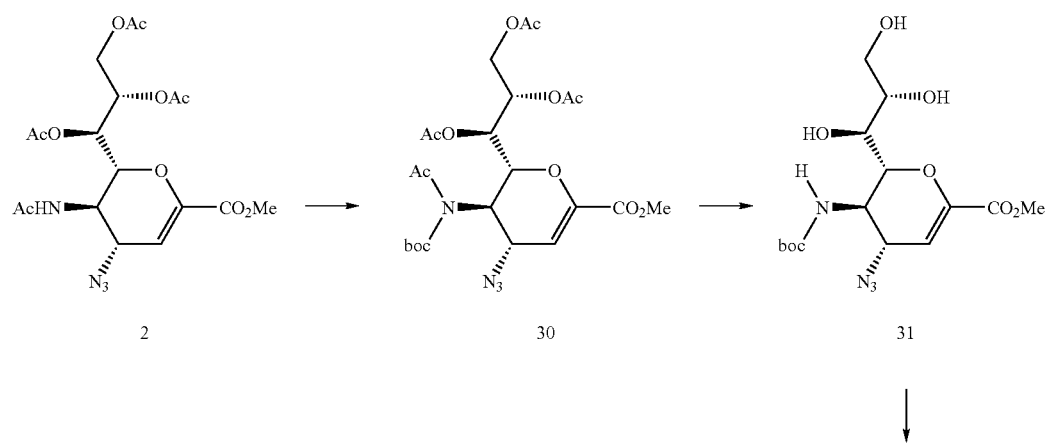

-continued
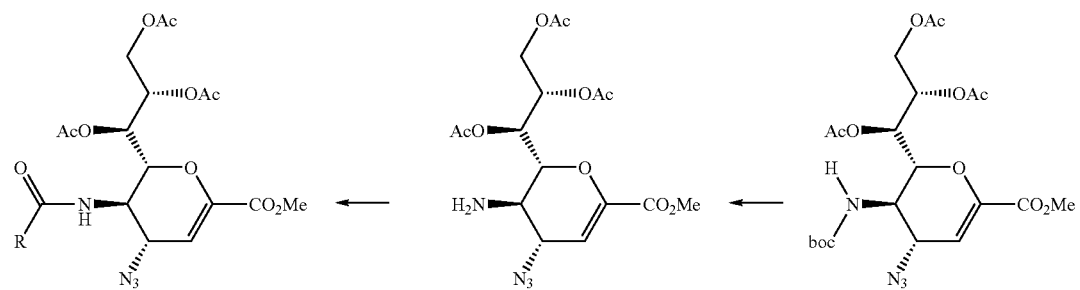
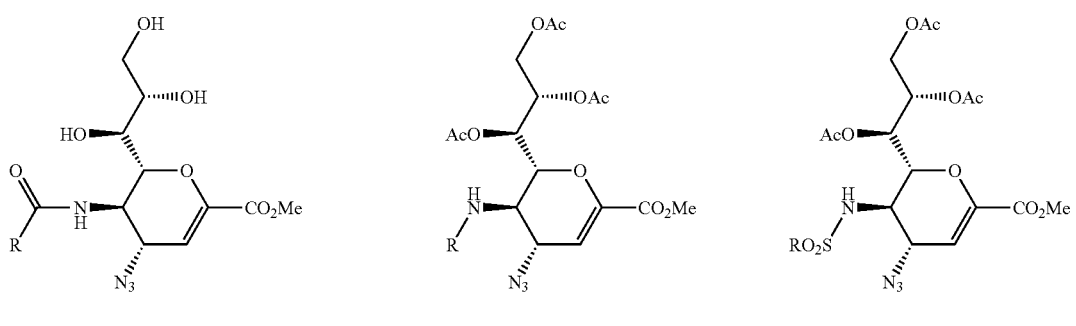
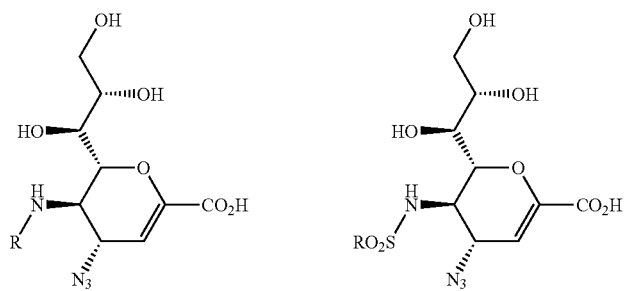

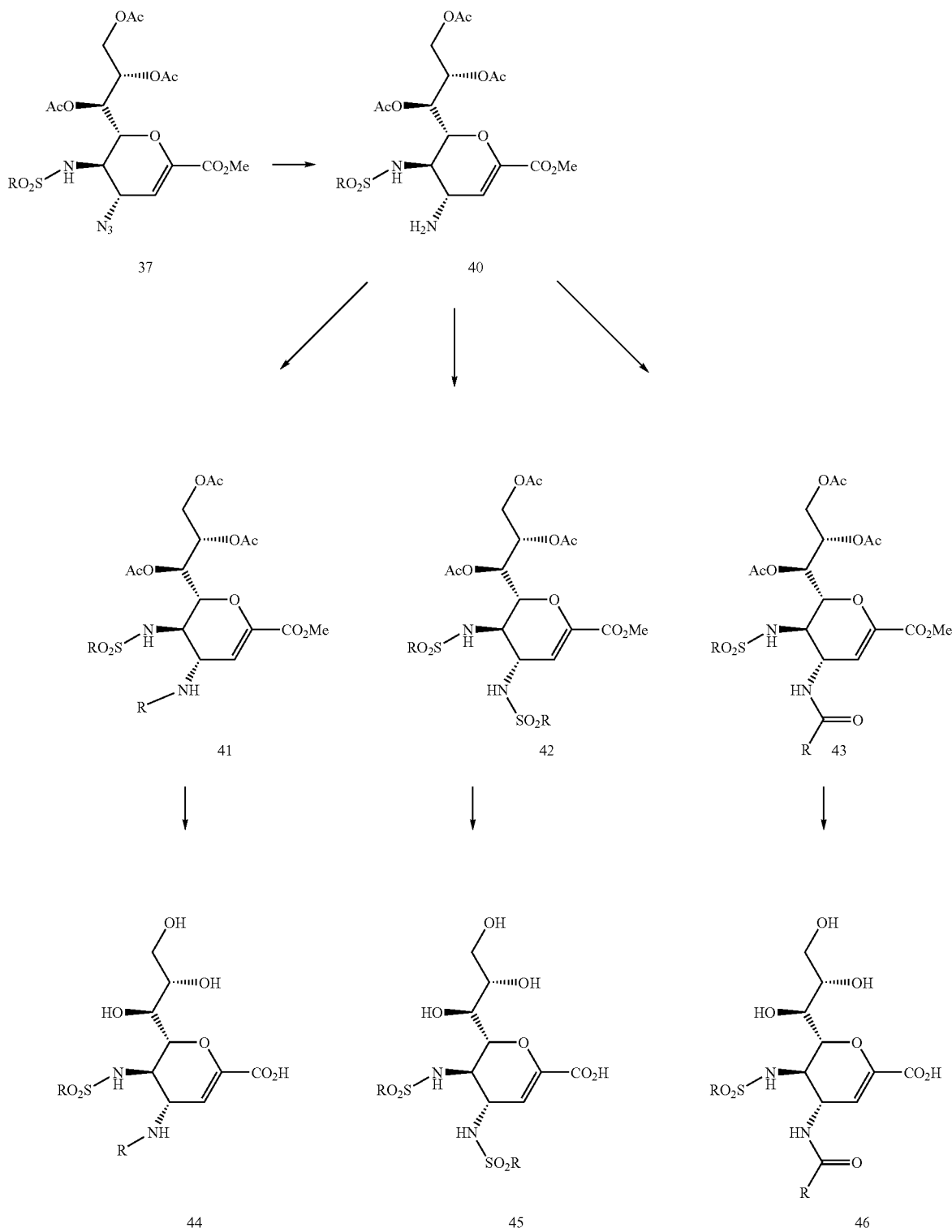

Scheme 6
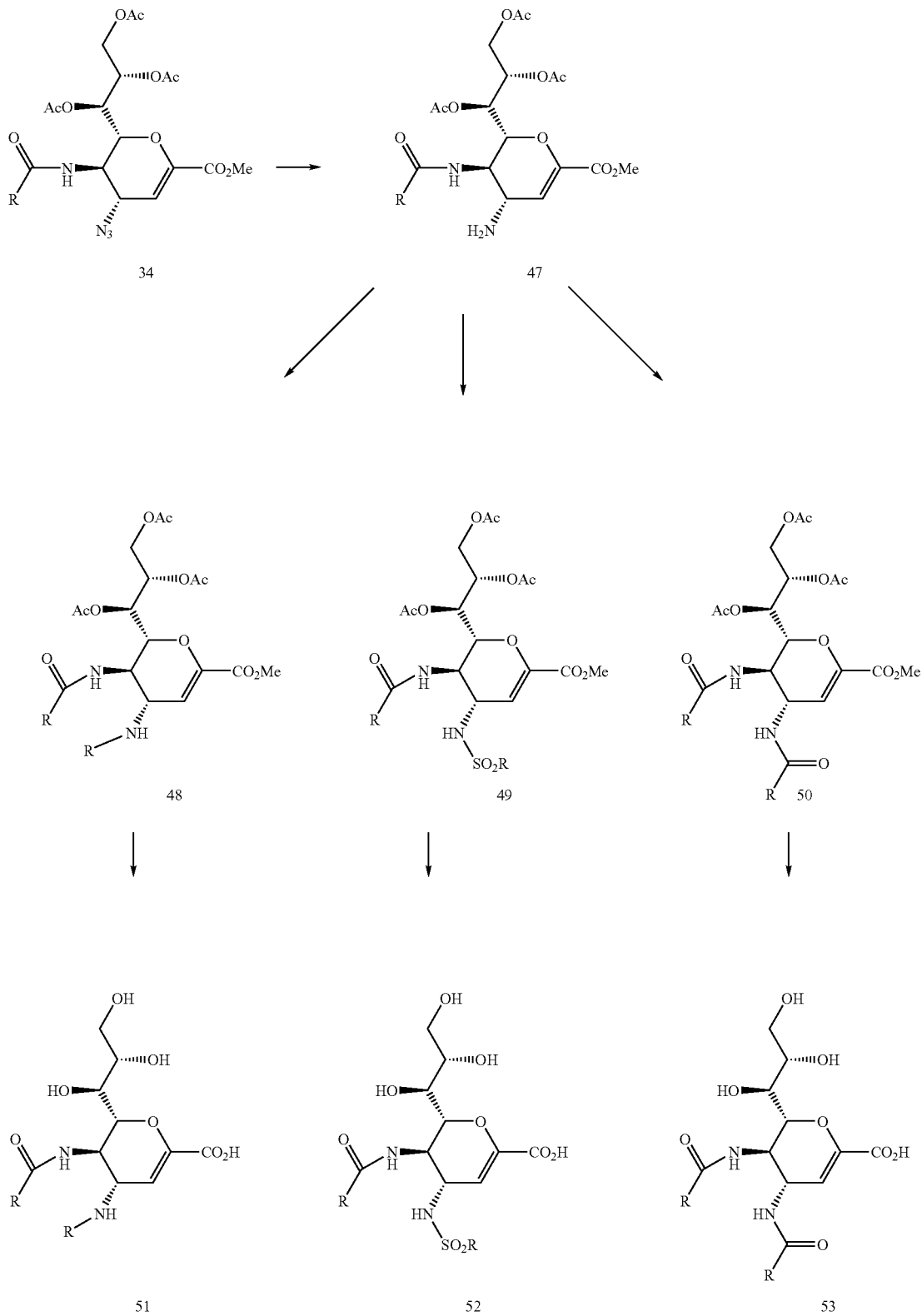

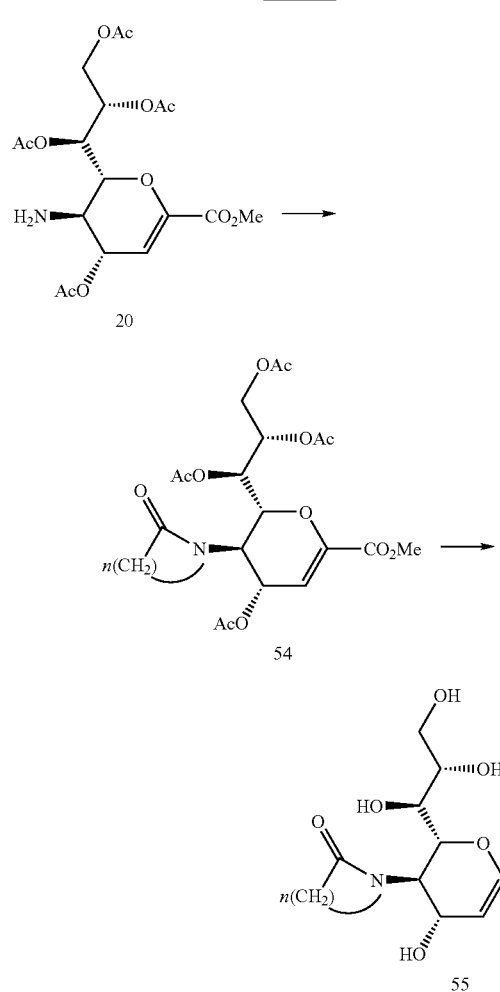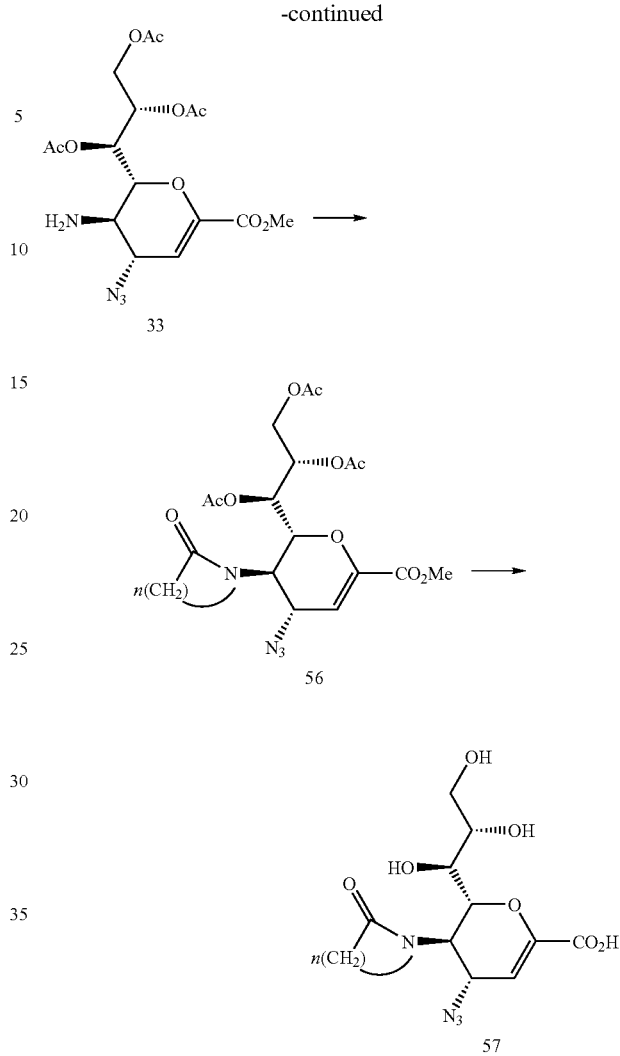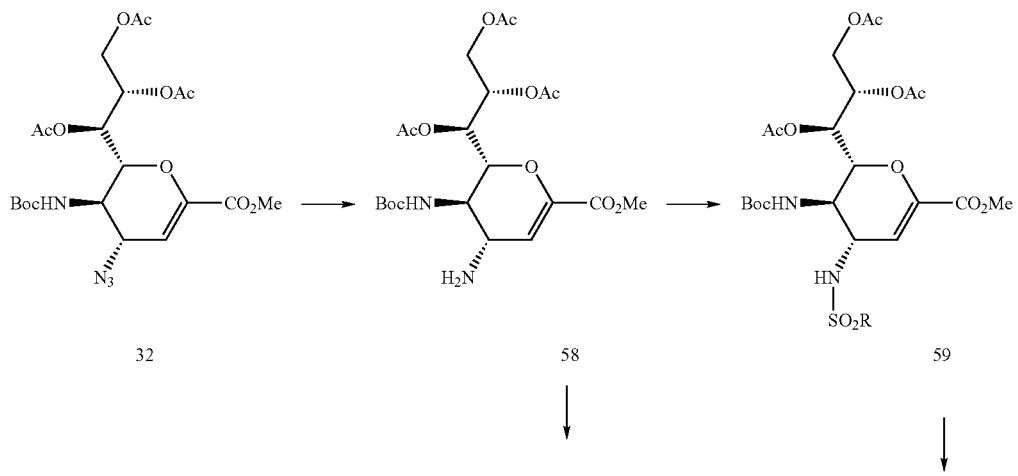

29
30
-continued
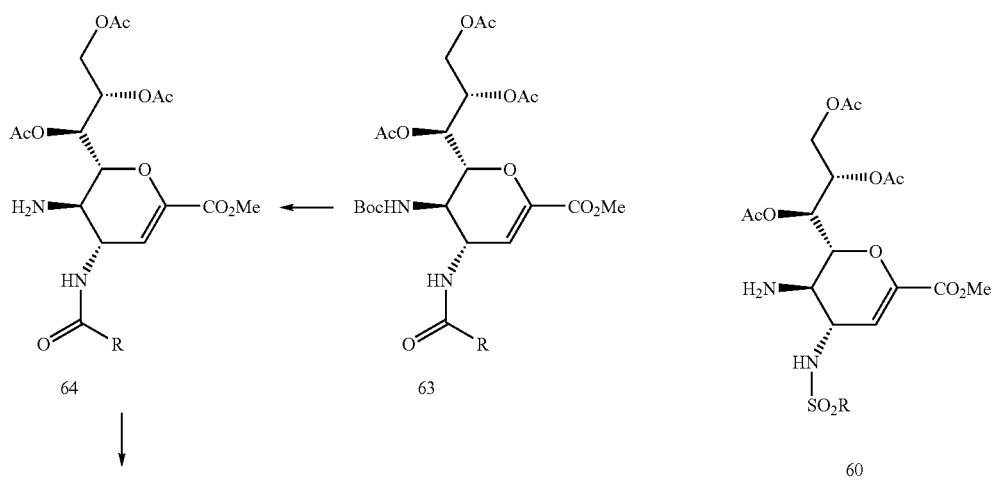
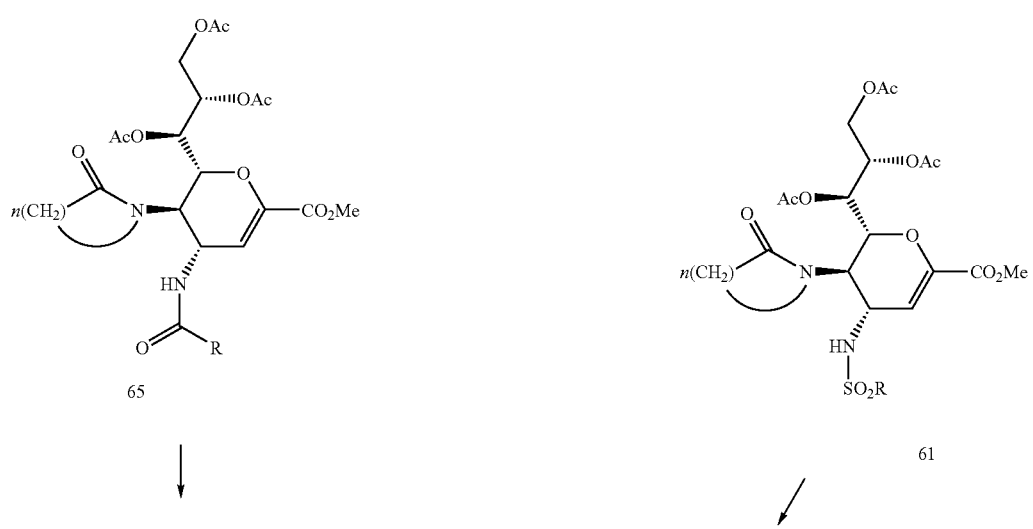
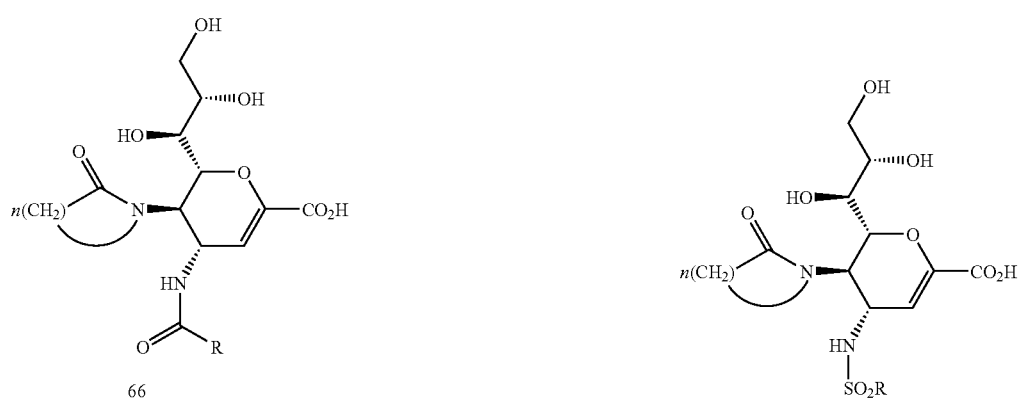

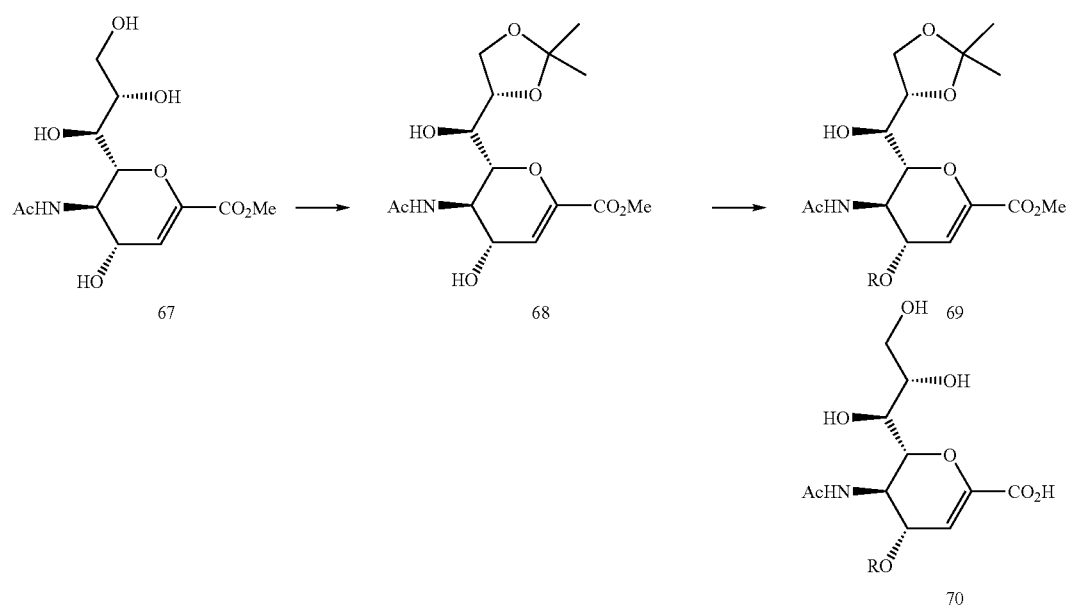
Scheme 9
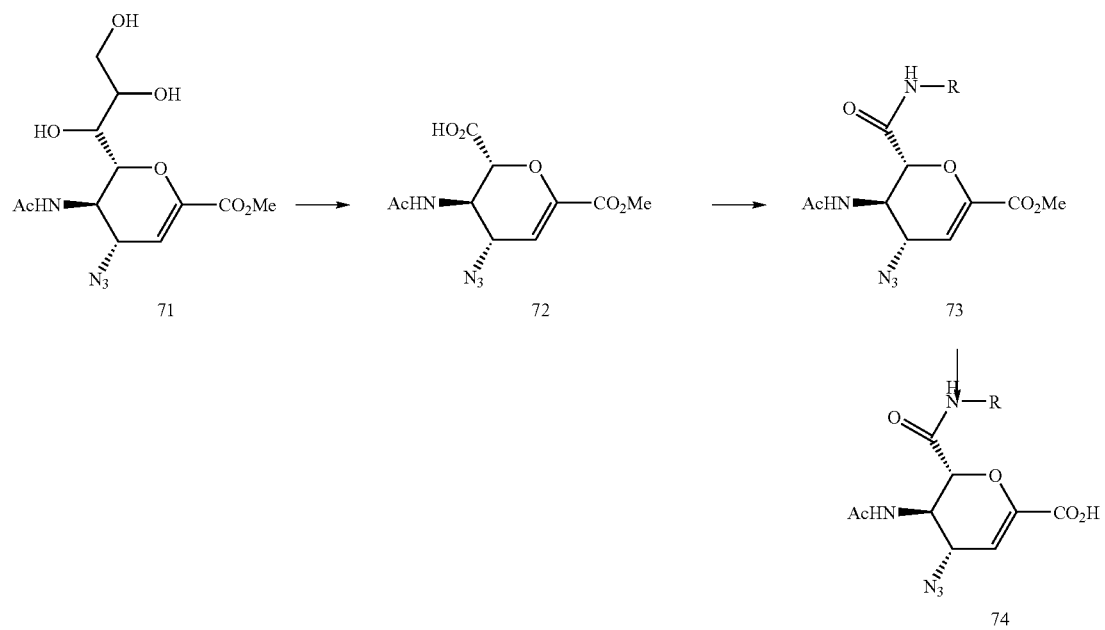
Scheme 10
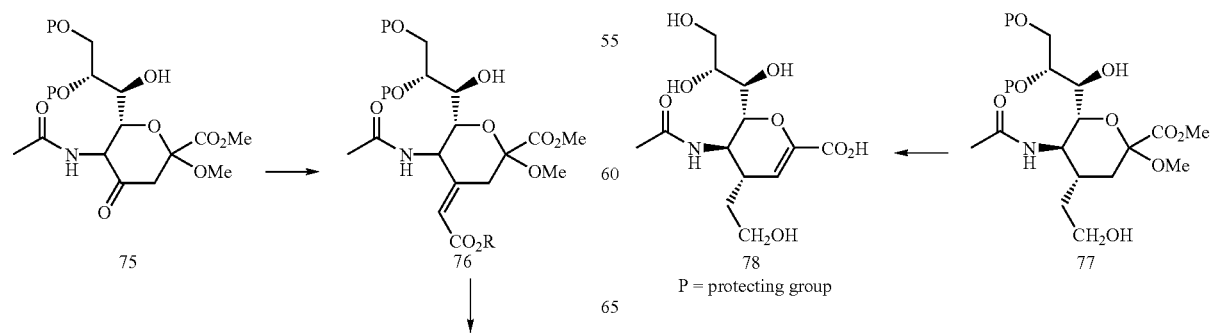
Scheme 11
P = protecting group

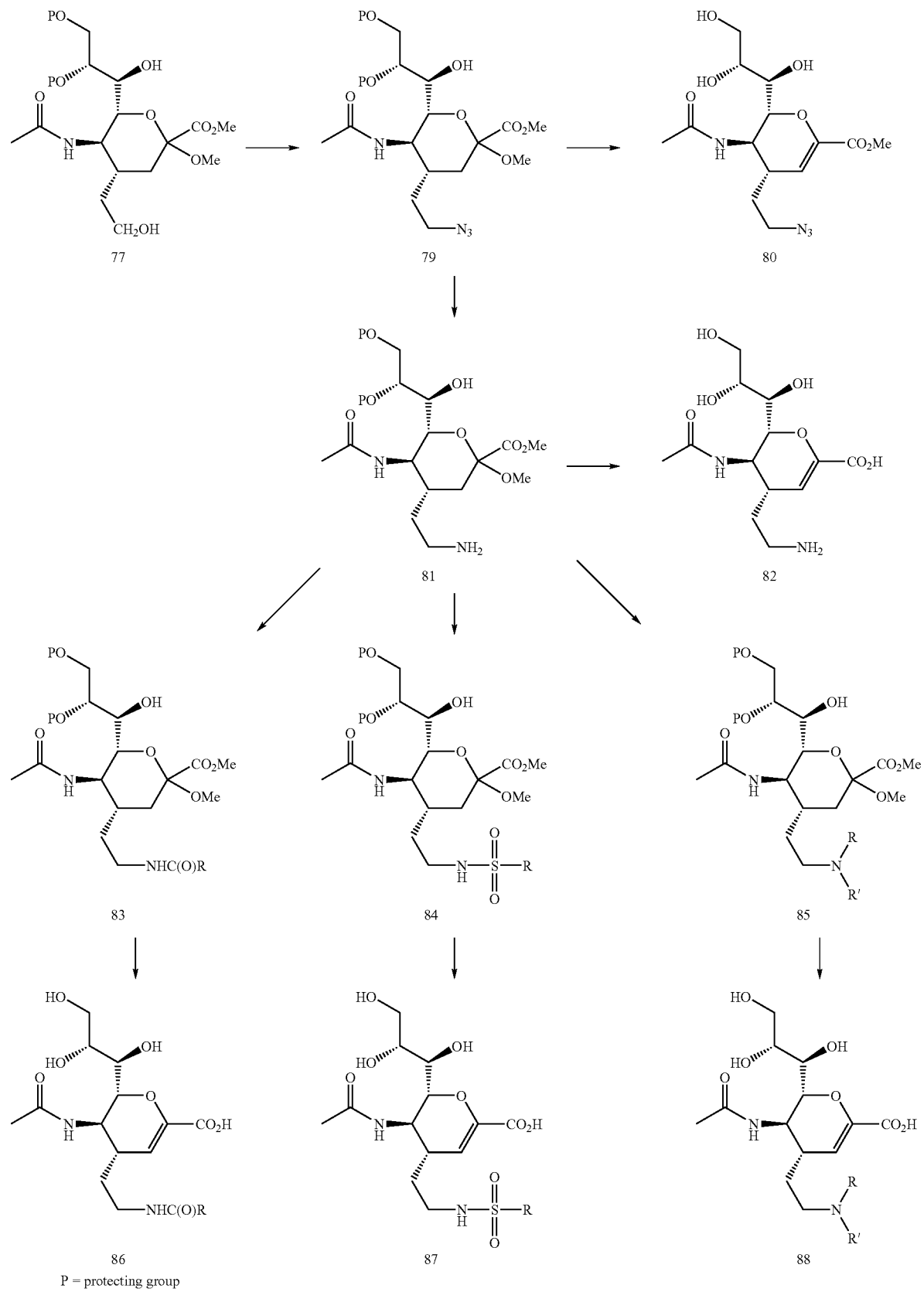
Scheme 12
P = protecting group

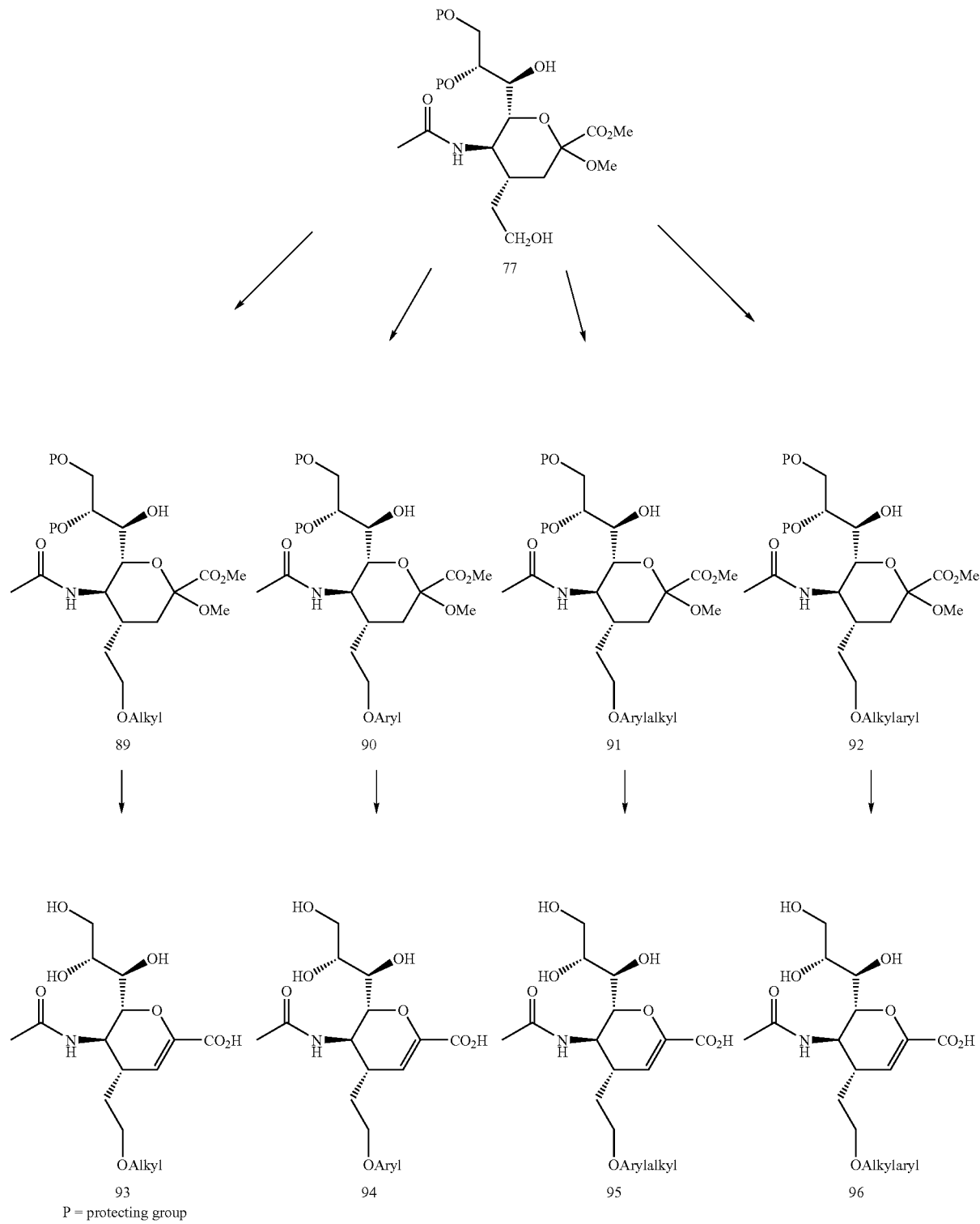

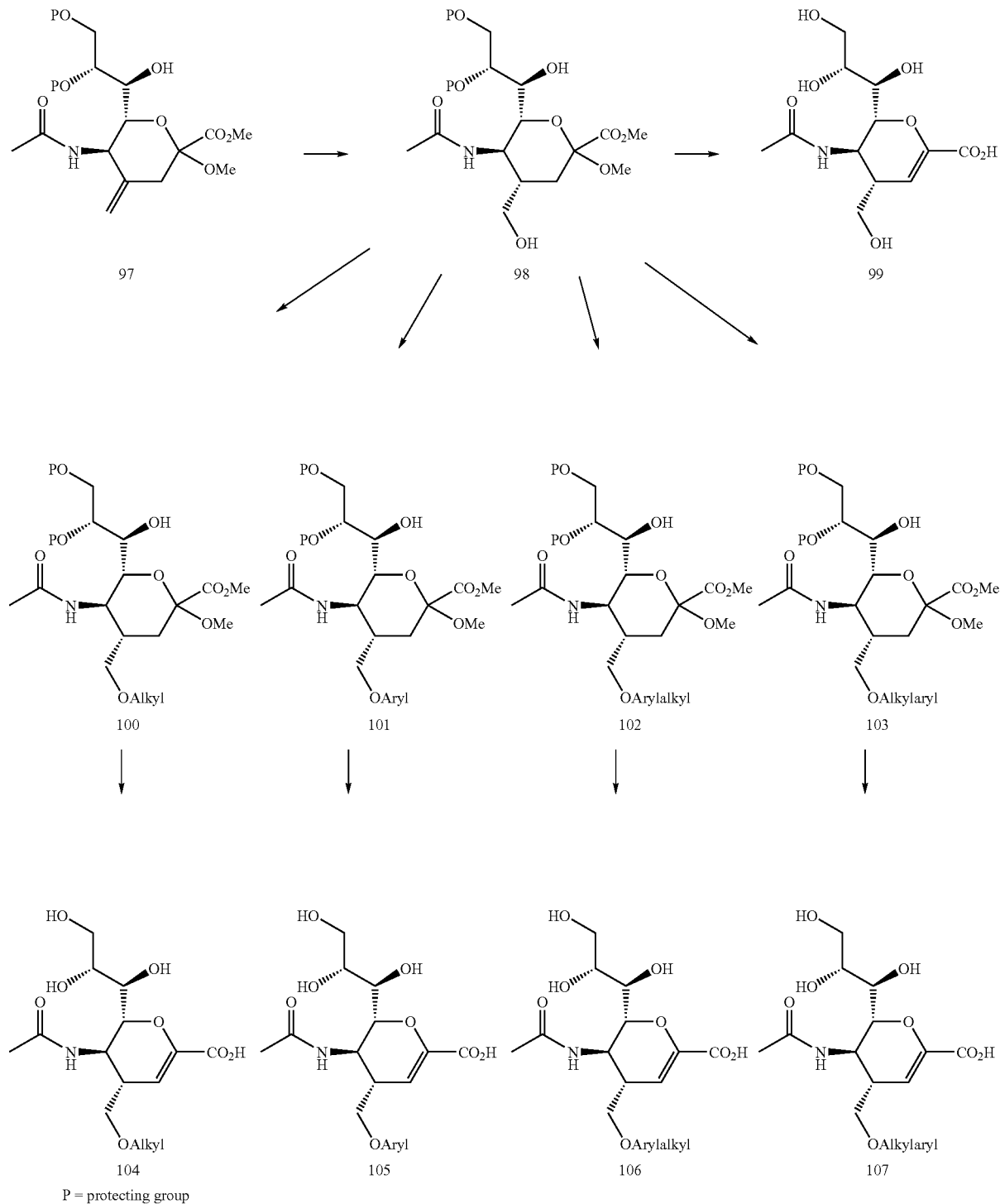
Scheme 14
P = protecting group

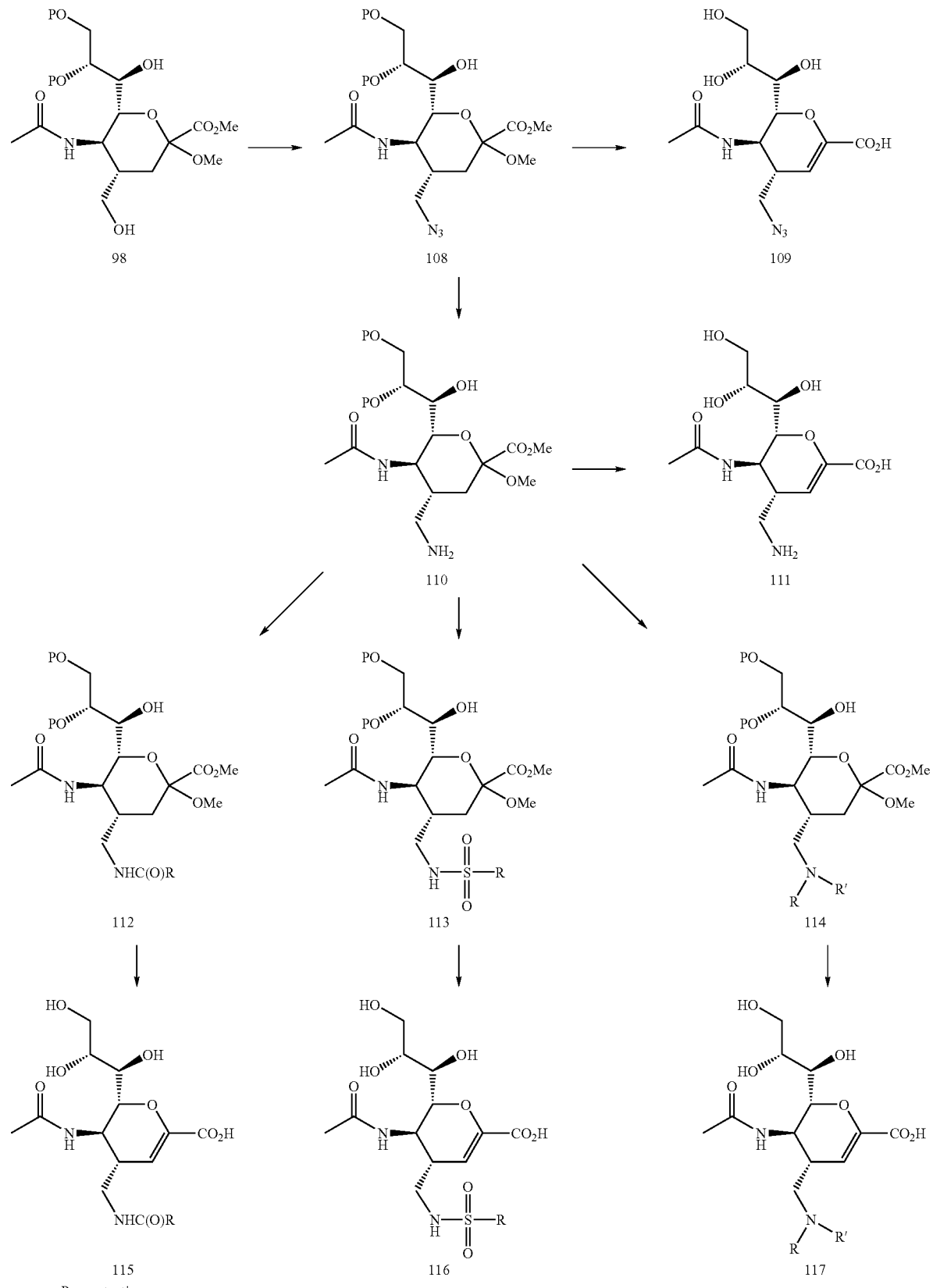

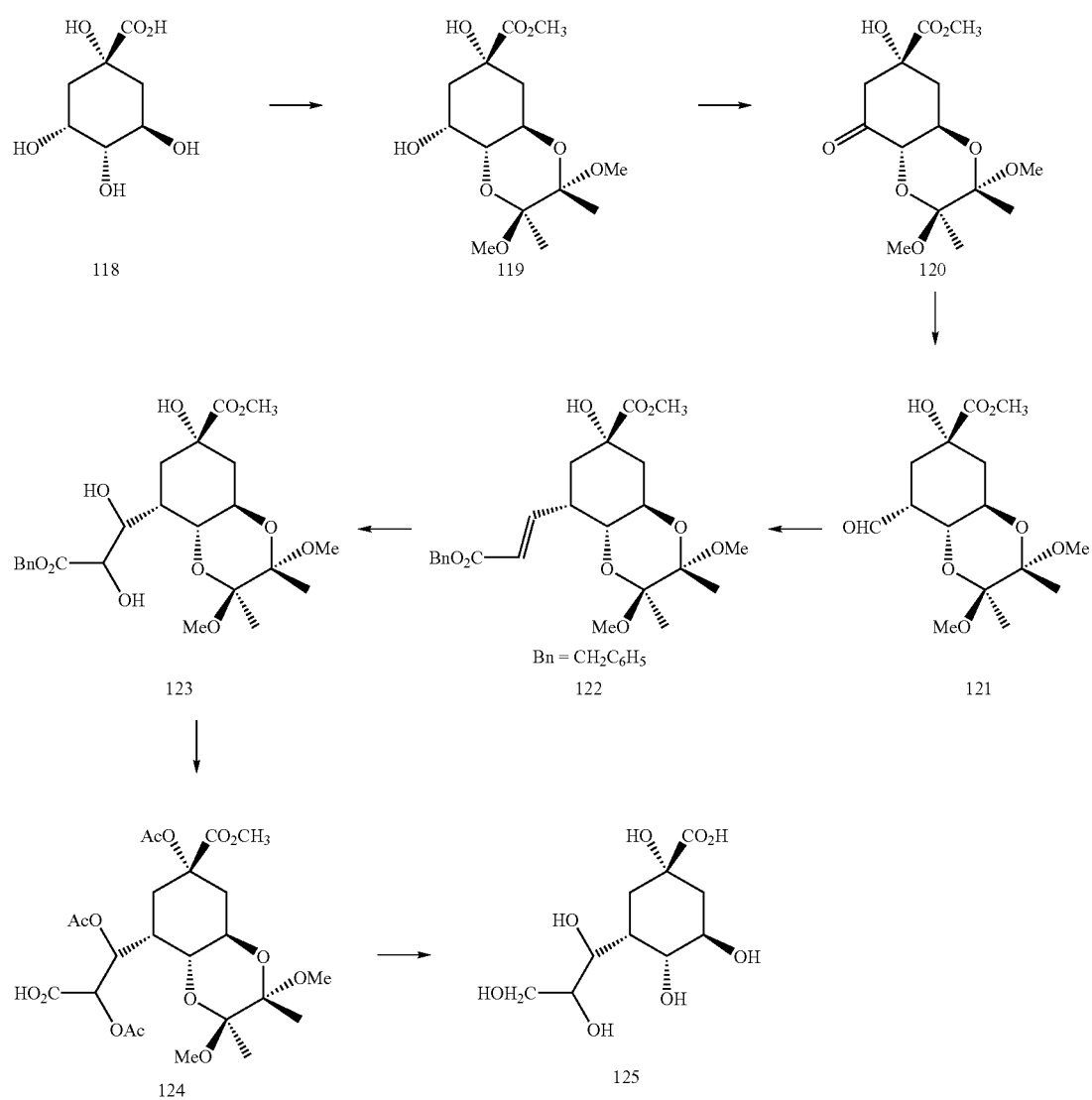
Scheme 16
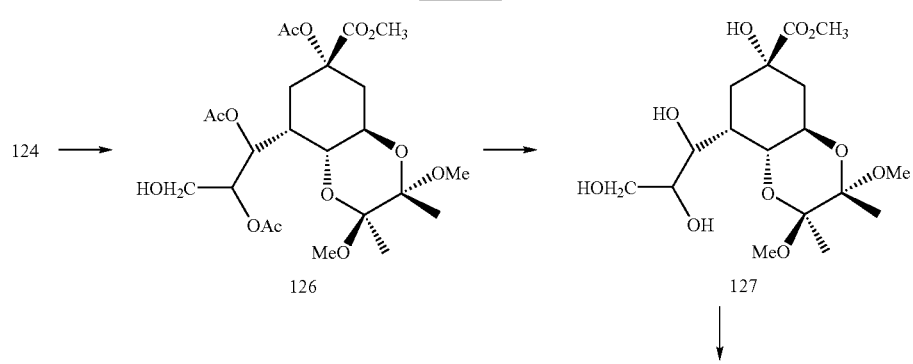
Scheme 17

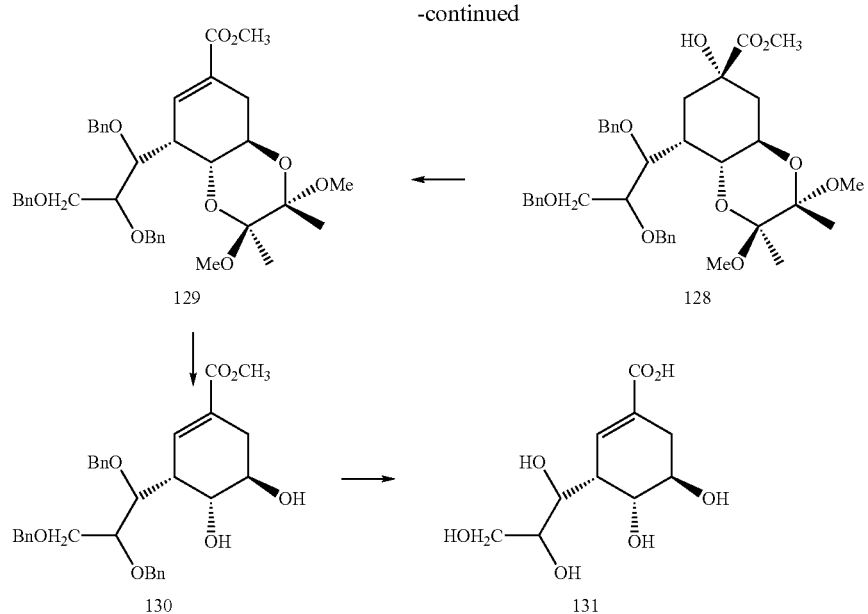
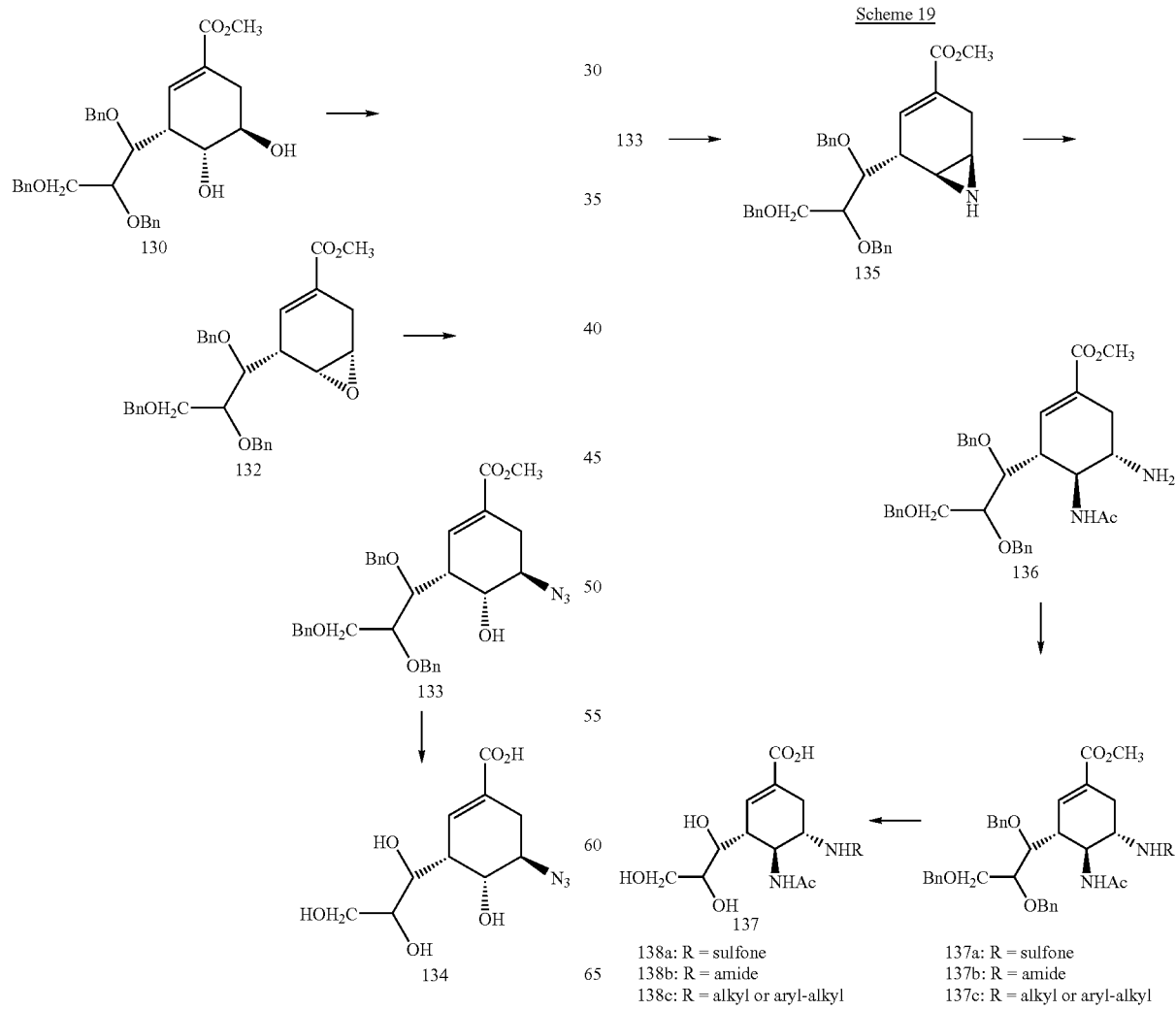
Scheme 18
Scheme 19

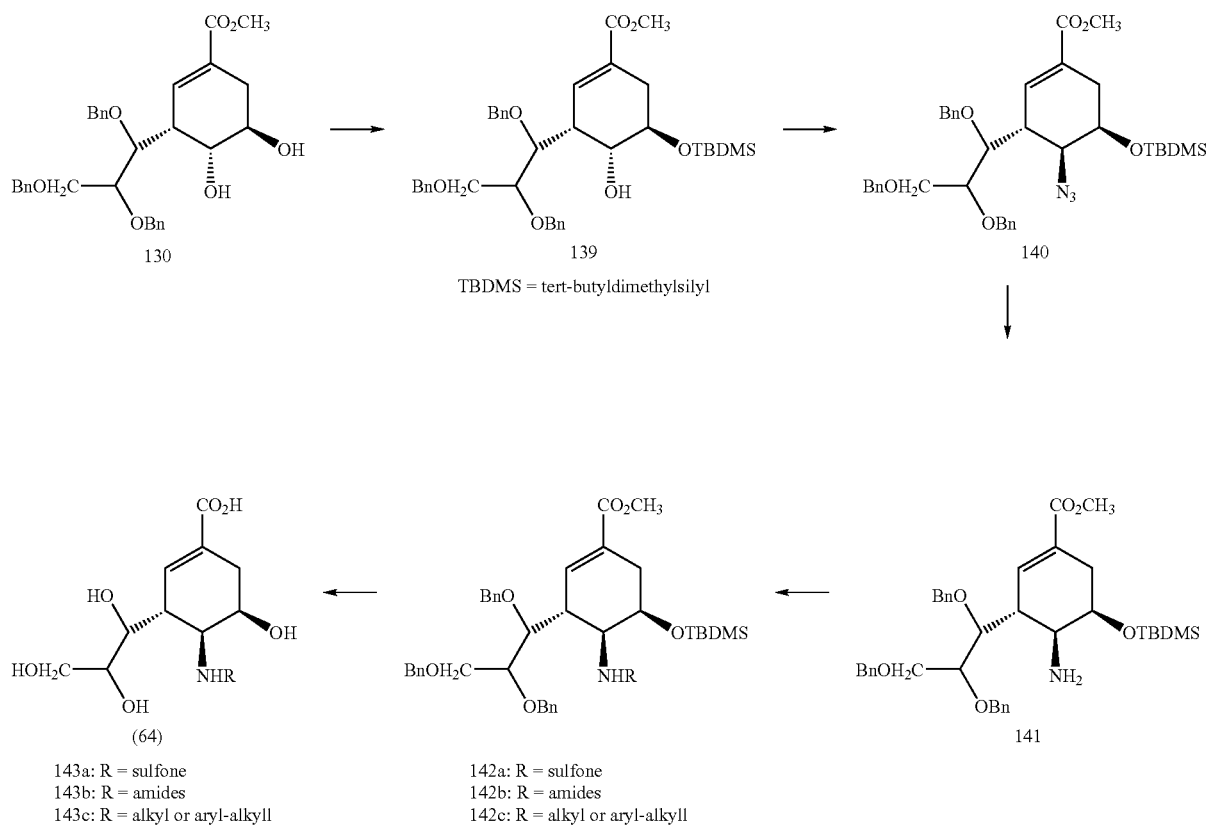
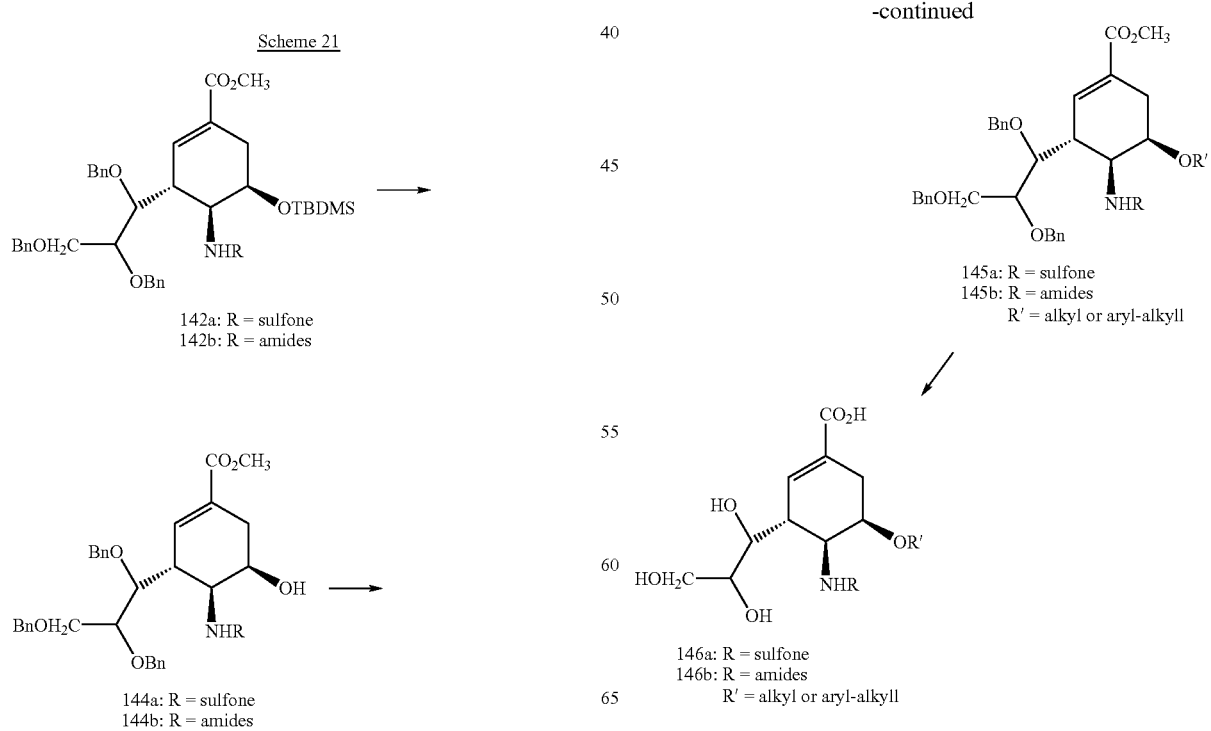

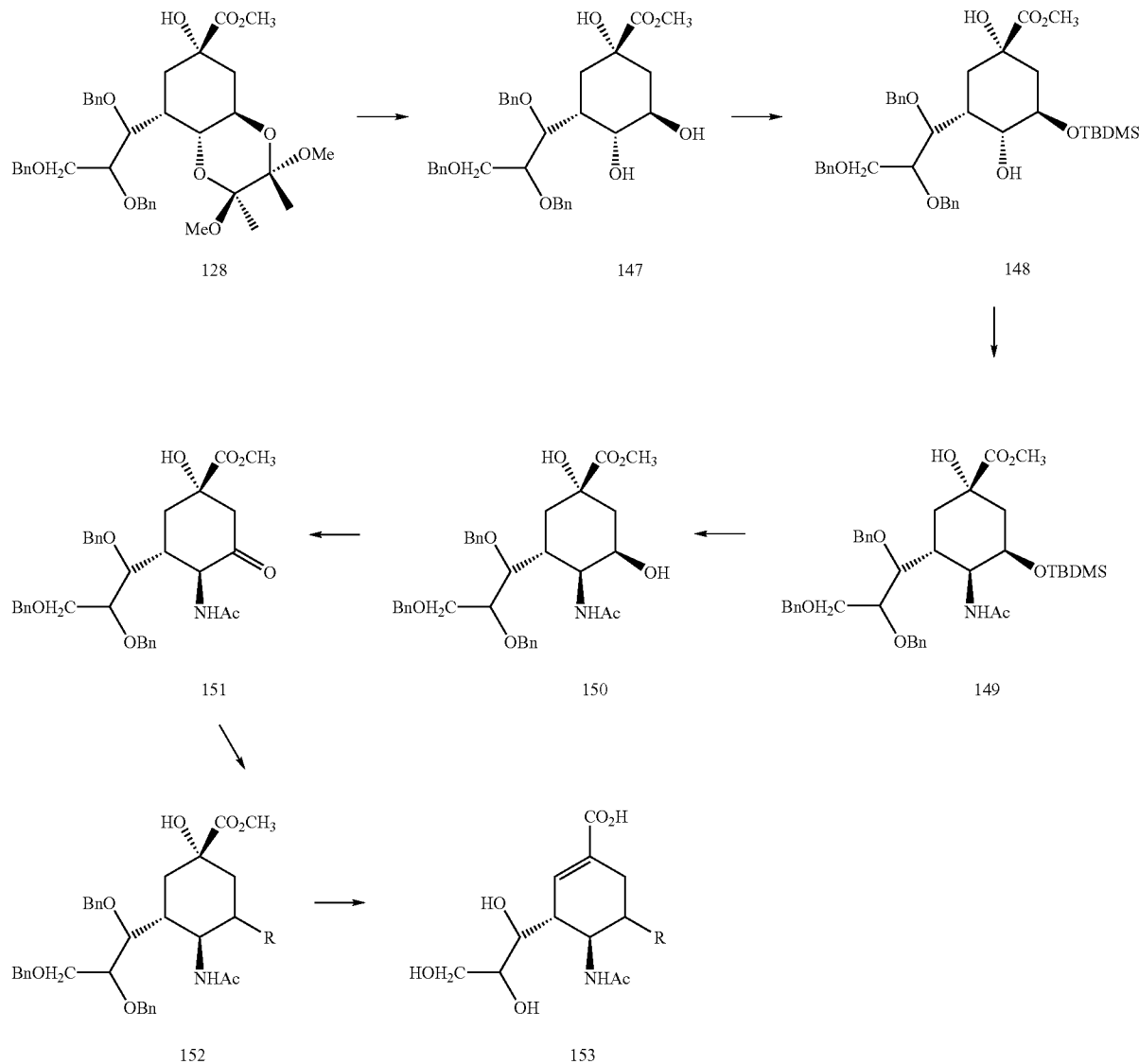
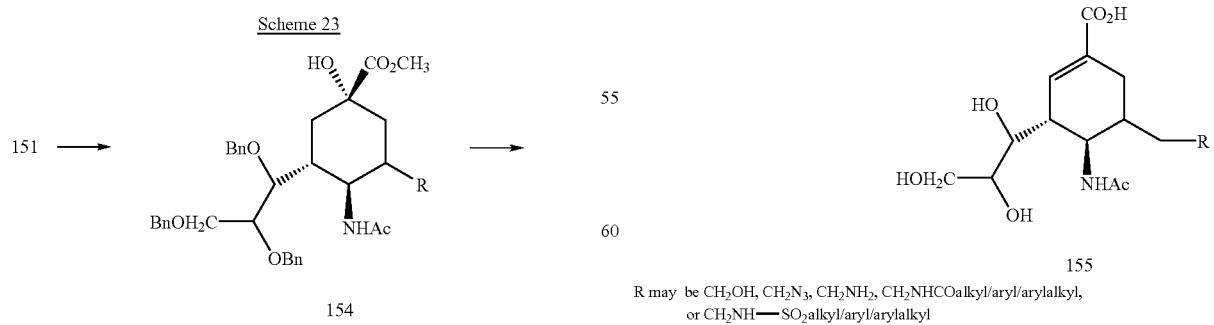

DESCRIPTION OF THE SCHEMES

Scheme-1:

N-Acetylneuraminic acid 1 is converted to azide 2 and amine 3 by literature procedures (Chandler et al., J. Chem Soc. Perk. Trans. 1, 1995, p. 1173). Compound 2 is treated with phenyl vinyl sulfoxide or methyl propiolate to give compound 4 (Z=H or COOH). Compound 3 is converted to: a) 5 with corresponding acid chloride, acid anhydride or acid, b) 6 with appropriate sulfonyl chloride, sulfonic anhydride or sulfonic acid and c) 7 with appropriate alkyl, or aryl halide or any other leaving group attached to alkyl or aryl group. Compounds 4, 5, 6, and 7 are hydrolyzed with base to give the targets 8, 9, 10 and 11, respectively.

Scheme-2:

Compound 12 is prepared according to literature procedures (Schreiner et al., Liebigs Ann. Chem., 1991, p. 129–134), and reduced to compound 13. Compound 13 is converted to 14 with appropriate sulfonyl chloride, sulfonic anhydride or sulfonic acid. Compound 14 is hydrolyzed with base to give the target 15.

Scheme-3:

N-Acetylneuraminic acid 1 is converted to 16 through peracetylation and treating the acetate with acetyl chloride and a mild base, for example, pyridine. Compound 16 is reacted with di tert-butyl dicarbonate (Boc anhydride) in an appropriate solvent using some catalyst, for example dimethylamino pyridine to give 17. The treatment of 17 with catalytic amount of methoxide in methanol gives 18, which is further reacted with acetic anhydride in pyridine to give acetylated product 19. Deprotection of Boc group in 19 is achieved by acid treatment, for example trifluoroacetic acid in dichloromethane to give 20. Compound 20 is further reacted with a) sulfonyl chloride, sulfonic anhydride, or sulfonic acid to give 23, b) appropriate alkyl or aryl halide or any other leaving group attached to alkyl or aryl group to give 24 and c) acid chloride, acid anhydride or acid to give 21. Compound 24 is deacylated then protected on $8^{th}$ and $9^{th}$ hydroxyl groups with isopropylidene group by the reaction of 2,2-dimethoxypropane, acetone and $H^+$ to give 27. Compound 27 is converted to 28 through treatment with hydride source for example sodium hydride followed by treatment with appropriate alkyl or aryl halide. Compounds 21, 23, 24, and 28 are hydrolyzed to the corresponding targets 22, 25, 26, and 29, respectively.

Scheme-4:

Azido compound 2 from Scheme-1 is reacted with di tert-butyl dicarbonate in an appropriate solvent using some catalyst, for example dimethylamino pyridine to give 30. The treatment of 30 with catalytic amount of methoxide in methanol gives 31, which is further reacted with acetic anhydride in pyridine to give acetylated product 32. Deprotection of Boc group in 32 is achieved by acid treatment, for example trifluoroacetic acid in dichloromethane to give 33. Compound 33 is further reacted with a) sulfonyl chloride, sulfonic anhydride, or sulfonic acid to give 37, b) appropriate alkyl or aryl halide or any other leaving group attached to alkyl or aryl group to give 36 and c) acid chloride, acid anhydride or acid to give 34. Compounds 34, 36 and 37 are hydrolyzed to the corresponding targets 35, 38 and 39, respectively.

Scheme-5:

Azido compound 37, obtained in scheme 4 is reduced to the corresponding amine 40. Amine 40 is further reacted with a) sulfonyl chloride, sulfonic anhydride, or sulfonic acid to give 42, b) appropriate alkyl or aryl halide or any other leaving group attached to alkyl or aryl group to give 41 and c) acid chloride, acid anhydride or acid to give 43. Compounds 41, 42 and 43 are hydrolyzed to the corresponding targets 44, 45 and 46, respectively.

Scheme-6:

Azido compound 34, obtained in scheme 4 is reduced to the corresponding amine 47. Amine 47 is further reacted with a) sulfonyl chloride, sulfonic anhydride, or sulfonic acid to give 49, b) appropriate alkyl or aryl halide or any other leaving group attached to alkyl or aryl group to give 48 and c) acid chloride, acid anhydride or acid give 50. Compounds 48, 49 and 50 are hydrolyzed to the corresponding targets 51, 52 and 53, respectively.

Scheme-7:

Compound 20 is condensed with 4-bromobutyryl chloride or 3-bromopropionyl chloride to give 54, where, n=3 or 2, respectively. Deprotection of 54 provides the target 55. Like wise 33 also reacts under the same conditions to give the target 57 through 56.

Scheme-8:

The azide 32 is reduced to amine 58. Compound 58 is further reacted with a) sulfonyl chloride, sulfonic anhydride or sulfonic acid to give sulfonamide 59, or b) acid chloride, acid anhydride or acid to give amide 63. The protecting groups of amine 59 and 63 are removed with trifluoroacetic acid or with any other acid to give the corresponding amines, 60 and 64. Further condensation of 60 and 64 with 4-bromobutyryl chloride or 3-bromopropionyl chloride provides 61 and 65, which on deprotection generate the targets, 62 and 66, respectively.

Scheme-9:

The alkylation of $4^{th}$ hydroxyl group in 68 with sodium hydride and using appropriate alkyl or arylalkyl halide provides ether 69. Hydrolysis of protecting groups of 69 gives the target 70.

Scheme-10:

Compound 71 is treated with sodium periodate to give aldehyde which is further oxidized to give compound 72. Compound 72 is treated with different amines to give compound 73. Hydrolysis of protecting groups of 73 gives the target 74.

Scheme-11:

Compound 75 prepared from the literature procedures (Groves et al., J. Chem. Soc., Perkin Trans. 1, 1996, p. 2817) undergoes Wittig reaction with $Ph_3P=CHCO_2CH_2C_6H_5$ to give 76. Ester on hydrogenolysis and reduction produces compound 77. The target 78 is obtained from 77 through hydrolysis of protecting groups; acetylation, reaction with trimethylsilyl triflate (TMS-triflate) and base hydrolysis.

Scheme-12:

Primary hydroxyl group of 77 at C-4 position is converted to azide 79 by Mitsunobu reaction or by the reaction of methanesulfonyl chloride and sodium azide. Azide 79 is reduced to give amine 81, and further reactions of amine to generate amides 83, sulfonamides 84 and alkyl or arylalkyl amines 85 are the same as described in Scheme-1. The targets 80, 82, 86, 87, and 88 with double bond are produced from 79, 81, 83, 84 and 85, respectively following the same methods as described in Scheme-11.

Scheme-13:

Compound 77 reacts with sodium hydride or any other base followed by the reaction with: a) alkyl halide to give alkyl ether 89, and b) arylalkyl halide to give 92. Compounds 90 and 91 are prepared by the reaction of mesylate or triflate of 77 with aryl halide or alkylaryl halide or triflate after generating a nucleophile. Further deprotection, acetylation and TMS-triflate reactions of 89, 90, 91 and 92, produce the targets, 93, 94, 95 and 96, respectively.

Scheme-14:

Compound 97 produced by the literature methods (Groves et al., J. Chem. Soc., Perkin Trans. 1, 1996, p. 2817) is converted to hydroxymethyl compound 98 through hydroboration and base treatment. Corresponding alcohol ethers, 100, 101, 102 and 103 are obtained from 98 as described in scheme 13 and the targets, 99, 104, 105, 106 and 107 are prepared using the same methods as given in Scheme-13 from the corresponding compounds, 98, 100, 101, 102, and 103, respectively.

Scheme-15:

Hydroxy methyl compound 98 is converted to azido methyl 108, which is further reduced to amine 110. The formation of amides 112, sulfonamides 113, alkyl or arylalkyl amines 114 and the unsaturated compounds 109, 111, 115, 116 and 117 is carried the same way as described in Schemes 1 and 12.

Scheme-16:

Quinic acid (118) is converted to 119 by literature procedures (Frost et al., J. Org. Chem., 61, 1996, p. 3897). Secondary hydroxyl group is oxidized to a keto group by standard oxidative methods, such as pyridinium chlorochromate (PCC) or Swern oxidation to give 120. Homologation of keto compound 120 with 1,3-dithiane or bis phenylthiomethane followed by hydrolysis of thio group produces 121. The Wittig reaction of 121 with $Ph_3P=C-CO_2Bn$ (Bn=benzyl) gives 122. Dihydroxylation of 122 through epoxidation or $OsO_4$ catalyzed reaction produces 123, which on debenzylation (catalytic hydrogenation) gives compound 124. Deprotection of 124 gives the target 125.

Scheme-17:

Acid group of compound 124 from Scheme-19 is reduced to alcohol 126, and deacetylation of 126 with methoxide in methanol produces 127. Secondary and primary hydroxyl groups are protected with benzyl group by the reaction of base and benzyl halide to give 128. The reaction of 128 with sulfuryl chloride followed by base, results into a double bond compound 129. Deprotection of hydroxyls and the ester produces the target 131.

Scheme-18:

Compound 130 from Scheme-17 is reacted with triphenylphosphine and diethylazo dicarboxylate (DEAD) to give an epoxide 132, which is opened with sodium azide to produce 133 which is further deprotected to generate the target 134.

Scheme-19:

Compound 133 from Scheme 18 is converted to aziridine 135 through mesylation, and triphenylphosphine reaction. Aziridine 135 is opened with sodium azide, amino group is acetylated and azido is reduced to amine to give 136. Amino group of 136 is manipulated to produce, a) sulfonamides 137a by the reaction of corresponding sulphonyl halides, sulfonic anhydrides or sulfonic acids; b) amides 137b by the reaction of corresponding acid halides, acid anhydrides or acids, or c) alkyl or arylalkyl amines 137c by the reaction of corresponding alkyl or arylalkyl halides. Compounds 137a, 137b, and 137c are deprotected to give targets 138a, 138b and 138c.

Scheme-20:

Compound 130 from Scheme-17 is reacted with 1 equivalent of tert-butyl dimethylsilyl chloride and a base, imidazole, to give 139. The free hydroxyl group of 139 is converted to azido 140 through Mitsunobu reaction (triphenylphosphine, diethyl azo dicarboxylate and hydrazoic acid); azido is reduced to amino 141. Amino group of 141 is manipulated to produce, a) sulfonamides, 142a by the reaction of corresponding sulphonyl halides, sulfonic anhydrides or sulfonic acids, b) amides 142b, by the reaction of corresponding acid halides, acid anhydrides or acids, or c) alkyl or arylalkyl amines, 142c by the reaction of corresponding alkyl or arylalkyl halides. Compounds 142a–c are deprotected to give targets 143a–c.

Scheme-21:

Compound 142a (sulfonamides) and 142b (amides) from scheme-20 are reacted with an acid (HCl) or tetrabutylammonium fluoride to give hydroxy compound 144a and 144b, which are further reacted with sodium hydride followed by alkyl or arylalkyl halides to produce ethers 145a and 145b. Further deprotection of 145a and 145b produces the targets 146a and 146b.

Scheme-22:

Compound 128 is partially deprotected to give 147. The reaction of 147 with 1 equivalent of tert-butyl dimethylsilyl chloride and imidazole protects one hydroxyl to give 148. Hydroxyl is converted to acetylamino group as described in Scheme 20. The deprotection of tert-butyl dimethylsilyl and further oxidation of the resultant hydroxyl produces compound 151. Compound 151 is converted to the compounds of type 152 according to the methods described in schemes-14 and 15. The double bond formation in 152 by the reaction of sulfuryl chloride and base, followed by deprotection affords the targets 153.

Scheme-23:

Compound 151 is converted to the compounds of the type 154 according to the methods given in schemes-11, 12 and 13. The double bond formation in 154 by the reaction of sulfuryl chloride and base, followed by deprotection affords the targets 155.

GENERAL METHODS

Method A:

To a mixture of methyl 5-acetamido-7,8,9-tri-O-acetyl-4-amino-2,3-didehydro-2,3,4,5-tetradeoxy-D-glycero-D-galacto-2-nonulopyranosidonate (ref: Chandler et al., J. Chem Soc. Perk. Trans. 1, 1995, p. 1173) (1 mmol) in methylene chloride (10 mL) was added appropriate acid halide, acid anhydride, sulfonyl halide, sulfonic anhydride or sulfonic acid (1.5 mmol) and triethylamine (1.5 mmol). The mixture was stirred at room temperature for 16 h. The reaction mixture was concentrated to dryness and the residue was purified by silica gel chromatography. The appropriate fractions were collected and concentrated to dryness.

To the residue (1 mmol) was added 0.5N sodium hydroxide (10 mL) and the mixture was stirred at room temperature for 4 h, neutralized with HCl, filtered through a plug of cotton to give the desired compounds.

Method B:

To a mixture of methyl 5-acetamido-7,8,9-tri-O-acetyl-4-amino-2,3-didehydro-2,3,4,5-tetradeoxy-D-glycero-D-galacto-2-nonulopyranosidonate (ref: Chandler et al., J. Chem Soc. Perk. Trans. 1, 1995, p. 1173) (1 mmol) in methylene chloride (10 mL) was added acetic acid (0.5 mL), appropriate aldehyde or ketone derivative and sodium cyanoborohydride (10 mmol). The reaction was stirred at room temperature for 16 h, quenched by the addition of $Et_3N$. The mixture was evaporated to dryness then chromatographed on silica gel column to give the desired product.

To the residue (1 mmol) was added 0.5 sodium hydroxide (10 mL) and the mixture was stirred at room temperature for 4 h, neutralized with HCl, filtered through a plug of cotton to give the desired compound.

Method C:

A mixture of methyl 4,7,8,9-tetra-O-acetyl-2-deoxy-2,3-didehydro-D-neuraminate (ref: Kumar et al. Carbohydrate Res. 1981, 94, 23) (1 mmol) in dioxane (10 mL), (Boc)$_2$O (1.5 mmol), and DMAP(1 mmol) was heated at 60° C. overnight. The solvent was removed and the residue was purified with silica gel to give methyl-4,7,8,9-tetra-O-acetyl-5-(N-t-butoxycarbony)(N-acetyl)amino-2,3-didehydro-2,3,5trideoxy-D-glycero-D-galacto-2-nonulopyranosidonate.

To the latter (1 mmol) in methanol (10 mL) was added, dropwise a solution of sodium methoxide in methanol (0.5 mmol). After stirring for an hour, the reaction mixture was neutralized with Dowex-200 H$^+$ resin. The resin was filtered off, the filtrate was concentrated to dryness to give methyl 5-t-butoxycarbonylamino-2,3-dideoxy-2,3,5-trideoxy-D-glycero-D-galacto-2-nonulopyranosidonate.

The latter (1 mmol) was dissolved in pyridine (10 mL), and acetic anhydride (10 mmol) was added to it slowly. After stirring at room temperature for 2 h, the solvent was removed under vacuum at 40° C. The residue was partitioned between methylene chloride and water. The organic layer was dried over MgSO$_4$ and concentrated. After purifying with silica gel chromatography, the appropriate fractions were collected to give methyl 4,7,8,9-tetra-O-acetyl-5-t-butoxycarbonylamino-2,3-didehydro-2,3,5-trideoxy-D-glycero-D-galacto-2-nonulopyranosidonate.

To a solution of the latter in dioxane (10 mL) was added 4M solution of HCl in dioxane (10 mL) at room temperature. After stirring overnight at room temperature, the solvent was removed under vacuum to give methyl 4,7,8,9-tetra-O-acetyl-5-amino-2,3-didehydro-2,3,5-trideoxy-D-glycero-D-galacto-2-nonulopyranosidonate.

To a mixture of methyl 4,7,8,9-tetra-O-acetyl-5-amino-2,3-didehydro-2,3,5-trideoxy-D-glycero-D-galacto-2-nonulopyranosidonate (1 mmol) in methylene chloride (10 mL) was added appropriate acid halide or acid anhydride (1.5 mmol) and triethylamine (1.5 mmol). The mixture was stirred at room temperature for 16 h. The reaction mixture was concentrated to dryness and the residue was purified by silica gel chromatography. The appropriate fractions were collected and concentrated to dryness.

To the residue (1 mmol) was added 0.5 N sodium hydroxide (10 mL) and the mixture was stirred at room temperature for 4 h, neutralized with HCl, filtered through a plug of cotton to give the desired compound.

Method D:

To a mixture of methyl 4,7,8,9-tetra-O-acetyl-5-amino-2,3-didehydro-2,3,5-trideoxy-D-glycero-D-galacto-2-nonulopyranosidonate [preparation described in method C] (1 mmol) in methylene chloride (10 mL) was added acetic acid (0.5 mL), appropriate aldehyde or ketone derivatives (5 mmol) and sodium cyanoborohydride (10 mmol). The reaction was stirred at room temperature for 16 h, and quenched by the addition of Et$_3$N. The mixture was evaporated to dryness then chromatographed on silica gel column to give the desired product.

To the residue (1 mmol) was added 0.5 N sodium hydroxide (10 mL) and the mixture was stirred at room temperature for 4 h, neutralized with HCl, filtered through a plug of cotton to give the desired compound.

Method E:

A mixture of methyl 4-azido-5-tert-butoxycarbonylamino-2,3-didehydro-2,3,4,5-tetradeoxy-D-glycero-D-galacto-2-nonulopyranosidonate (ref: Smith et al Eur. J. Med. Chem., 1996, 31, 143–150) (1 mmol), pyridine (10 mL) and acetic anhydride (1.5 mL) was stirred at room temperature for 3 h. The mixture was diluted with water and extracted with ethyl acetate. The organic layer was separated and washed with 0.1 N HCl, water, and dried over MgSO$_4$. After filtration, the filtrate was concentrated and the residue purified by silica gel column chromatography using ethyl acetate:hexane as an eluent to give methyl 4-azido-5-tert-butoxycarbonylamino-2,3-didehydro-2,3,4,5-tetradeoxy-7,8,9-tri-O-acetyl-D-glycero-D-galacto-2-nonulopyranosidonate.

A mixture of the latter azide (1 mmol) in dichloromethane (10 mL) and trifluoroacetic acid (2 mL) was stirred at room temperature for 16 h. The reaction mixture was concentrated and the residue washed with ether/hexane. The residue was dried under reduced pressure to give 4-azido-5-amino-2,3-didehydro-2,3,4,5-tetradeoxy-7,8,9-tri-O-acetyl-D-glycero-D-galacto-2-nonulopyranosidonate.

To a mixture of 4-azido-5-amino-2,3-didehydro-2,3,4,5-tetradeoxy-7,8,9-tri-O-acetyl-D-glycero-D-galacto-2-nonulopyranosidonate (1 mmol) in dichloromethane (25 mL) were added acid chloride or acid anhydride (2 mmol) and triethylamine (5 mmol) and stirred at room temperature for 4 h. The mixture was concentrated and the residue purified by silica gel column chromatography using ethyl acetate:hexane as an eluent. The appropriate fractions were collected together and concentrated to give different amides.

To the residue (1 mmol) was added 0.5 N sodium hydroxide (10 mL) and the mixture was stirred at room temperature for 4 h, neutralized with HCl, filtered through a plug of cotton to give the desired compound.

Method F:

To a mixture of methyl 4-azido-5-amino-2,3-didehydro-2,3,4,5-tetradeoxy-7,8,9-tri-O-acetyl-D-glycero-D-galacto-2-nonulopyranosidonate prepared according to method E (1 mmol) in dichloromethane (25 mL) was added acetic acid (0.5 mL), appropriate aldehyde or ketone derivatives (5 mmol) and sodium cyanoborohydride (10 mmol). The reaction was stirred at room temperature for 16 h, and quenched by the addition of Et$_3$N. The mixture was evaporated to dryness then chromatographed on silica gel column to give the desired product.

To the residue (1 mmol) was added 0.5 N sodium hydroxide (10 mL) and the mixture was stirred at room temperature for 4 h, neutralized with HCl, filtered through a plug of cotton to give the desired compound.

Method G:

To a mixture of methyl 4-azido-5-amino-2,3-didehydro-2,3,4,5-tetradeoxy-7,8,9-tri-O-acetyl-D-glycero-D-galacto-2-nonulopyranosidonate prepared according to method E (1 mmol) in dichloromethane (25 mL) were added acid chloride or acid anhydride (2 mmol) and triethylamine (5 mmol) and stirred at room temperature for 4 h. The mixture was concentrated and the residue purified by silica gel column chromatography using ethyl acetate: hexane as an eluent. The appropriate fractions were collected together and concentrated to give different amides.

To a pyridine solution (50 mL) of the latter 5-amide derivative (1 mmol) was bubbled hydrogen sulfide gas for 6 h, concentrated to dryness. The residue was purified with silica gel column. After concentrating the appropriate fractions, the free amine (amine at the 4-position) was obtained.

To a mixture of the latter amine (at 4-position) (1 mmol) in dichloromethane (25 mL) was added acetic acid (0.5 mL), appropriate aldehyde or ketone derivatives (5 mmol) and sodium cyanoborohydride (10 mmol). The reaction was stirred at room temperature for 16 h, quenched by the addition of $Et_3N$. The mixture was evaporated to dryness then chromatographed on silica gel column to give the desired product.

To the residue (1 mmol) was added 0.5 N sodium hydroxide (10 mL) and the mixture was stirred at room temperature for 4 h, neutralized with HCl, filtered through a plug of cotton to give the desired compound.

Method H:

To a suspension of methyl 5-acetamido-2,6-anhydro-3,5-di-deoxy-D-glycero-D-galacto-non-2-enonic ester (ref: von Itzstein et al. Chem. Commun. 1996, 2017–2018) (1 mmol) in acetone (12 mL) was added camphor sulfonic acid (1 mmol) and 2,2-dimethoxypropane (1 mmol). The reaction was stirred at room temperature for 16 h, and quenched by the addition of aqueous saturated solution of sodium bicarbonate. The reaction was extracted between EtOAc and water. The organic layer was collected, evaporated to dryness, and chromatographed on silica gel column to give the 8,9-acetal derivative.

To a solution of the latter in DMF (30 mL) at 0° C. was added NaH (1.1 mmol), stirred for 15 minutes and appropriate alkyl halide (1.5 mmol) was added. Reaction was stirred at RT for 4 h, and then quenched with saturated aqueous $NH_4Cl$. The reaction mixture was concentrated to dryness and purified by silica gel column chromatography to give the corresponding derivative at the 4-position.

To a solution of the latter (1 mmol) in THF (30 mL) was added HCl (1 N, 8 mL). The mixture was stirred at room temperature for 16 h, and then concentrated to dryness. To the residue was added 0.5 N NaOH and stirred at room temperature for 4 h, reaction was neutralized with HCl, filtered, through a plug of cotton to give the desired compound.

Method I:

To a mixture of methyl 4,7,8,9-tetra-O-acetyl-5-amino-2,3-didehydro-2,3,5-trideoxy-D-glycero-D-galacto-2-nonulopyranosidonate prepared according to method C (1 mmol) in methylene chloride (10 mL) was added appropriate acid chloride or acid anhydride (1.5 mmol) and triethylamine (1.5 mmol). The mixture was stirred at room temperature for 16 h. The reaction mixture was concentrated to dryness and the residue was purified by silica gel chromatography. The appropriate fractions were collected and concentrated to dryness.

To a mixture of the above amide (1 mmol) in MeOH (10 mL) was added a solution of sodium methoxide in MeOH (0.5 mmol). The reaction mixture was stirred at room temperature overnight. The reaction was neutralized by resin Dowex $H^+$, filtered, evaporated to dryness to give different amide analogs at the 5 position. Different ethers (at position 4) were made following method H starting from methyl 5-(alkylamide)-2,6-anhydro-3,5-di-deoxy-D-glycero-D-galacto-non-2-enonic ester analogs. The final targets were obtained after deprotection of the groups.

Method J:

A solution of methyl 4-azido-5-acetamido-2,3-didehydro-2,3,4,5-tetradeoxy-D-glycero-D-galacto-2-nonulopyranosidonate (ref: Smith et al., Eur. J. Med. Chem 1996, 31, 143–150) (1 mmol) in a mixture of MeOH/water (2/1) (15 mL) was added sodium periodate (5 mmol). The mixture was stirred at room temperature for 5 h, and filtered. To the residue in 2-propanol (10 mL), were added sodium chlorite (7 mmol), sodium diphosphate (5 mmol) and cyclohexene (1 mL), stirred for 3 h at room temperature, and partitioned between EtOAc and water. The organic layer was collected, dried over $MgSO_4$, filtered then evaporated to dryness to give the acid derivative at the 6-position.

To a solution of the latter (1 mmol) in THF (10 mL) was added ethyl chloroformate (4 mmol) and $Et_3N$ (4 mmol). The reaction was stirred for 1 h at room temperature and appropriate amine (4 mmol) was added to the reaction mixture and stirred at room temperature overnight. The reaction was then extracted between EtOAc and water. The organic layer was collected, dried over $MgSO_4$, filtered, evaporated to dryness then chromatographed on silica gel column to give different amides.

To the residue (1 mmol) was added 0.5 N sodium hydroxide (10 mL) and the mixture was stirred at room temperature for 4 h, neutralized with HCl, filtered through a plug of cotton to give the desired compound.

Method K:

To a solution of methyl 4-azido-5-acetamido-7,8,9-tri-O-acetyl-2,3-didehydro-2,3,4,5-tetradeoxy-D-glycero-D-galacto-2-nonulopyranosidonate (ref: Chandler et al., Carbohydrate Res. 244, 1993, 181–185) (1 mmol) in THF (10 mL) was added either methyl propriolate (5 mmol) or phenyl vinyl sulfoxide (2 mmol). The reaction was heated to reflux for 16 h, evaporated to dryness, then chromatographed on silica gel column to give the corresponding triazole derivative.

To the residue (1 mmol) was added 0.5 N sodium hydroxide (10 mL) and the mixture was stirred at room temperature for 4 h, neutralized with HCl, filtered through a plug of cotton to give the desired compound.

Method L:

To a mixture of 4-azido-5-amino-2,3-didehydro-2,3,4,5-tetradeoxy-7,8,9-tri-O-acetyl-D-glycero-D-galacto-2-nonulopyranosidonate prepared according to method E (1 mmol) in dichloromethane (25 mL) were added acid halide or acid anhydride (2 mmol) and triethylamine (5 mmol) and stirred at room temperature for 4 h. The mixture was concentrated and the residue purified by silica gel column chromatography using ethyl acetate:hexane as an eluent. The appropriate fractions were collected together and concentrated to give different amides.

Hydrogen sulfide gas was bubbled through a pyridine solution (50 mL) of the latter azide (1 mmol) for 6 h, and concentrated to dryness. The residue was purified with silica gel column and the appropriate fractions were concentrated to give the free amine.

To a solution of the latter amine (1 mmol) in methylene chloride (20 mL), was added appropriate sulfonyl halide, sulfonic anhydride or sulfonic acid (1.5 mmol) and triethylamine (1.5 mmol). The mixture was stirred at room temperature for 16 h. The reaction mixture was concentrated to dryness and the residue was purified by silica gel chromatography using ethyl acetate:hexane (1:1) as an eluent. The appropriate fractions were collected and concentrated to dryness.

To the residue (1 mmol) was added 0.5 N sodium hydroxide (10 mL) and the mixture was stirred at room temperature for 4 h, neutralized with HCl, filtered through a plug of cotton to give the desired compound.

Method M:

To a mixture of methyl 4,7,8,9-tetra-O-acetyl-5-amino-2,3-didehydro-2,3,5-trideoxy-D-glycero-D-galacto-2- nonulopyranosidonate prepared according to method C (1 mmol) in methylene chloride (20 mL) was added appropriate sulfonyl halide, sulfonic anhydride or sulfonic acid (1.5 mmol) and triethylamine (1.5 mmol). The mixture was stirred at room temperature for 16 h. The reaction mixture was concentrated to dryness and the residue was purified by silica gel chromatography using ethyl acetate:hexane (1:1) as an eluent. The appropriate fractions were collected and concentrated to dryness.

To the residue (1 mmol) was added 0.5 N sodium hydroxide (10 mL) and the mixture was stirred at room temperature for 4 h, neutralized with HCl, filtered through a plug of cotton to give the desired compound.

Method N:

To a mixture of methyl 4,7,8,9-tetra-O-acetyl-5-[(4-chlorobutanoyl)amino]-2,3-didehydro-2,3,5-trideoxy-D-glycero-D-galacto-2-nonulopyranosidonate or methyl 4,7,8,9-tetra-O-acetyl-5-[(5-chloropentanoyl)amino]-2,3-didehydro-2,3,5-trideoxy-D-glycero-D-galacto-2-nonulopyranosidonate prepared according to method C (1 mmol) in DMF (5 mL) was added sodium hydride (1 mmol). The reaction was heated to 60° C. for 2 h, evaporated to dryness and partitioned between EtOAc and water. The organic layer was collected, dried over MgSO$_4$, filtered and evaporated to dryness. The residue was chromatographed on silica gel column to give the desired product.

To the residue (1 mmol) was added 0.5 N sodium hydroxide (10 mL) and the mixture was stirred at room temperature for 4 h, neutralized with HCl, filtered through a plug of cotton to give the desired compound.

The following non-limiting examples are presented to further illustrate the present invention.

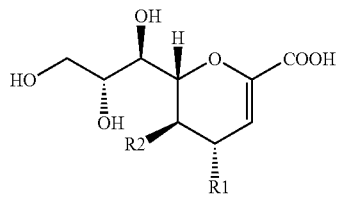

| Example No. | R1 | R2 | Method used to preparation | Mass Spec. |
|---|---|---|---|---|
| 1 | [N-methyl benzamide structure] | NHC(O)CH$_3$ | A | (ES$^+$): 417.3 (M + Na) |
| 2 | [N-methyl isovaleramide structure] | —NHC(O)CH$_3$ | A | (ES$^+$): 397.5 (M + Na) |
| 3 | [N-methyl furan-2-carboxamide structure] | —NHC(O)CH$_3$ | A | (ES$^+$): 407.3 (M + Na) |
| 4 | —NHC(O)CH$_3$ | —NHC(O)CH$_3$ | A | (ES$^+$): 355.3 (M + Na) |
| 5 | [N-methyl 2-thiopheneacetamide structure] | —NHC(O)CH$_3$ | A | (ES$^+$): 437.5 (M + Na) |
| 6 | [N-methyl thiophene-2-carboxamide structure] | —NHC(O)CH$_3$ | A | (ES$^+$): 423.4 (M + Na) |
| 7 | [N-methyl 3-thiopheneacetamide structure] | —NHC(O)CH$_3$ | A | (ES$^+$): 437.68 (M + Na) |

-continued
| | | | | |
|---|---|---|---|---|
| 8 | 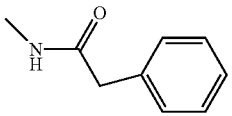 | —NHC(O)CH$_3$ | A | (ES$^+$): 431.9 (M + Na) |
| 9 | 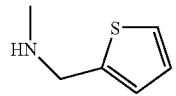 | —NHC(O)CH$_3$ | B | (ES$^+$): 385.1 (M + H) |
| 10 | 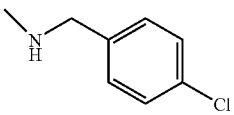 | —NHC(O)CH$_3$ | B | (ES$^+$): 413.2 (M + H) |
| 11 | 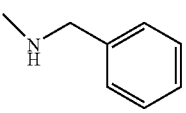 | —NHC(O)CH$_3$ | B | (ES$^+$): 379.3 (M + H) |
| 12 | 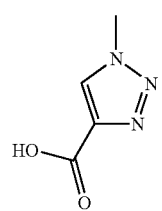 | —NHC(O)CH$_3$ | K | (ES$^+$): 385.0 (M + H) |
| 13 | 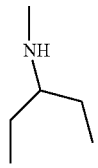 | —NHC(O)CH$_3$ | B | (ES$^+$): 359.1 (M + H) |
| 14 | 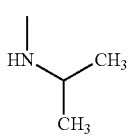 | —NHC(O)CH$_3$ | B | (ES$^+$): 331.1 (M + H) |
| 15 | 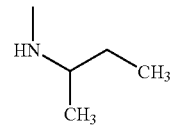 | —NHC(O)CH$_3$ | B | (ES$^+$): 345.1 (M + H) |
| 16 | 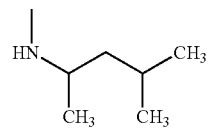 | —NHC(O)CH$_3$ | B | (ES$^+$): 373.1 (M + H) |
| 17 | 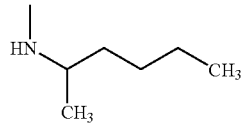 | —NHC(O)CH$_3$ | B | (ES$^+$): 373.1 (M + H) |
| 18 | 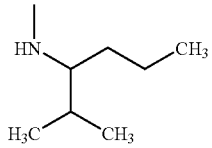 | —NHC(O)CH$_3$ | B | (ES$^+$): 387.2 (M + H) |

| | | | | |
|---|---|---|---|---|
| 19 | ![structure]  HN(CH3)-CH(CH3)-CH2-CH(CH3)-CH3 | —NHC(O)CH₃ | B | (ES⁺): 387.2 (M + H) |
| 20 | HN(CH3)-CH(CH3)-CH2-CH2-COOH | —NHC(O)CH₃ | B | (ES⁺): 389.1 (M + H) |
| 21 | HN(CH3)-CH(CH3)-CH(CH3)-CH2CH3 | —NHC(O)CH₃ | B | (ES⁺): 372.2 (M + H) |
| 22 | HN(CH3)-CH(CH2CH3)-CH2-Ph | —NHC(O)CH₃ | B | (ES⁺): 421.2 (M + H) |
| 23 | HN(CH3)-CH2-CH(CH3)-CH2CH3 | —NHC(O)CH₃ | B | (ES⁺): 359.2 (M + H) |
| 24 | HN(CH3)-CH2-CH2-CH(CH3)-Ph | —NHC(O)CH₃ | B | (ES⁺): 421.2 (M + H) |
| 25 | HN(CH3)-CH2-CH(CH3)2 | —NHC(O)CH₃ | B | (ES⁺): 345.1 (M + H) |
| 26 | 1-methyl-1,2,3-triazole | —NHC(O)CH₃ | K | (ES⁺): 341.1 (M + H) |
| 27 | CH₃-NH-SO₂-thiophene | —NHC(O)CH₃ | A | (ES⁺): 459.43 (M + Na) |
| 28 | CH₃-NH-SO₂-CH₃ | —NHC(O)CH₃ | A | (ES⁺): 391.42 (M + Na)⁺ |
| 29 | CH₃-NH-SO₂-Ph | —NHC(O)CH₃ | A | (ES⁺): 453.43 (M + Na) |

-continued

| | | | | |
|---|---|---|---|---|
| 30 | [structure: CH₃NH-SO₂-CH₂CF₃] | —NHC(O)CH₃ | A | (ES⁺): 459.62 (M + Na) |
| 31 | [structure: CH₃NH-SO₂-CH₂-phenyl] | —NHC(O)CH₃ | A | (ES⁺): 467.43 (M + Na) |
| 32 | [structure: CH₃NH-SO₂-CH₂CH₂CH₃] | —NHC(O)CH₃ | A | (ES⁺): 419.57 (M + Na) |
| 33 | [structure: CH₃NH-SO₂-CH=CH-phenyl] | —NHC(O)CH₃ | A | (ES⁺): 479.3 (M + Na) |
| 34 | [structure: CH₃NH-SO₂-CH₂-(2-NO₂-phenyl)] | —NHC(O)CH₃ | A | (ES⁺): 512.3 (M + Na) |
| 35 | [structure: CH₃NH-SO₂-(2-NO₂-phenyl)] | —NHC(O)CH₃ | A | (ES⁺): 498.3 (M + Na) |
| 36 | [structure: CH₃NH-SO₂-(3-NO₂-phenyl)] | —NHC(O)CH₃ | A | (ES⁺): 498.1 (M + Na) |
| 37 | [structure: CH₃NH-SO₂-(4-F-phenyl)] | —NHC(O)CH₃ | A | (ES⁺): 471.2 (M + Na) |
| 38 | [structure: CH₃NH-SO₂-(4-Cl-phenyl)] | —NHC(O)CH₃ | A | (ES⁺): 487.1 (M + Na) |
| 39 | [structure: CH₃NH-SO₂-(2-naphthyl)] | —NHC(O)CH₃ | A | (ES⁺): 503.2 (M + Na) |
| 40 | [structure: CH₃NH-SO₂-(4-OMe-phenyl)] | —NHC(O)CH₃ | A | (ES⁺): 483.2 (M + Na) |

-continued

| | | | | |
|---|---|---|---|---|
| 41 | [structure: N-H-SO2-C6H4-C(CH3)2-CH3 with N-methyl] | —NHC(O)CH3 | A | (ES+): 509.3 (M + Na) |
| 42 | [structure: N-methyl sulfonamide of naphthalene] | —NHC(O)CH3 | A | (ES+): 503.2 (M + Na) |
| 43 | [structure: N-methyl sulfonamide of 4-COOH phenyl] | —NHC(O)CH3 | A | (ES+): 473.2 (M + Na) |
| 44 | [structure: N-methyl sulfonamide of 4-methylphenyl] | —NHC(O)CH3 | A | (ES+): 467.2 (M + Na) |
| 45 | [structure: N,N-dimethyl ethylsulfonamide] | —NHC(O)CH3 | A | (ES+): 405.2 (M + Na) |
| 46 | [structure: N-methyl vinylsulfonamide] | —NHC(O)CH3 | A | (ES+): 403.1 (M + Na) |
| 47 | [structure: N-methyl sulfonamide of 4-methyl-2-acetamido thiazole] | —NHC(O)CH3 | A | (ES+): 531.2 (M + Na) |
| 48 | [structure: N-methyl sulfonamide of 4-acetamidophenyl] | —NHC(O)CH3 | A | (ES+): 510.3 (M + Na) |
| 49 | [structure: N-methyl sulfonamide of 2-methylphenyl] | —NHC(O)CH3 | A | (ES+): 467.2 (M + Na) |
| 50 | [structure: N-methyl sulfonamide of 4-(methoxycarbonylamino)phenyl] | —NHC(O)CH3 | A | (ES+): 526.3 (M + Na) |
| 51 | [structure: ethylsulfonyl-CH2-methylsulfonyl] | —NHC(O)CH3 | A | (ES+): 469.1 (M + Na) |

-continued
| | | | | |
|---|---|---|---|---|
| 52 | 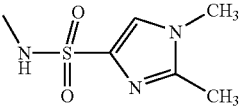 | —NHC(O)CH$_3$ | A | (ES$^+$): 471.2 (M + Na) |
| 53 | 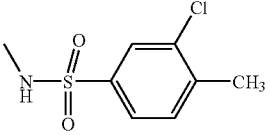 | —NHC(O)CH$_3$ | A | (ES$^+$): 501.1 (M + Na) |
| 54 | 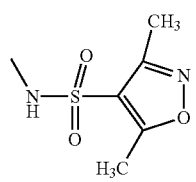 | —NHC(O)CH$_3$ | A | (ES$^+$): 472.1 (M + Na) |
| 55 | 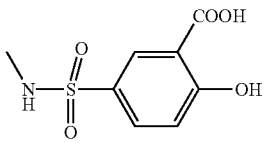 | —NHC(O)CH$_3$ | A | (ES$^+$): 489.2 (M + Na) |
| 56 | 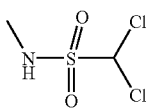 | —NHC(O)CH$_3$ | A | (ES$^+$): 459.1 (M + Na) |
| 57 | 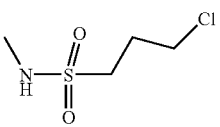 | —NHC(O)CH$_3$ | A | (ES$^+$): 453.1 (M + Na) |
| 58 | 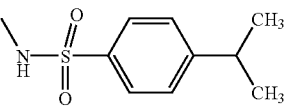 | —NHC(O)CH$_3$ | A | (ES$^+$): 495.2 (M + Na) |
| 59 | 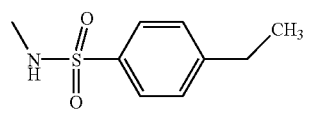 | —NHC(O)CH$_3$ | A | (ES$^+$): 481.2 (M + Na) |
| 60 | —OH | 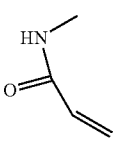 | C | (ES$^+$): 326.2 (M + Na) |
| 61 | —OH | 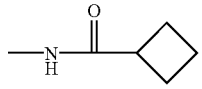 | C | (ES$^+$): 354.2 (M + Na) |
| 62 | —OH | 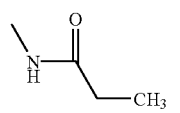 | C | (ES$^+$): 328.2 (M + Na) |
| 63 | —OH | 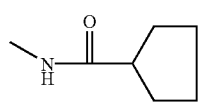 | C | (ES$^+$): 344.2 (M − H) |

-continued

| | | | | |
|---|---|---|---|---|
| 64 | —OH | *N-methyl furan-2-carboxamide group* | C | (ES+): 366.2 (M − H) |
| 65 | —OH | *N-methyl thiophene-2-carboxamide group* | C | (ES+): 358.2 (M − H) |
| 66 | —OH | *N-methyl propanamide group* | C | (ES+): 318.2 (M − H) |
| 67 | —OH | *N-methyl 3-methylbutanamide group* | C | (ES+): 323.3 (M − H) |
| 68 | —OH | *N-methyl cyclopropanecarboxamide group* | C | (ES+): 316.2 (M − H) |
| 69 | —OH | *N-methyl 3,3-dimethylbutanamide group* | C | (ES+): 346.3 (M − H) |
| 70 | —OH | *N-methyl benzamide group* | C | (ES+): 352.2 (M − H) |
| 71 | —OH | *N-methyl isobutyramide group* | C | (ES+): 318.3 (M − H) |
| 72 | —OH | *N-methyl tert-butyl carbamate group* | C | 348.3 (M − H) |
| 73 | —OH | *N-methyl pivalamide group* | C | (ES+): 356.1 (M + Na) |
| 74 | —OH | *N-methyl 3-phenylpropanamide group* | C | (ES+): 380.2 (M − H) |
| 75 | —OH | *N-methyl 2-chloropropanamide group* | C | (ES+): 338.1 (M − H) |

-continued

| | | | | |
|---|---|---|---|---|
| 76 | —OH | *N*-methyl-2-chloroacetamide group | C | (ES+): 324.0 (M − H) |
| 77 | —OH | *N*-methyl-methacrylamide group | C | (ES+): 316.1 (M − H) |
| 78 | —OH | *N*-methyl-2-ethylbutanamide group | C | (ES+): 346.2 (M − H) |
| 79 | —OH | *N*-methyl-2-phenylacetamide group | C | (ES+): 390.2 (M + Na) |
| 80 | —OH | *N*-methyl-3-methyl-2-butenamide group | C | (ES+): 354.2 (M + Na) |
| 81 | —OH | *N*-methyl-2-(thiophen-2-yl)acetamide group | C | (ES+): 372.0 (M − H) |
| 82 | —OH | *N*-methyl-2-methylbutanamide group | C | (ES+): 356.2 (M + Na) |
| 83 | —OH | *N*-methyl-4-chlorobutanamide group | C | (ES+): 352.0 (M − H) |
| 84 | —OH | *N*-methyl-5-chloropentanamide group | C | (ES+): 366.0 (M − H) |
| 85 | —OH | 1-methyl-2-oxopiperidine group | N | (ES+): 330.1 (M − H) |
| 86 | —OH | 1-methyl-2-oxopyrrolidine group | N | (ES−): 316.0 (M − H) |

-continued
| | | | | |
|---|---|---|---|---|
| 87 | —OH | 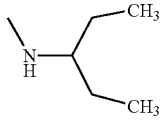 | D | (ES⁻): 318.1 (M − H) |
| 88 | —OH | 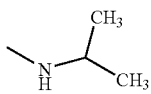 | D | (ES⁻): 314.1 (M + Na) |
| 89 | —OH | 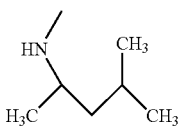 | D | (ES⁻): 332.1 (M − H)⁻ |
| 90 | —OH | 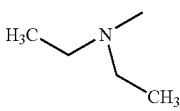 | D | (ES⁺): 306.1 (M + H) |
| 91 | —OH | 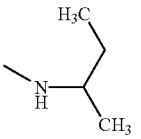 | D | (ES⁺): 366.2 (M − H) |
| 92 | —OH | 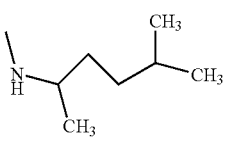 | D | (ES⁺): 346.3 (M + Na) |
| 93 | —OH | 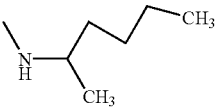 | D | (ES⁺): 356.1 (M + Na) |
| 94 | —OH | 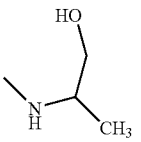 | D | (ES⁺): 330.1 (M + Na) |
| 95 | —OH | 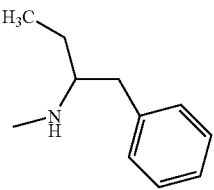 | D | (ES⁺): 404.1 (M + Na) |
| 96 | —OH | 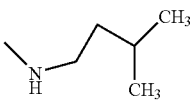 | D | (ES⁺): 342.2 (M + Na) |
| 97 | —OH | 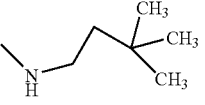 | D | (ES⁺): 356.3 (M + Na) |

-continued

| | | | | |
|---|---|---|---|---|
| 98 | —OH | CH₃CH₂CH₂N(H)CH₃ (N-methyl propylamine) | D | (ES⁺): 328.3 (M + Na) |
| 99 | —OH | CH₃CH(CH₂CH₃)CH(CH₃)NHCH₃ | D | (ES⁺): 334.2 (M + Na) |
| 100 | —OH | (CH₃)₂CHCH(CH₃)NHCH₃-like (N-methyl isobutylamine) | D | (ES⁻): 346.3 (M − H) |
| 101 | —OH | N-methyl pyrrolidine | D | (ES⁻): 302.2 (M − H) |
| 102 | —OH | (CH₃)₃CCH₂NHCH₃ | D | (ES⁻): 318.2 (M − H) |
| 103 | —OCH₂C₆H₅ | —N(H)C(O)CH(CH₃)₂ | I | (ES⁻): 408.2 (M − H) |
| 104 | —OCH₂(4-Cl-C₆H₄) | —N(H)C(O)CH(CH₃)₂ | I | (ES⁻): 442.2 (M − H)⁻ |
| 105 | —OCH₂CH=CHC₆H₅ | —N(H)C(O)CH(CH₃)₂ | I | (ES⁻): 434.2 (M − H)⁻ |
| 106 | —OCH₂CH=CH₂ | —N(H)C(O)CH(CH₃)₂ | I | (ES⁻): 358.2 (M − H) |
| 107 | —OCH₂CH(CH₃)CH₃ (isobutoxy) | —N(H)C(O)CH(CH₃)₂ | I | (ES⁻): 374.2 (M − H) |
| 108 | —OCH₂CH₂CH₃ | —N(H)C(O)CH(CH₃)₂ | I | 360.2 (M − H) |
| 109 | —OCH₃ | —N(H)C(O)CH(CH₃)₂ | i | (ES⁻): 332.1 (M − H)⁻ |

-continued

| | | | | |
|---|---|---|---|---|
| 110 | —O—CH₂—CH₃ | C(=O)CH(CH₃)CH₃ | I | (ES⁻): 346.2 (M − H) |
| 111 | methoxymethyl-thiophene | N-H-C(=O)-CH(CH₃)₂ | I | (ES⁻): 414.1 (M − H) |
| 112 | —OH | N-H-S(=O)₂-CH₃ | M | (ES⁻): 326.2 (M − H)⁻ |
| 113 | —N₃ | N-H-C(=O)-CH(CH₃)(CH₂CH₃) | E | (ES⁺): 381.2 (M + Na) |
| 114 | —N₃ | N-H-C(=O)-CH(CH₃)₂ | E | (ES⁺): 367.1 (M + Na) |
| 115 | —N₃ | N-H-C(=O)-cyclopropyl | E | (ES⁻): 341.1 (M − H) |
| 116 | —N₃ | N-H-C(=O)-cyclobutyl | E | (ES⁻): 355.1 (M − H) |
| 117 | —N₃ | N-H-CH₂-CH(CH₃)₂ | F | (ES⁺): 381.2 (M + Na) |
| 118 | —NH—CH₂-phenyl | N-H-C(=O)-CH(CH₃)₂ | G | (ES⁻): 407.1 (M − H) |
| 119 | —NH—CH₂-(4-Cl-phenyl) | N-H-C(=O)-CH(CH₃)₂ | G | (ES⁻): 441.1 (M − H) |
| 120 | —NH—C(=O)-cyclopropyl | N-H-C(=O)-CH(CH₃)₂ | G | (ES⁻): 413.1 (M − H) |
| 121 | —NH—S(=O)₂-CHCl₂ | N-H-C(=O)-CH(CH₃)₂ | L | (ES⁺): 487.1 (M + Na) |

-continued

| # | R1 | R2 | | |
|---|---|---|---|---|
| 122 | [4-chlorophenyl-SO2-NH-CH2-] | [-NH-C(O)-CH(CH3)2] | L | (ES+): 517.18 (M + Na) |
| 123 | [4-methylphenyl-SO2-NH-CH2-] | [-NH-C(O)-CH(CH3)2] | L | (ES+): 495.25 (M + Na) |
| 124 | [3-chloro-4-methylphenyl-SO2-NH-CH2-] | [-NH-C(O)-CH(CH3)2] | L | (ES+): 529.23 (M + Na) |
| 125 | [thiophen-2-yl-SO2-NH-CH2-] | [-NH-C(O)-CH(CH3)2] | L | (ES−): 463.2 (M − H) |
| 126 | [(E)-styryl-SO2-NH-CH2-] | [-NH-C(O)-CH(CH3)2] | L | (ES+): 507.27 (M + Na) |
| 127 | [Cl2CH-SO2-NH-CH2-] | [-NH-C(O)-cyclopropyl] | L | (ES+): 485.1 (M + Na) |
| 128 | [4-chlorophenyl-SO2-NH-CH2-] | [-NH-C(O)-cyclopropyl] | L | (ES+): 513.1 (M + Na) |
| 129 | [4-methylphenyl-SO2-NH-CH2-] | [-NH-C(O)-cyclopropyl] | L | (ES+): 493.2 (M + Na) |
| 130 | [3-chloro-4-methylphenyl-SO2-NH-CH2-] | [-NH-C(O)-cyclopropyl] | L | (ES+): 527.2 (M + Na) |
| 131 | [(E)-styryl-SO2-NH-CH2-] | [-NH-C(O)-cyclopropyl] | L | (ES+): 505.2 (M + Na) |
| 132 | [thiophen-2-yl-SO2-NH-CH2-] | [-NH-C(O)-cyclopropyl] | L | (ES−): 461.2 (M − H) |
| 133 | [4-chlorobenzyloxy-] | —NHC(O)CH3 | H | (ES−): 414.2 (M − H) |

-continued
| | | | | |
|---|---|---|---|---|
| 134 | 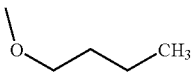 | —NHC(O)CH$_3$ | H | (ES$^-$): 346.1 (M − H) |
| 135 | 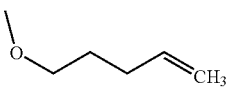 | —NHC(O)CH$_3$ | H | (ES$^-$): 358.1 (M − H) |
| 136 | 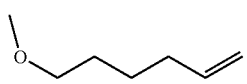 | —NHC(O)CH$_3$ | H | (ES$^-$): 372.2 (M − H) |
| 137 | 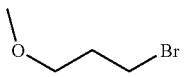 | —NHC(O)CH$_3$ | H | No MS |
| 138 |  | —NHC(O)CH$_3$ | H | (ES$^-$): 342.1 (M − H) |
| 139 | 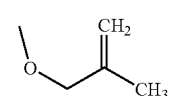 | —NHC(O)CH$_3$ | H | (ES$^-$): 344.1 (M − H) |
| 140 | 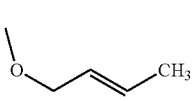 | —NHC(O)CH$_3$ | H | (ES$^-$): 344.1 (M − H) |
| 141 | 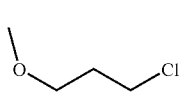 | —NHC(O)CH$_3$ | H | (ES$^-$): 366.1 (M − H) |
| 142 | 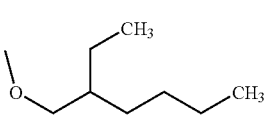 | —NHC(O)CH$_3$ | H | (ES$^-$): 402.3 (M − H) |
| 143 | 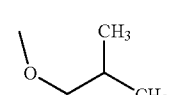 | —NHC(O)CH$_3$ | H | (ES$^-$): 346.2 (M − H) |
| 144 | 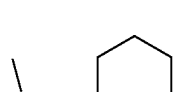 | —NHC(O)CH$_3$ | H | (ES$^-$): 386.3 (M − H) |
| 145 | 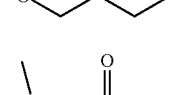 | —NHC(O)CH$_3$ | H | (ES$^-$): 348.1 (M − H) |
| 146 | 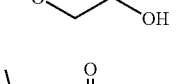 | —NHC(O)CH$_3$ | H | (ES$^-$): 360.1 (M − H) |
| 147 | 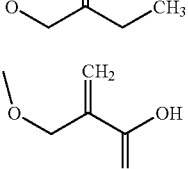 | —NHC(O)CH$_3$ | H | (ES$^-$): 374.1 (M − H) |
| 148 | 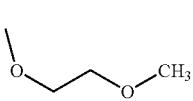 | —NHC(O)CH$_3$ | H | (ES$^-$): 348.1 (M − H) |

-continued

| | | | | |
|---|---|---|---|---|
| 149 | CH₃-O-CH₂-CH=CH-CH₃ | —NHC(O)CH₃ | H | (ES⁻): 358.1 (M − H) |
| 150 | CH₃-O-CH₂-cyclopropyl | —NHC(O)CH₃ | H | (ES⁻): 344.3 (M − H) |
| 151 | CH₃-O-CH₂-CH₃ | —NHC(O)CH₃ | H | (ES⁻): 318.1 (M − H) |
| 152 | CH₃-O-CH₂-phenyl | —NHC(O)CH₃ | H | (ES⁻): 380.1 (M − H) |
| 153 | CH₃-O-CH₂-CH₂-CH₃ | —NHC(O)CH₃ | H | (ES⁻): 332.1 (M − H) |
| 154 | CH₃-O-CH₂-CH=CH₂ | —NHC(O)CH₃ | H | (ES⁻): 330.1 (M − H) |
| 155 | —OCH₃ | —NHC(O)CH₃ | H | (ES⁻): 304.1 (M − H) |

[Structure: dihydropyran with AcHN, N₂ (azido), C(O)R1, and CO₂H substituents]

| Example No. | R1 | Method used for preparation | Mass Spec. |
|---|---|---|---|
| 156 | —NH(CH₃)CH₂CH₂CH₂CH₃ | J | No MS |
| 157 | —NH(CH₃)CH₂CH(CH₃)₂ | J | No MS |
| 158 | —N(CH₃)₂ | J | (ES⁺): 320.11 (M + Na) |
| 159 | —NH(CH₃)CH₂-phenyl | J | (ES⁺): 358.18 (M + Na) |
| 160 | —NH(CH₃)CH(CH₃)₂ | J | (ES⁺): 310.16 (M + Na) |
| 161 | —NHCH₃ | J | (ES⁺): 282.10 (M + Na) |

-continued

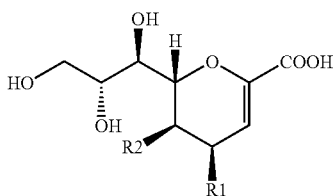

| Example No. | R1 | R2 | Method used to preparation | Mass Spec. |
|---|---|---|---|---|
| 162 | (N-methylsulfamoyl-methyl group with S(O)₂CH₃) | NHC(O)CH₃ | A | (ES⁻): 366.73 (M − H) |
| 163 | (N-methyl phenylsulfonamide) | —NHC(O)CH₃ | A | (ES⁻): 428.70 (M − H) |
| 164 | (N-methyl benzylsulfonamide) | —NHC(O)CH₃ | A | (ES⁻): 443.05 (M − H) |
| 165 | (N-methyl thiophenesulfonamide) | —NHC(O)CH₃ | A | (ES⁻): 435.02 (M − H) |

Compounds of the present invention are useful as paramyxovirus neuraminidase inhibitors themselves.

Dosage and Form istration preferably contain a water-soluble salt of the active ingredient, suitable stabilizing agents, and, if necessary, buffering agents. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company and in the Handbook of Pharmaceuticals Excipients, American Pharmaceutical Association, both standard reference texts in this field.

Useful pharmaceutical dosage forms for administration of the compounds according to the present invention can be illustrated as follows:

Hard Shell Capsules

A large number of unit capsules are prepared by filling standard two-piece hard gelatin capsules each with 100 mg of powdered prodrug, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into molten gelatin to form soft gelatin capsules containing 100 mg of the active ingredient. The capsules are washed and dried. The compound can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability improve elegance and stability or delay absorption.

Immediate Release Tablets/Cap&UICS

These are solid oral dosage forms made by conventional and novel processes. These units are taken orally without water for immediate dissolution and delivery of the medication. The prodrug is mixed in a liquid containing ingredient such as sugar, gelatin, pectin, and sweeteners. These liquids are solidified into solid tablets or caplets by freeze drying and solid state extraction techniques. The compounds may be compressed with viscoelastic and thermoelastic sugars and polymers or effervescent components to produce porous matrices intended for immediate release, without the need of water.

Moreover, the compounds of the present invention can be administered in the form of nose drops, metered dose nasal or buccal inhalers. The drug is delivered from a nasal solution as a fine mist or from a powder as an aerosol.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

What is claimed is:

1. A compound represented by one of the formulas:

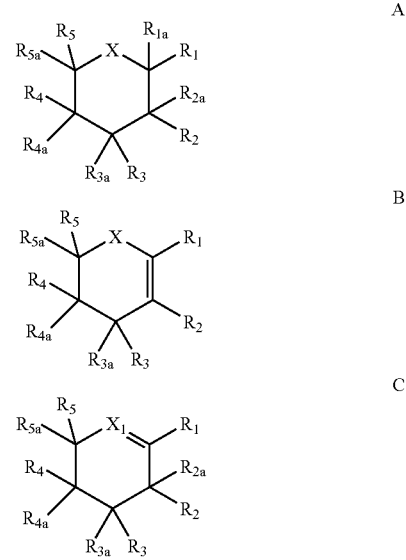

wherein X is selected from the group consisting of:
  CHR, O, NR, N—OR, NR(O), S, S(O) and S(O)O
  $X_1$ is selected from the group consisting of CR, N, and N(O);
R is selected from the group consisting of:
  H, alkyl, alkene, alkyne, CN, $NO_2$, $N_3$, halo and $NHR_{10}$;
$R_1$ is selected from the group consisting of:
  H, $(CH_2)nCO_2R_{10}$, $(CH_2)$n-tetrazol, $(CH_2)nSO_3H$, $(CH_2)nSO_2H$, $(CH_2)nPO_3H_2$, $(CH_2)nCONR_{10}R_{10a}$, $(CH_2)nNO_2$, and $(CH_2)nCHO$;
$R_{1a}$ is selected from the group consisting of:
  H, $(CH_2)nOR_{10}$, $(CH_2)nCN$, $(CH_2)nNR_{10}R_{10a}$, $(CH_2)nNHC(O)R_{10}$, $(CH_2)nC(O)NR_{10}R_{10a}$, and $(CH_2)nOC(O)R_{10}$;
$R_1$ and $R_{1a}$ both cannot be H
each of $R_2$ and $R_{2a}$ is independently selected from the group consisting of H, halo, CN, $(CH_2)nCO_2R_{10}$, $(CH_2)nNR_{10}R_{10a}$ and $(CH_2)_n$—$OR_{10}$;
each of $R_3$ and $R_{3a}$ is independently selected from the group consisting of:
  H, $NHSO_2R_{10}$, $N(O)$—$SO_2R_{10}$, $NR_{10}SO_2R_{10a}$, $(CH_2)mYR_{10}$, and $(CH_2)mR_6$; provided that when $R_3$ or $R_{3a}$ is $(CH_2)_mYR_{10}$ or $(CH_2)_mR_6$ than m is at least 1 for $R_3$ or $R_{3a}$;
at least one of $R_3$ and $R_{3a}$ is other than H
Y is selected from the group consisting of:
  O, NH, NHC(O), C(O)NH, S, S(O), S(O)O, NHS(O)O, S(O)ONH, NHC(O)NH and heterocycle;
$R_3$ and $R_{3a}$ together may be
  =O, =$CHR_6$, =$CHR_{10}$, =$NR_{10}$, and =N—$OR_{10}$
$R_4$ is $(CH_2)_mYR_{10}$,
$R_{4a}$ is selected from the group consisting of:
  H, $(CH_2)mYR_{10}$, and $(CH_2)mR_6$ R₄ and R₄ₐ together may be:
=O, =CHR₆, =CHR₁₀, =NR₁₀ and =N—OR₁₀ each of R₅ and R₅ₐ is independently selected from the group consisting of C(R₇)(R₇ₐ)H, C(R₇)(R₇ₐ)C(R₈)(R₈ₐ)H, C(R₇)(R₇ₐ)C(R₈)(R₈ₐ)C(R₉)(R₉ₐ)H, OC(R₇)(R₇ₐ)H, OC(R₇)(R₇ₐ)C(R₈)(R₈ₐ)H, C(R₇)(R₇ₐ)OC(R₈)(R₈ₐ)H, N(R₁₀)C(R₇)(R₇ₐ)H, N(R₁₀) C(R₇)(R₇ₐ)C(R₈)(R₈ₐ)H, C(R₇)(R₇ₐ)N(R₁₀)C(R₈)(R₈ₐ)H, and C(O)NR₁₀R₁₀ₐ;

R₆ is selected from the group consisting of
H, halo, CN, NO₂, N₃, CO₂R₁₀, R₁₀ and NR₁₀R₁₀ₐ;

each R₇, R₇ₐ, R₈, R₈ₐ, R₉ and R₉ₐ is individually selected from the group consisting of:
H, (CH₂)mYR₁₀ and (CH₂)mR₆

R₇ₐ is (CH₂)mYR₁₀ each of the R₁₀ and R₁₀ₐ is individually selected from the groups consisting of:
H, alkyl, substituted alkyl, aryl, substituted aryl, arylalkyl, substituted arylalkyl, heterocycle, substituted heterocycle, alkenyl, substituted alkenyl, alkynyl, and substituted alkynyl;

Each of m and n is individually 0, 1, 2, 3, or 4;

and pharmaceutically acceptable salt thereof; and prodrugs thereof.

2. The compound according to claim 1 being selected from the group consisting of:

(2R,3R,4S)-3-(Acetylamino)-4-[(thien-2-ylsulfonyl)amino]-2-[(1R,2R)-1,2,3-trihydroxypropyl]-3,4-dihydro-2H-pyran-6-carboxylic acid (2R,3R,4S)-3-(Acetylamino)-4-[(methylsulfonyl)amino]-2-[(1R,2R)-1,2,3-trihydroxypropyl]-3,4-dihydro-2H-pyran-6-carboxylic acid (2R,3R,4S)-3-(Acetylamino)-4-[(phenylsulfonyl)amino]-2-[(1R,2R)-1,2,3-trihydroxypropyl]-3,4-dihydro-2H-pyran-6-carboxylic acid (2R,3R,4S)-3-(Acetylamino)-4-{[(2,2,2-trifluoroethyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(benzylsulfonyl)amino]2-[(1R,2R)-1,2,3-trihydroxypropyl]-3,4-dihydro-2H-pyran-6-carboxylic acid (2R,3R,4S)-3-(Acetylamino)-4-[(propylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(methylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(phenylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(benzylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(thien-2-ylsulfonyl)amino]-2-[(1R,2R)-1,2,3-trihydroxypropyl]-3,4-dihydro-2H-pyran-6-carboxylic acid (2R,3R,4S)-3-(Acetylamino)-4-({[(E)-2-phenylethenyl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-{[(2-nitrobenzyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(2-nitrophenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-nitrophenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-fluorophenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-chlorophenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(2-naphthylsulfonyl)amino]-2-[(1R,2R)-1,2,3-trihydroxypropyl]-3,4-dihydro-2H-pyran-6-carboxylic acid (2R,3R,4S)-3-(Acetylamino)-4-{[(4-methoxyphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-tert-butylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(1-naphthylsulfonyl)amino]-2-[(1R,2R)-1,2,3-trihydroxypropyl]-3,4-dihydro-2H-pyran-6-carboxylic acid (2R,3R,4S)-3-(Acetylamino)-4-{[(4-carboxyphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-methylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(ethylsulfonyl)amino]-2-[(1R,2R)-1,2,3-trihydroxypropyl]-3,4-dihydro-2H-pyran-6-carboxylic acid (2R,3R,4S)-3-(Acetylamino)-2-[(1R,2R)-1,2,3-trihydroxypropyl]-4-[(vinylsulfonyl)amino]-3,4-dihydro-2H-pyran-6-carboxylic acid (2R,3R,4S)-3-(Acetylamino)-4-({[2-(acetylamino)-4-methyl-1,3-thiazol-5-yl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-({[4-(acetylamino)phenyl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-{[(2-methylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[({4-[(methoxycarbonyl)amino]phenyl}sulfonyl)amino]-2-[(1R,2R)-1,2,3-trihydroxypropyl]-3,4-dihydro-2H-pyran-6-carboxylic acid (2R,3R,4S)-3-(Acetylamino)-4-({[(methylsulfonyl)methyl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-{[(1,2-dimethyl-1H-imidazol-4-yl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-chloro-4-methylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3,5-dimethylisoxazol-4-yl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-carboxy-4-hydroxyphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(dichloromethyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-chloropropyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-isopropylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-ethylphenyl)sulfonyl]amino}-2-[(1R,2R)-1,2,3-trihydroxypropyl]-3,4-dihydro-2H-pyran-6-carboxylic acid (2R,3R,4S)-4-{[(Dichloromethyl)sulfonyl]amino}-3-(isobutyrylamino)-2-[(1R,2R)-1,2,3-trihydroxypropyl]-3,4-dihydro-2H-pyran-6-carboxylic acid (2R,3R,4S)-4-{[(4-Chlorophenyl)sulfonyl]amino}-3-(isobutyrylamino)-2-[(1R,2R)-1,2,3-trihydroxypropyl]-3,4-dihydro-2H-pyran-6-carboxylic acid (2R,3R,4S)-3-(Isobutyrylamino)-4-{[(4-methylphenyl)sulfonyl]amino}-2-[(1R,2R)-1,2,3-trihydroxypropyl]-3,4-dihydro-2H-pyran-6-carboxylic acid (2R,3R,4S)-4-{[(3-Chloro-4-methylphenyl)sulfonyl]amino}-3-(isobutyrylamino)-2-[(1R,2R)-1,2,3-trihydroxypropyl]-3,4-dihydro-2H-pyran-6-carboxylic acid (2R,3R,4S)-3-(Isobutyrylamino)-4-[(thien-2-ylsulfonyl)amino]-2-[(1R,2R)-1,2,3-trihydroxypropyl]-3,4-dihydro-2H-pyran-6-carboxylic acid (2R,3R,4S)-3-(Isobutyrylamino)-4-({[(E)-2-phenylethenyl]sulfonyl}amino)-2-[(1R,2R)-1,2,3-trihydroxypropyl]-3,4-dihydro-2H-pyran-6-carboxylic acid (2R,3R,4S)-3-[(Cyclopropylcarbonyl)amino]-4-{[(dichloromethyl)sulfonyl]amino}-2-[(1R,2R)-1,2,3-trihydroxypropyl]-3,4-dihydro-2H-pyran-6-carboxylic acid (2R,3R,4S)-4-{[(4-Chlorophenyl)sulfonyl]amino}-3-[(cyclopropylcarbonyl)amino]-2-[(1R,2R)-1,2,3-trihydroxypropyl]-3,4-dihydro-2H-pyran-6-carboxylic acid (2R,3R,4S)-3-[(Cyclopropylcarbonyl)amino]-4-{[(4-methylphenyl)sulfonyl]amino}-2-[(1R,2R)-1,2,3-trihydroxypropyl]-3,4-dihydro-2H-pyran-6-carboxylic acid (2R,3R,4S)-4-{[(3-Chloro-4-methylphenyl)sulfonyl]amino}-3-[(cyclopropylcarbonyl)amino]-2-[(1R,2R)-1,2,3-trihydroxypropyl]-3,4-dihydro-2H-pyran-6-carboxylic acid (2R,3R,4S)-3-[(Cyclopropylcarbonyl)amino]-4-({[(E)-2-phenylethenyl]sulfonyl}amino)-2-[(1R,2R)-1,2,3-trihydroxypropyl]-3,4-dihydro-2H-pyran-6-carboxylic acid (2R,3R,4S)-3-[(Cyclopropylcarbonyl)amino]-4-[(thien-2-ylsulfonyl)amino]-2-[(1R,2R)-1,2,3-trihydroxypropyl]-3,4-dihydro-2H-pyran-6-carboxylic acid (2R,3R,4S)-4-Hydroxy-3-[(methylsulfonyl)amino]-2-[(1R,2R)-1,2,3-trihydroxypropyl]-3,4-dihydro-2H-pyran-6-carboxylic acid and pharmaceutically acceptable salts thereof; and prodrugs thereof.

3. A compound according to claim 1 represented by the formulae:

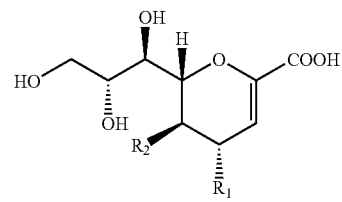

Wherein $R_1$ is selected from the group consisting of:

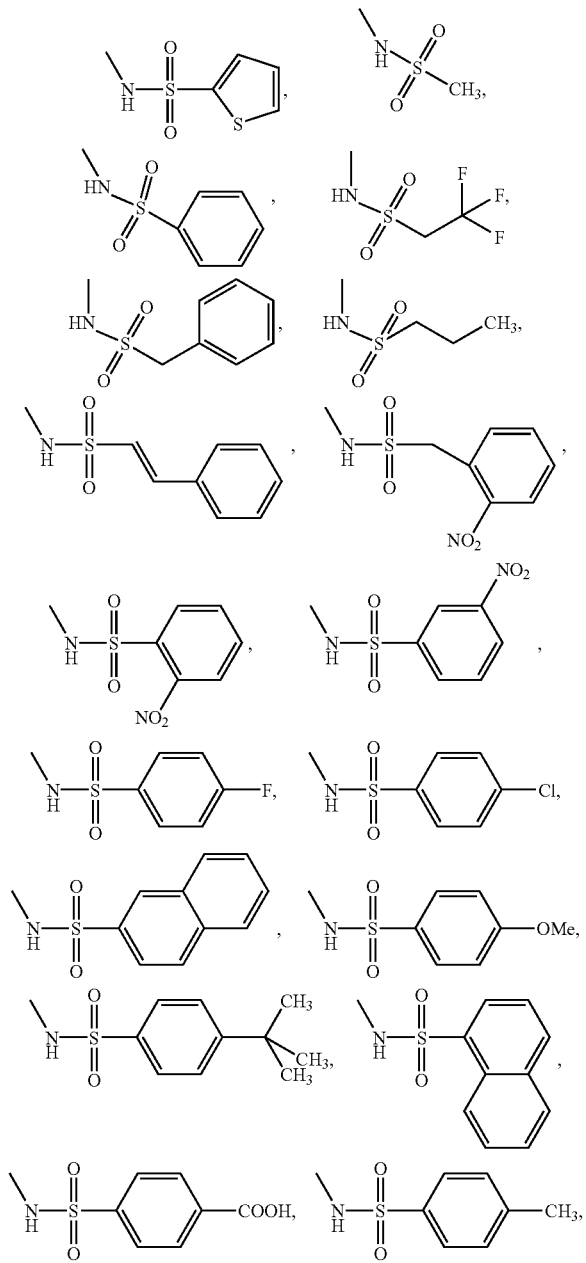

-continued

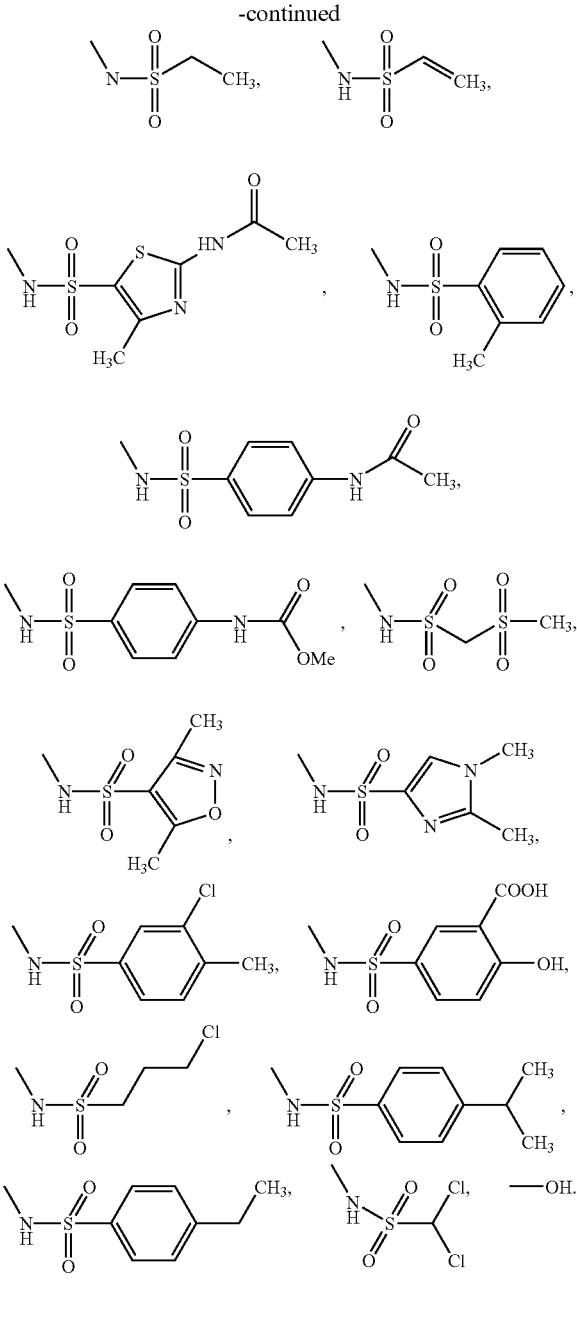

,

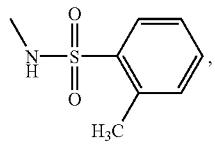

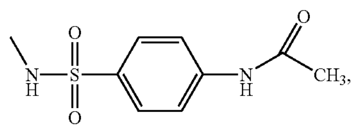

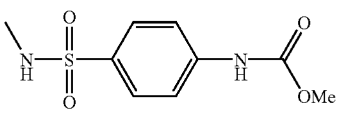

,

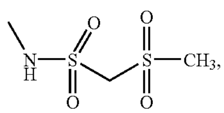

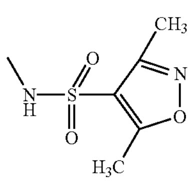

,

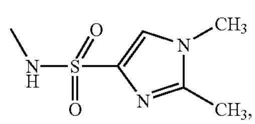

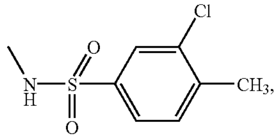

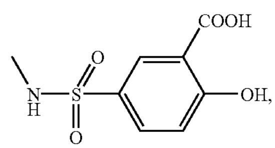

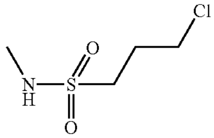

,

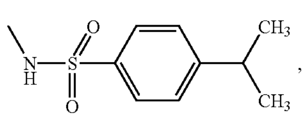

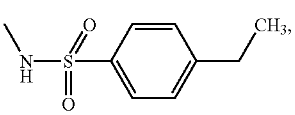

—OH.

Wherein $R_2$ is selected from the group consisting of:

—NHC(O)$CH_3$,

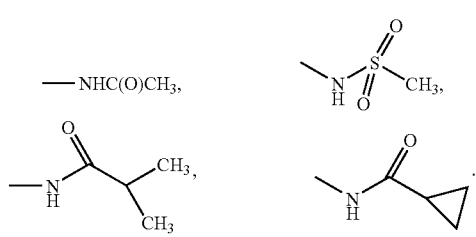

4. A compound according to claim 1 represented by the formulae:

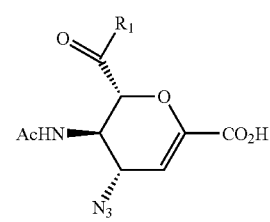

wherein $R_1$ is selected from the group consisting of:

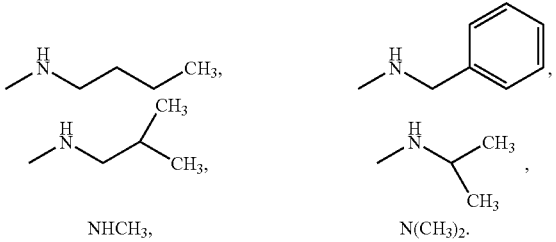

$NHCH_3$, $N(CH_3)_2$.

5. A compound according to claim 1 represented by the formulae:

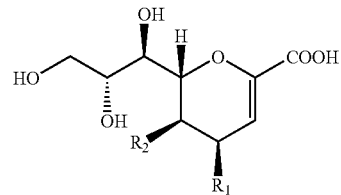

Wherein $R_1$ is selected from the group consisting of:

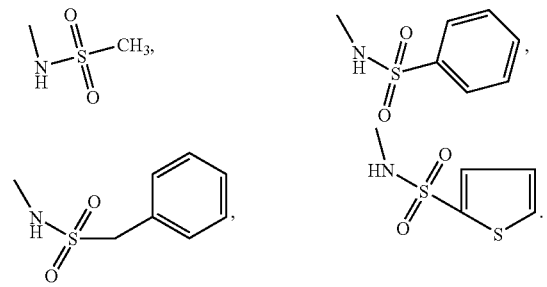

Wherein $R_2$ is —NHC(O)$CH_3$.

6. A composition for inhibiting paramyxovirus neuraminidase, comprising:

A pharmaceutically acceptable carrier and an amount effective for inhibiting influenza virus neuraminidase of a compound according to claim 1.

7. A method of treating paramyxovirus infection comprising:

Administering to a patient in need thereof a composition comprising a pharmaceutically acceptable carrier and an amount effective for inhibiting paramyxovirus neuraminidase of a compound represented by one of the formulas:

A

B

C wherein X is selected from the group consisting of:
  CHR, O, NR, N—OR, NR(O), S, S(O) and S(O)O
  $X_1$ is selected from the group consisting of CR, N, and N(O);
  R is selected from the group consisting of:
  H, alkyl, alkene, alkyne, CN, $NO_2$, $N_3$, halo and $NHR_{10}$;
  $R_1$ is selected from the group consisting of:
  H, $(CH_2)nCO_2R_{10}$, $(CH_2)$n-tetrazol, $(CH_2)nSO_3H$, $(CH_2)nSO_2H$, $(CH_2)nPO_3H_2$, $(CH_2)nCONR_{10}R_{10a}$, $(CH_2)nNO_2$, and $(CH_2)nCHO$;
  $R_{1a}$ is selected from the group consisting of:
  H, $(CH_2)nOR_{10}$, $(CH_2)nCN$, $(CH_2)nNR_{10}R_{10a}$, $(CH_2)nNHC(O)R_{10}$, $(CH_2)nC(O)NR_{10}R_{10a}$, and $(CH_2)nOC(O)R_{10}$;
  $R_1$ and $R_{1a}$ both cannot be H
  each of $R_2$ and $R_{2a}$ is independently selected from the group consisting of H, halo, CN, $(CH_2)nCO_2R_{10}$, $(CH_2)nNR_{10}R_{10a}$ and $(CH_2)_n$—$OR_{10}$;
  each of $R_3$ and $R_{3a}$ is independently selected from the group consisting of:
  H, $NHSO_2R_{10}$, $N(O)$—$SO_2R_{10}$, $NR_{10}SO_2R_{10a}$, $(CH_2)mYR_{10}$, and $(CH_2)mR_6$; provided that when $R_3$ or $R_{3a}$ is $(CH_2)_mYR_{10}$ or $(CH_2)_mR_6$ then m is at least 1 for $R_3$ or $R_{3a}$;
  at least one of $R_3$ and $R_{3a}$ should be other than H
  Y is selected from the group consisting of:
  O, NH, NHC(O), C(O)NH, S, S(O), S(O)O, NHS(O)O, S(O)ONH, NHC(O)NH and heterocycle;
  $R_3$ and $R_{3a}$ together may be
  =O, =$CHR_6$, =$CHR_{10}$, =$NR_{10}$, and =N—$OR_{10}$
  $R_4$ is $(CH_2)mYR_{10}$,
  $R_{4a}$ is selected from the group consisting of:
  H, $(CH_2)mYR_{10}$, and $(CH_2)mR_6$, and
  $R_4$ and $R_{4a}$ together may be:
  =O, =$CHR_6$, =$CHR_{10}$, =$NR_{10}$ and =N—$OR_{10}$
  each of $R_5$ and $R_{5a}$ is independently selected from the group consisting of $C(R_7)(R_{7a})H$, $C(R_7)(R_{7a})C(R_8)(R_{8a})H$, $C(R_7)(R_{7a})C(R_8)(R_{8a})C(R_9)(R_{9a})H$, $OC(R_7)(R_{7a})H$, $OC(R_7)(R_{7a})C(R_8)(R_{8a})H$, $C(R_7)(R_{7a})OC(R_8)(R_{8a})H$, $N(R_{10})C(R_7)(R_{7a})H$, $N(R_{10})C(R_7)(R_{7a})C(R_8)(R_{8a})H$, $C(R_7)(R_{7a})N(R_{10})C(R_8)(R_{8a})H$, and $C(O)NR_{10}R_{10a}$;
  $R_6$ is selected from the group consisting of
  H, halo, CN, $NO_2$, $N_3$, $CO_2R_{10}$, $R_{10}$ and $NR_{10}R_{10a}$;
  $R_7$, $R_8$, $R_{8a}$, $R_9$ and $R_{9a}$ is selected from the group consisting of:
  H, $(CH_2)mYR_{10}$ and $(CH_2)mR_6$
  $R_{7a}$ is $(CH_2)mYR_{10}$
  each of the $R_{10}$ and $R_{10a}$ is individually selected from the groups consisting of:
  H, alkyl, substituted alkyl, aryl, substituted aryl, arylalkyl, substituted arylalkyl, heterocycle, substituted heterocycle, alkenyl, substituted alkenyl, alkynyl, and substituted alkynyl;
  Each of m and n is individually 0, 1, 2, 3, or 4;
  and pharmaceutically acceptable salt thereof, and pro-drugs thereof.

8. A method for inhibiting paramyxovirus neuraminidase, comprising:
  Administering to a patient in need thereof a composition comprising a pharmaceutically acceptable carrier and an amount effective for inhibiting paramyxovirus neuraminidase of a compound represented by on of the formulas:

A

B

C wherein X is selected from the group consisting of:
  CHR, O, NR, N—OR, NR(O), S, S(O) and S(O)O
  $X_1$ is selected from the group consisting of CR, N, and N(O);
  R is selected from the group consisting of:
  H, alkyl, alkene, alkyne, CN, $NO_2$, $N_3$, halo and $NHR_{10}$;
  $R_1$ is selected from the group consisting of:
  H, $(CH_2)nCO_2R_{10}$, $(CH_2)$n-tetrazol, $(CH_2)nSO_3H$, $(CH_2)nSO_2H$, $(CH_2)nPO_3H_2$, $(CH_2)nCONR_{10}R_{10a}$, $(CH_2)nNO_2$, and $(CH_2)nCHO$;
  $R_{1a}$ is selected from the group consisting of:
  H, $(CH_2)nOR_{10}$, $(CH_2)nCN$, $(CH_2)nNR_{10}R_{10a}$, $(CH_2)nNHC(O)R_{10}$, $(CH_2)nC(O)NR_{10}R_{10a}$, and $(CH_2)nOC(O)R_{10}$;
  $R_1$ and $R_{1a}$ both cannot be H each of $R_2$ and $R_{2a}$ is independently selected from the group consisting of H, halo, CN, $(CH_2)nCO_2R_{10}$, $(CH_2)nNR_{10}R_{10a}$ and $(CH_2)_n$—$OR_{10}$;

each of $R_3$ and $R_{3a}$ is independently selected from the group consisting of:

H, $NHSO_2R_{10}$, $N(O)$—$SO_2R_{10}$, $NR_{10}SO_2R_{10a}$, $(CH_2)mYR_{10}$, and $(CH_2)mR_6$; provided that when $R_3$ or $R_{3a}$ is $(CH_2)_mYR_{10}$ or $(CH_2)_mR_6$ then m is at least 1 for $R_3$ or $R_{3a}$;

at least one of $R_3$ and $R_{3a}$ should be other than H

Y is selected from the group consisting of:

O, NH, NHC(O), C(O)NH, S, S(O), S(O)O, NHS(O)O, S(O)ONH, NHC(O)NH and heterocycle;

$R_3$ and $R_{3a}$ together may be

=O, =$CHR_6$, =$CHR_{10}$, =$NR_{10}$, and =N—$OR_{10}$ $R_4$ is $(CH_2)mYR_{10}$, $R_{4a}$ is selected from the group consisting of:

H, $(CH_2)mYR_{10}$ and $(CH_2)mR_6$, and $R_4$ and $R_{4a}$ together may be:

=O, =$CHR_6$, =$CHR_{10}$, =$NR_{10}$ and =N—$OR_{10}$ each of $R_5$ and $R_{5a}$ is independently selected from the group consisting of $C(R_7)(R_{7a})H$, $C(R_7)(R_{7a})C(R_8)(R_{8a})H$, $C(R_7)(R_{7a})C(R_8)(R_{8a})C(R_9)(R_{9a})H$, $OC(R_7)(R_{7a})H$, $OC(R_7)(R_{7a})C(R_8)(R_{8a})H$, $C(R_7)(R_{7a})OC(R_8)(R_{8a})H$, $N(R_{10})C(R_7)(R_{7a})H$, $N(R_{10})C(R_7)(R_{7a})C(R_8)(R_{8a})H$, $C(R_7)(R_{7a})N(R_{10})C(R_8)(R_{8a})H$, and $C(O)NR_{10}R_{10a}$;

$R_6$ is selected from the group consisting of

H, halo, CN, $NO_2$, $N_3$, $CO_2R_{10}$, $R_{10}$ and $NR_{10}R_{10a}$;

$R_7$, $R_8$, $R_{8a}$, $R_9$ and $R_{9a}$ is selected from the group consisting of:

H, $(CH_2)mYR_{10}$ and $(CH_2)mR_6$ $R_{7a}$ is $(CH_2)mYR_{10}$ each of the $R_{10}$ and $R_{10a}$ is individually selected from the groups consisting of:

H, alkyl, substituted alkyl, aryl, substituted aryl, arylalkyl, substituted arylalkyl, heterocycle, substituted heterocycle, alkenyl, substituted alkenyl, alkynyl, and substituted alkynyl;

Each of m and n is individually 0, 1, 2, 3, or 4 and pharmaceutically acceptable salt thereof; and pro-drugs thereof.

9. The method of claim 7 or 8 wherein the compound is selected from the group consisting of:

(2R,3R,4S)-3-(Acetylamino)-4-(benzoylamino)-2-[(1R,2R)-1,2,3-trihydroxypropyl]-3,4-dihydro-2H-pyran-6-carboxylic acid (2R,3R,4S)-3-(Acetylamino)-4-[(3-methylbutanoyl)amino]-2-[(1R,2R)-1,2,3-trihydroxypropyl]-3,4-dihydro-2H-pyran-6-carboxylic acid (2R,3R,4S)-3-(Acetylamino)-4-(2-furoylamino)-2-[(1R,2R)-1,2,3-trihydroxypropyl]-3,4-dihydro-2H-pyran-6-carboxylic acid (2R,3R,4S)-3,4-Bis(acetylamino)-2-[(1R,2R)-1,2,3-trihydroxypropyl]-3,4-dihydro-2H-pyran-6-carboxylic acid (2R,3R,4S)-3-(Acetylamino)-4-[(thien-2-ylacetyl)amino]-2-[(1R,2R)-1,2,3-trihydroxypropyl]-3,4-dihydro-2H-pyran-6-carboxylic acid (2R,3R,4S)-3-(Acetylamino)-4-[(thien-2-ylcarbonyl)amino]-2-[(1R,2R)-1,2,3-trihydroxypropyl]-3,4-dihydro-2H-pyran-6-carboxylic acid (2R,3R,4S)-3-(Acetylamino)-4-[(thien-3-ylacetyl)amino]-2-[(1R,2R)-1,2,3-trihydroxypropyl]-3,4-dihydro-2H-pyran-6-carboxylic acid (2R,3R,4S)-3-(Acetylamino)-4-[(phenylacetyl)amino]-2-[(1R,2R)-1,2,3-trihydroxypropyl]-3,4-dihydro-2H-pyran-6-carboxylic acid (2R,3R,4S)-3-(Acetylamino)-4-[(thien-2-ylmethyl)amino]-2-[(1R,2R)-1,2,3-trihydroxypropyl]-3,4-dihydro-2H-pyran-6-carboxylic acid (2R,3R,4S)-3-(Acetylamino)-4-[(4-chlorobenzyl)amino]-2-[(1R,2R)-1,2,3-trihydroxypropyl]-3,4-dihydro-2H-pyran-6-carboxylic acid (2R,3R,4S)-3-(Acetylamino)-4-(benzylamino)-2-[(1R,2R)-1,2,3-trihydroxypropyl]-3,4-dihydro-2H-pyran-6-carboxylic acid 1-{(2R,3R,4S)-3-(Acetylamino)-6-carboxy-2-[(1R,2R)-1,2,3-trihydroxypropyl]-3,4-dihydro-2H-pyran-4yl}-1H-1,2,3-triazole-4-carboxylic acid (2R,3R,4S)-3-(Acetylamino)-4-[(1-ethylpropyl)amino]-2-[(1R,2R)-1,2,3-trihydroxypropyl]-3,4-dihydro-2H-pyran-6-carboxylic acid (2R,3R,4S)-3-(Acetylamino)-4-(isopropylamino)-2-[(1R,2R)-1,2,3-trihydroxypropyl]-3,4-dihydro-2H-pyran-6-carboxylic acid (2R,3R,4S)-3-(Acetylamino)-4-(sec-butylamino)-2-[(1R,2R)-1,2,3-trihydroxypropyl]-3,4-dihydro-2H-pyran-6-carboxylic acid (2R,3R,4S)-3-(Acetylamino)-4-[(1,3-dimethylbutyl)amino]-2-[(1R,2R)-1,2,3-trihydroxypropyl]-3,4-dihydro-2H-pyran-6-carboxylic acid (2R,3R,4S)-3-(Acetylamino)-4-[(1-methylpentyl)amino]-2-[(1R,2R)-1,2,3-trihydroxypropyl]-3,4-dihydro-2H-pyran-6-carboxylic acid (2R,3R,4S)-3-(Acetylamino)-4-[(1-isopropylbutyl)amino]-2-[(1R,2R)-1,2,3-trihydroxypropyl]-3,4-dihydro-2H-pyran-6-carboxylic acid (2R,3R,4S)-3-(Acetylamino)-4-[(1,4-dimethylpentyl)amino]-2-[(1R,2R)-1,2,3-trihydroxypropyl]-3,4-dihydro-2H-pyran-6-carboxylic acid (2R,3R,4S)-3-(Acetylamino)-4-[(3-carboxy-1-methylpropyl)amino]-2-[(1R,2R)-1,2,3-trihydroxypropyl]-3,4-dihydro-2H-pyran-6-carboxylic acid (2R,3R,4S)-3-(Acetylamino)-4-[(1,2-dimethylbutyl)amino]-2-[(1R,2R)-1,2,3-trihydroxypropyl]-3,4-dihydro-2H-pyran-6-carboxylic acid (2R,3R,4S)-3-(Acetylamino)-4-[(1-benzylpropyl)amino]-2-[(1R,2R)-1,2,3-trihydroxypropyl]-3,4-dihydro-2H-pyran-6-carboxylic acid (2R,3R,4S)-3-(Acetylamino)-4-[(2-methylbutyl)amino]-2-[(1R,2R)-1,2,3-trihydroxypropyl]-3,4-dihydro-2H-pyran-6-carboxylic acid (2R,3R,4S)-3-(Acetylamino)-4-[(3-phenylbutyl)amino]-2-[(1R,2R)-1,2,3-trihydroxypropyl]-3,4-dihydro-2H-pyran-6-carboxylic acid (2R,3R,4S)-3-(Acetylamino)-4-(isobutylamino)-2-[(1R,2R)-1,2,3-trihydroxypropyl]-3,4-dihydro-2H-pyran-6-carboxylic acid (2R,3R,4S)-3-(Acryloylamino)-4-hydroxy-2-[(1R,2R)-1,2,3-trihydroxypropyl]-3,4-dihydro-2H-pyran-6-carboxylic acid (2R,3R,4S)-3-[(Cyclobutylcarbonyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(propionylamino)-2-[(1R,2R)-1,2,3-trihydroxypropyl]-3,4-dihydro-2H-pyran-6-carboxylic acid (2R,3R,4S)-3-[(Cyclopentylcarbonyl)amino]-4-hydroxy-2-[(1R,2R)-1,2,3-trihydroxypropyl]-3,4-dihydro-2H-pyran-6-carboxylic acid (2R,3R,4S)-3-(2-Furoylamino)-4-hydroxy-2-[(1R,2R)-1,2,3-trihydroxypropyl]-3,4-dihydro-2H-pyran-6-carboxylic acid (2R,3R,4S)-4-Hydroxy-3-[(thien-2-ylcarbonyl)amino]-2-[(1R,2R)-1,2,3-trihydroxypropyl]-3,4-dihydro-2H-pyran-6-carboxylic acid (2R,3R,4S)-3-(Butyrylamino)-4-hydroxy-2-[(1R,2R)-1,2,3-trihydroxypropyl]-3,4-dihydro-2H-pyran-6-carboxylic acid (2R,3R,4S)-4-Hydroxy-3-[(3-methylbutanoyl)amino]-2-[(1R,2R)-1,2,3-trihydroxypropyl]-3,4-dihydro-2H-pyran-6-carboxylic acid (2R,3R,4S)-3-[(Cyclopropylcarbonyl)amino]-4-hydroxy-2-[(1R,2R)-1,2,3-trihydroxypropyl]-3,4-dihydro-2H-pyran-6-carboxylic acid (2R,3R,4S)-3-[(3,3-Dimethylbutanoyl)amino]-4-hydroxy-2-[(1R,2R)-1,2,3-trihydroxypropyl]-3,4-dihydro-2H-pyran-6-carboxylic acid (2R,3R,4S)-3-(Benzoylamino)-4-hydroxy-2-[(1R,2R)-1,2,3-trihydroxypropyl]-3,4-dihydro-2H-pyran-6-carboxylic acid (2R,3R,4S)-4-Hydroxy-3-(isobutyrylamino)-2-[(1R,2R)-1,2,3-trihydroxypropyl]-3,4-dihydro-2H-pyran-6-carboxylic acid (2R,3R,4S)-3-[(tert-Butoxycarbonyl)amino]-4-hydroxy-2-[(1R,2R)-1,2,3-trihydroxypropyl]-3,4-dihydro-2H-pyran-6-carboxylic acid (2R,3R,4S)-3-[(2,2-Dimethylpropanoyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-[(3-phenylpropanoyl)amino]-2-[(1R,2R)-1,2,3-trihydroxypropyl]-3,4-dihydro-2H-pyran-6-carboxylic acid (2R,3R,4S)-3-[(2-Chloropropanoyl)amino]-4-hydroxy-2-[(1R,2R)-1,2,3-trihydroxypropyl]-3,4-dihydro-2H-pyran-6-carboxylic acid (2R,3R,4S)-3-[(Chloroacetyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(methacryloylamino)-2-[(1R,2R)-1,2,3-trihydroxypropyl]-3,4-dihydro-2H-pyran-6-carboxylic acid (2R,3R,4S)-3-[(2-Ethylbutanoyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-[(phenylacetyl)amino]-2-[(1R,2R)-1,2,3-trihydroxypropyl]-3,4-dihydro-2H-pyran-6-carboxylic acid (2R,3R,4S)-4-Hydroxy-3-[(3-methylbut-2-enoyl)amino]-2-[(1R,2R)-1,2,3-trihydroxypropyl]-3,4-dihydro-2H-pyran-6-carboxylic acid (2R,3R,4S)-4-Hydroxy-3-[(thien-2-ylacetyl)amino]-2-[(1R,2R)-1,2,3-trihydroxypropyl]-3,4-dihydro-2H-pyran-6-carboxylic acid (2R,3R,4S)-4-Hydroxy-3-[(2-methylbutanoyl)amino]-2-[(1R,2R)-1,2,3-trihydroxypropyl]-3,4-dihydro-2H-pyran-6-carboxylic acid (2R,3R,4S)-3-[(4-Chlorobutanoyl)amino]-4-hydroxy-2-[(1R,2R)-1,2,3-trihydroxypropyl]-3,4-dihydro-2H-pyran-6-carboxylic acid (2R,3R,4S)-3-[(5-Chloropentanoyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(2-oxopiperidin-1-yl)-2-[(1R,2R)-1,2,3-trihydroxypropyl]-3,4-dihydro-2H-pyran-6-carboxylic acid (2R,3R,4S)-4-Hydroxy-3-(2-oxopyrrolidin-1-yl)-2-[(1R,2R)-1,2,3-trihydroxypropyl]-3,4-dihydro-2H-pyran-6-carboxylic acid (2R,3R,4S)-3-[(1-Ethylpropyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(isopropylamino)-2-[(1R,2R)-1,2,3-trihydroxypropyl]-3,4-dihydro-2H-pyran-6-carboxylic acid (2R,3R,4S)-3-[(1,3-Dimethylbutyl)amino]-4-hydroxy-2-[(1R,2R)-1,2,3-trihydroxypropyl]-3,4-dihydro-2H-pyran-6-carboxylic acid (2R,3R,4S)-3-(Diethylamino)-4-hydroxy-2-[(1R,2R)-1,2,3-trihydroxypropyl]-3,4-dihydro-2H-pyran-6-carboxylic acid (2R,3R,4S)-3-(sec-Butylamino)-4-hydroxy-2-[(1R,2R)-1,2,3-trihydroxypropyl]-3,4-dihydro-2H-pyran-6-carboxylic acid (2R,3R,4S)-3-[(1,4-Dimethylpentyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-[(1-methylpentyl)amino]-2-[(1R,2R)-1,2,3-trihydroxypropyl]-3,4-dihydro-2H-pyran-6-carboxylic acid (2R,3R,4S)-4-Hydroxy-3-[(2-hydroxy-1-methylethyl)amino]-2-[(1R,2R)-1,2,3-trihydroxypropyl]-3,4-dihydro-2H-pyran-6-carboxylic acid (2R,3R,4S)-3-[(1-Benzylpropyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(isopentylamino)-2-[(1R,2R)-1,2,3-trihydroxypropyl]-3,4-dihydro-2H-pyran-6-carboxylic acid (2R,3R,4S)-3-[(3,3-Dimethylbutyl)amino]-4-hydroxy-2-[(1R,2R)-1,2,3-trihydroxypropyl]-3,4-dihydro-2H-pyran-6-carboxylic acid (2R,3R,4S)-3-(Butylamino)-4-hydroxy-2-[(1R,2R)-1,2,3-trihydroxypropyl]-3,4-dihydro-2H-pyran-6-carboxylic acid (2R,3R,4S)-3-[(1,2-Dimethylbutyl)amino]-4-hydroxy-2-[(1R,2R)-1,2,3-trihydroxypropyl]-3,4-dihydro-2H-pyran-6-carboxylic acid (2R,3R,4S)-4-Hydroxy-3-(isobutylamino)-2-[(1R,2R)-1,2,3-trihydroxypropyl]-3,4-dihydro-2H-pyran-6-carboxylic acid (2R,3R,4S)-4-Hydroxy-3-pyrrolidin-1-yl-2-[(1R,2R)-1,2,3-trihydroxypropyl]-3,4-dihydro-2H-pyran-6-carboxylic acid (2R,3R,4S)-4-Hydroxy-3-(neopentylamino)-2-[(1R,2R)-1,2,3-trihydroxypropyl]-3,4-dihydro-2H-pyran-6-carboxylic acid (2R,3R,4S)-4-Azido-3-[(2-methylbutanoyl)amino]-2-[(1R,2R)-1,2,3-trihydroxypropyl]-3,4-dihydro-2H-pyran-6-carboxylic acid (2R,3R,4S)-4-Azido-3-(isobutylamino)-2-[(1R,2R)-1,2,3-trihydroxypropyl]-3,4-dihydro-2H-pyran-6-carboxylic acid (2R,3R,4S)-4-Azido-3-(isobutyrylamino)-2-[(1R,2R)-1,2,3-trihydroxypropyl]-3,4-dihydro-2H-pyran-6-carboxylic acid (2R,3R,4S)-4-Azido-3-[(cyclopropylcarbonyl)amino]-2-[(1R,2R)-1,2,3-trihydroxypropyl]-3,4-dihydro-2H-pyran-6-carboxylic acid (2R,3R,4S)-4-Azido-3-[(cyclobutylcarbonyl)amino]-2-[(1R,2R)-1,2,3-trihydroxypropyl]-3,4-dihydro-2H-pyran-6-carboxylic acid (2R,3R,4S)-4-(Benzylamino)-3-(isobutyrylamino)-2-[(1R,2R)-1,2,3-trihydroxypropyl]-3,4-dihydro-2H-pyran-6-carboxylic acid (2R,3R,4S)-4-[(4-Chlorobenzyl)amino]-3-(isobutyrylamino)-2-[(1R,2R)1,2,3-trihydroxypropyl]-3,4-dihydro-2H-pyran-6-carboxylic acid (2R,3R,4S)-3-(Isobutyrylamino)-4-[(thien-2-ylmethyl)amino]-2-[(1R,2R)-1,2,3-trihydroxypropyl]-3,4-dihydro-2H-pyran-6-carboxylic acid (2R,3R,4S)-3-(Acetylamino)-4-(1H-1,2,3-triazol-1-yl)-2-[(1R,2R)-1,2,3-trihydroxypropyl]-3,4-dihydro-2H-pyran-6-carboxylic acid (2R,3R,4S)-3-(Acetylamino)-4-[(4-chlorobenzyl)oxy-2-[(1R,2R)-1,2,3-trihydroxypropyl]-3,4-dihydro-2H-pyran-6-carboxylic acid (2R,3R,4S)-3-(Acetylamino)-4-butoxy-2-[(1R,2R)-1,2,3-trihydroxypropyl]-3,4-dihydro-2H-pyran-6-carboxylic acid (2R,3R,4S)-3-(Acetylamino)-4-(pent-4-enyloxy)-2-[(1R,2R)-1,2,3-trihydroxypropyl]-3,4-dihydro-2H-pyran-6-carboxylic acid (2R,3R,4S)-3-(Acetylamino)-4-(hex-5-enyloxy)-2-[(1R,2R)-1,2,3-trihydroxypropyl]-3,4-dihydro-2H-pyran-6-carboxylic acid (2R,3R,4S)-3-(Acetylamino)-4-(3-bromopropoxy)-2-[(1R,2R)-1,2,3-trihydroxypropyl]-3,4-dihydro-2H-pyran-6-carboxylic acid (2R,3R,4S)-3-(Acetylamino)-4-(but-2-ynyloxy)-2-[(1R,2R)-1,2,3-trihydroxypropyl]-3,4-dihydro-2H-pyran-6-carboxylic acid (2R,3R,4S)-3-(Acetylamino)-4-[(2-methylprop-2-enyl)oxy]-2-[(1R,2R)-1,2,3-trihydroxypropyl]-3,4-dihydro-2H-pyran-6-carboxylic acid (2R,3R,4S)-3-(Acetylamino)-4-[(2E)-but-2-enyloxy]-2-[(1R,2R)-1,2,3-trihydroxypropyl]-3,4-dihydro-2H-pyran-6-carboxylic acid (2R,3R,4S)-3-(Acetylamino)-4-(3-chloropropoxy)-2-[(1R,2R)-1,2,3-trihydroxypropyl]-3,4-dihydro-2H-pyran-6-carboxylic acid (2R,3R,4S)-3-(Acetylamino)-4-[(2-ethylhexyl)oxy]-2-[(1R,2R)-1,2,3-trihydroxypropyl]-3,4-dihydro-2H-pyran-6-carboxylic acid (2R,3R,4S)-3-(Acetylamino)-4-isobutoxy-2-[(1R,2R)-1,2,3-trihydroxypropyl]-3,4-dihydro-2H-pyran-6-carboxylic acid (2R,3R,4S)-3-(Acetylamino)-4-(cyclohexylmethoxy)-2-[(1R,2R)-1,2,3-trihydroxypropyl]-3,4-dihydro-2H-pyran-6-carboxylic acid (2R,3R,4S)-3-(Acetylamino)-4-(carboxymethoxy)-2-[(1R,2R)-1,2,3-trihydroxypropyl]-3,4-dihydro-2H-pyran-6-carboxylic acid (2R,3R,4S)-3-(Acetylamino)-4-(2-oxobutoxy)-2-[(1R,2R)-1,2,3-trihydroxypropyl]-3,4-dihydro-2H-pyran-6-carboxylic acid (2R,3R,4S)-3-(Acetylamino)-4-[(2-carboxyprop-2-enyl)oxy]-2-[(1R,2R)-1,2,3-trihydroxypropyl]-3,4-dihydro-2H-pyran-6-carboxylic acid (2R,3R,4S)-3-(Acetylamino)-4-(2-methoxyethoxy)-2-[(1R,2R)-1,2,3-trihydroxypropyl]-3,4-dihydro-2H-pyran-6-carboxylic acid (2R,3R,4S)-3-(Acetylamino)-4-[(2E)-pent-2-enyloxy]-2-[(1R,2R)-1,2,3-trihydroxypropyl]-3,4-dihydro-2H-pyran-6-carboxylic acid (2R,3R,4S)-3-(Acetylamino)-4-(cyclopropylmethoxy)-2-[(1R,2R)-1,2,3-trihydroxypropyl]-3,4-dihydro-2H-pyran-6-carboxylic acid (2R,3R,4S)-3-(Acetylamino)-4-ethoxy-2-[(1R,2R)-1,2,3-trihydroxypropyl]-3,4-dihydro-2H-pyran-6-carboxylic acid (2R,3R,4S)-3-(Acetylamino)-4-(benzyloxy)-2-[(1R,2R)-1,2,3-trihydroxypropyl]-3,4-dihydro-2H-pyran-6-carboxylic acid (2R,3R,4S)-3-(acetylamino)-4-propoxy-2-[(1R,2R)-1,2,3-trihydroxypropyl]-3,4-dihydro-2H-pyran-6-carboxylic acid (2R,3R,4S)-3-(Acetylamino)-4-(allyloxy)-2-[(1R,2R)-1,2,3-trihydroxypropyl]-3,4-dihydro-2H-pyran-6-carboxylic acid (2R,3R,4S)-3-(Acetylamino)-4-methoxy-2-[(1R,2R)-1,2,3-trihydroxypropyl]-3,4-dihydro-2H-pyran-6-carboxylic acid (2R,3R,4R)-4-(Benzyloxy)-3-(isobutyrylamino)-2-[(1R,2R)-1,2,3-trihydroxypropyl]-3,4-dihydro-2H-pyran-6-carboxylic acid (2R,3R,4R)-4-[(4-Chlorobenzyl)oxy]-3-(isobutyrylamino)-2-[(1R,2R)-1,2,3-trihydroxypropyl]-3,4-dihydro-2H-pyran-6-carboxylic acid (2R,3R,4R)-3-(Isobutyrylamino)-4-{[(2E)-3-phenylprop-2-enyl]oxy}-2-[(1R,2R)-1,2,3-trihydroxypropyl]-3,4-dihydro-2H-pyran-6-carboxylic acid (2R,3R,4R)-4-(Allyloxy)-3-(isobutyrylamino)-2-[(1R,2R)-1,2,3-trihydroxypropyl]-3,4-dihydro-2H-pyran-6-carboxylic acid (2R,3R,4R)-4-Isobutoxy-3-(isobutyrylamino)-2-[(1R,2R)-1,2,3-trihydroxypropyl]-3,4-dihydro-2H-pyran-6-carboxylic acid (2R,3R,4R)-3-(Isobutyrylamino)-4-propoxy-2-[(1R,2R)-1,2,3-trihydroxypropyl]-3,4-dihydro-2H-pyran-6-carboxylic acid (2R,3R,4R)-3-(Isobutyrylamino)-4-methoxy-2-[(1R,2R)-1,2,3-trihydroxypropyl]-3,4-dihydro-2H-pyran-6-carboxylic acid (2R,3R,4R)-4-Ethoxy-3-(isobutyrylamino)-2-[(1R,2R)-1,2,3-trihydroxypropyl]-3,4-dihydro-2H-pyran-6-carboxylic acid (2R,3R,4R)-3-(Isobutyrylamino)-4-(thien-2-ylmethoxy)-2-[(1R,2R)-1,2,3-trihydroxypropyl]-3,4-dihydro-2H-pyran-6-carboxylic acid (2R,3R,4S)-3-(Acetylamino)-4-methoxy-2-[(1R,2R)-1,2,3-trihydroxypropyl]-3,4-dihydro-2H-pyran-6-carboxylic acid (2R,3R,4S)-3-(Acetylamino)-4-azido-2-[(butylamino)carbonyl]-3,4-dihydro-2H-pyran-6-carboxylic acid (2R,3R,4S)-3-(Acetylamino)-4-azido-2-[(isobutylamino)carbonyl]-3,4-dihydro-2H-pyran-6-carboxylic acid (2R,3R,4S)-3-(Acetylamino)-4-azido-2-[(dimethylamino)carbonyl]-3,4-dihydro-2H-pyran-6-carboxylic acid (2R,3R,4S)-3-(Acetylamino)-4-azido-2-[(benzylamino)carbonyl]-3,4-dihydro-2H-pyran-6-carboxylic acid (2R,3R,4S)-3-(Acetylamino)-4-azido-2-[(isopropylamino)carbonyl]-3,4-dihydro-2H-pyran-6-carboxylic acid (2R,3R,4S)-3-(Acetylamino)-4-azido-2-[(methylamino)carbonyl]-3,4-dihydro-2H-pyran-6-carboxylic acid (2R,3R,4S)-3-(Acetylamino)-4-[(thien-2-ylsulfonyl)amino]-2-[(1R,2R)-1,2,3-trihydroxypropyl]-3,4-dihydro-2H-pyran-6-carboxylic acid (2R,3R,4S)-3-(Acetylamino)-4-[(methylsulfonyl)amino]-2-[(1R,2R)-1,2,3-trihydroxypropyl]-3,4-dihydro-2H-pyran-6-carboxylic acid (2R,3R,4S)-3-(Acetylamino)-4-[(phenylsulfonyl)amino]-2-[(1R,2R)-1,2,3-trihydroxypropyl]-3,4-dihydro-2H-pyran-6-carboxylic acid (2R,3R,4S)-3-(Acetylamino)-4-{[(2,2,2-trifluoroethyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(benzylsulfonyl)amino]-2-[(1R,2R)-1,2,3-trihydroxypropyl]-3,4-dihydro-2H-pyran-6-carboxylic acid (2R,3R,4S)-3-(Acetylamino)-4-[(propylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(methylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(phenylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(benzylsulfonyl)amino]-2-[(1R,2R)-1,2,3-trihydroxypropyl]-3,4-dihydro-2H-pyran-6-carboxylic acid (2R,3R,4R)-3-(Acetylamino)-4-[(thien-2-ylsulfonyl)amino]-2-[(1R,2R)-1,2,3-trihydroxypropyl]-3,4-dihydro-2H-pyran-6-carboxylic acid (2R,3R,4S)-3-(Acetylamino)-4-({[(E)-2-phenylethenyl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-{[(2-nitrobenzyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(2-nitrophenyl)sulfonyl]amino}-2-[(1R,1,2,3-trihydroxypropyl]-3,4-dihydro-2H-pyran-6-carboxylic acid (2R,3R,4S)-3-(Acetylamino)-4-{[(3-nitrophenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-fluorophenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-chlorophenyl)sulfonyl]amino}-2-[(1R,2R)-1,2,3-trihydroxypropyl]-3,4-dihydro-2H-pyran-6-carboxylic acid (2R, 3R,4S)-3-(Acetylamino)-4-[(2-naphthylsulfonyl)amino]-2-[(1R,2R)-1,2,3-trihydroxypropyl]-3,4-dihydro-2H-pyran-6-carboxylic acid (2R,3R,4S)-3-(Acetylamino)-4-{[(4-methoxyphenyl)sulfonyl]amino}-2-[(1,2,3-trihydroxypropyl]-3,4-dihydro-2H-pyran-6-carboxylic acid (2R,3R,4S)-3-(Acetylamino)-4-{[(4-tert-butylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(1-naphthylsulfonyl)amino]-2-[(1R,2R)-1,2,3-trihydroxypropyl]-3,4-dihydro-2H-pyran-6-carboxylic acid (2R,3R,4S)-3-(Acetylamino)-4-{[(4-carboxyphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-methylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[(ethylsulfonyl)amino]-2-[(1R,2R)-1,2,3-trihydroxypropyl]-3,4-dihydro-2H-pyran-6-carboxylic acid (2R,3R,4S)-3-(Acetylamino)-2-[(1R,2R)-1,2,3-trihydroxypropyl]-4-[(vinylsulfonyl)amino]-3,4-dihydro-2H-pyran-6-carboxylic acid (2R,3R,4S)-3-(Acetylamino)-4-({[2-(acetylamino)-4-methyl-1,3-thiazol-5-yl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-({[4-(acetylamino)phenyl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-{[(2-methylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-[({4-[(methoxycarbonyl)amino]phenyl}sulfonyl)amino]-2-[(1R,2R)-1,2,3-trihydroxypropyl]-3,4-dihydro-2H-pyran-6-carboxylic acid (2R,3R,4S)-3-(Acetylamino)-4-({[(methylsulfonyl)methyl]sulfonyl}amino)-2-[(1R,2R)-1,2,3-trihydroxypropyl]-3,4-dihydro-2H-pyran-6-carboxylic acid (2R,3R,4S)-3-(Acetylamino)-4-{[(1,2-dimethyl-1H-imidazol-4-yl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-chloro-4-methylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3,5-dimethylisoxazol-4-yl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-carboxy-4-hydroxyphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(dichloromethyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(3-chloropropyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-isopropylphenyl)sulfonyl]amino}-2-[(1R,2R)-1,2,3-trihydroxypropyl]-3,4-dihydro-2H-pyran-6-carboxylic acid (2R,3R,4S)-3-(Acetylamino)-4-{[(4-ethylphenyl) sulfonyl]amino}-2-[(1R,2R) -trihydroxypropyl]-3,4-dihydro-2H-pyran-6-carboxylic acid (2R,3R,4S)-4-{[(Dichloromethyl)sulfonyl]amino}-3-(isobutyrylamino)-2-[(1R,2R)-1,2,3-trihydroxypropyl]-3,4-dihydro-2H-pyran-6-carboxylic acid (2R,3R,4S)-4-{[(4-Chlorophenyl)sulfonyl]amino}-3-(isobutyrylamino)-2-[(1R,2R)-1,2,3-trihydroxypropyl]-3,4-dihydro-2H-pyran-6-carboxylic acid (2R,3R,4S)-3-(Isobutyrylamino)-4-{[(4-methylphenyl) sulfonyl]amino}-2-[(1R,2R)-1,2,3-trihydroxypropyl]-3,4-dihydro-2H-pyran-6-carboxylic acid (2R,3R,4S)-4-{[(3-Chloro-4-methylphenyl)sulfonyl] amino}-3-(isobutyrylamino)-2-[(1R,2R)-1,2,3-trihydroxypropyl]-3,4-dihydro-2H-pyran-6-carboxylic acid (2R,3R,4S)-3-(Isobutyrylamino)-4-[(thien-2-ylsulfonyl) amino]-2-[(1R,2R)-1,2,3-trihydroxypropyl]-3,4-dihydro-2H-pyran-6-carboxylic acid (2R,3R,4S)-3-(Isobutyrylamino)-4-({[(E)-2-phenylethenyl]sulfonyl}amino)-2-[(1R,2R)-1,2,3-trihydroxypropyl]-3,4-dihydro-2H-pyran-6-carboxylic acid (2R,3R,4S)-3-[(Cyclopropylcarbonyl)amino]-4-{[(dichloromethyl)sulfonyl]amino}-2-[(1R,2R)-1,2,3-trihydroxypropyl]-3,4-dihydro-2H-pyran-6-carboxylic acid (2R,3R,4S)-4-{[(4-Chlorophenyl)sulfonyl]amino}-3-[(cyclopropylcarbonyl)amino]-2-[(1R,2R)-1,2,3-trihydroxypropyl]-3,4-dihydro-2H-pyran-6-carboxylic acid (2R,3R,4S)-3-[(Cyclopropylcarbonyl)amino]-4-{[(4-methylphenyl)sulfonyl]amino}-2-[(1R,2R)-1,2,3-trihydroxypropyl]-3,4-dihydro-2H-pyran-6-carboxylic acid (2R,3R,4S)-4-{[(3-Chloro-4-methylphenyl)sulfonyl] amino}-3-[(cyclopropylcarbonyl)amino]-2-[(1R,2R)-1,2,3-trihydroxypropyl]-3,4-dihydro-2H-pyran-6-carboxylic acid (2R,3R,4S)-3-[(Cyclopropylcarbonyl)amino]-4-({[(E)-2-phenylethenyl]sulfonyl}amino)-2-[(1R,2R)-1,2,3-trihydroxypropyl]-3,4-dihydro-2H-pyran-6-carboxylic acid (2R,3R,4S)-3-[(Cyclopropylcarbonyl)amino]-4-[(thien-2-ylsulfonyl)amino]-2-[(1R,2R)-1,2,3-trihydroxypropyl]-3,4-dihydro-2H-pyran-6-carboxylic acid (2R,3R,4S)-4-Hydroxy-3-[(methylsulfonyl)amino]-2-[(1R,2R)-1,2,3-trihydroxypropyl]-3,4-dihydro-2H-pyran-6-carboxylic acid and pharmaceutically acceptable salt thereof; and pro-drugs thereof.

10. A method according to claim 7 or 8 wherein the compound is represented by the formulae:

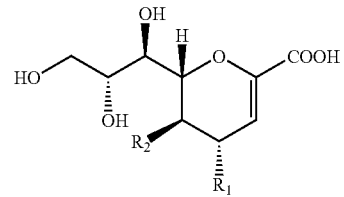

Wherein $R_1$ is selected from the group consisting of:

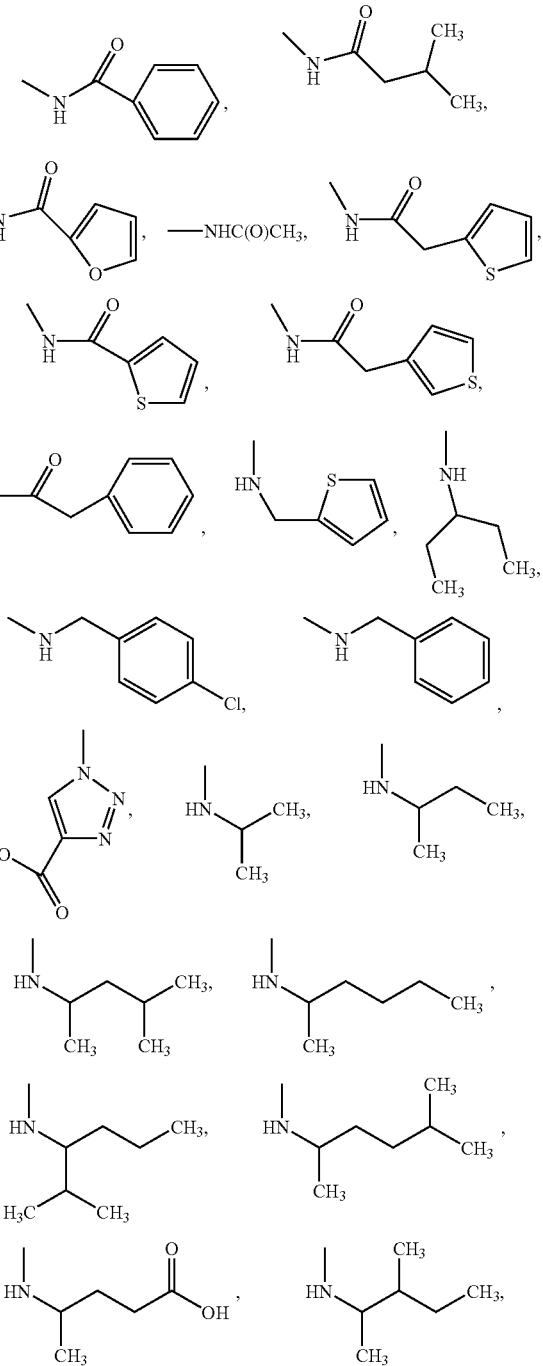

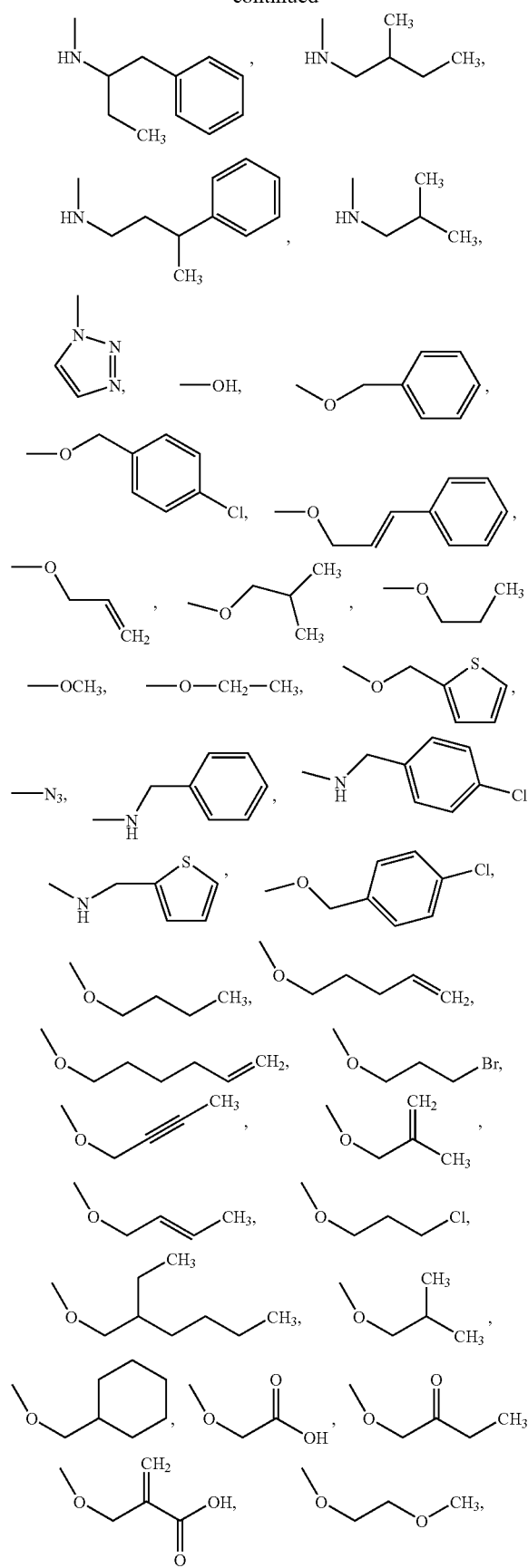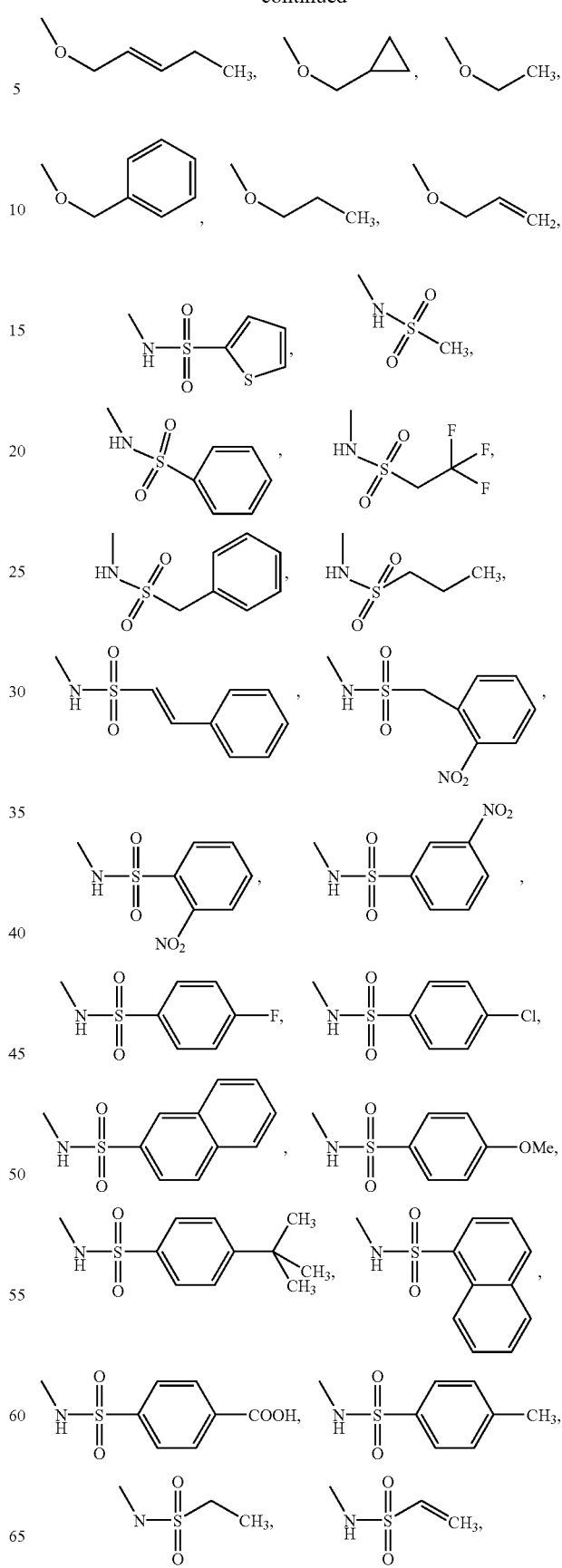

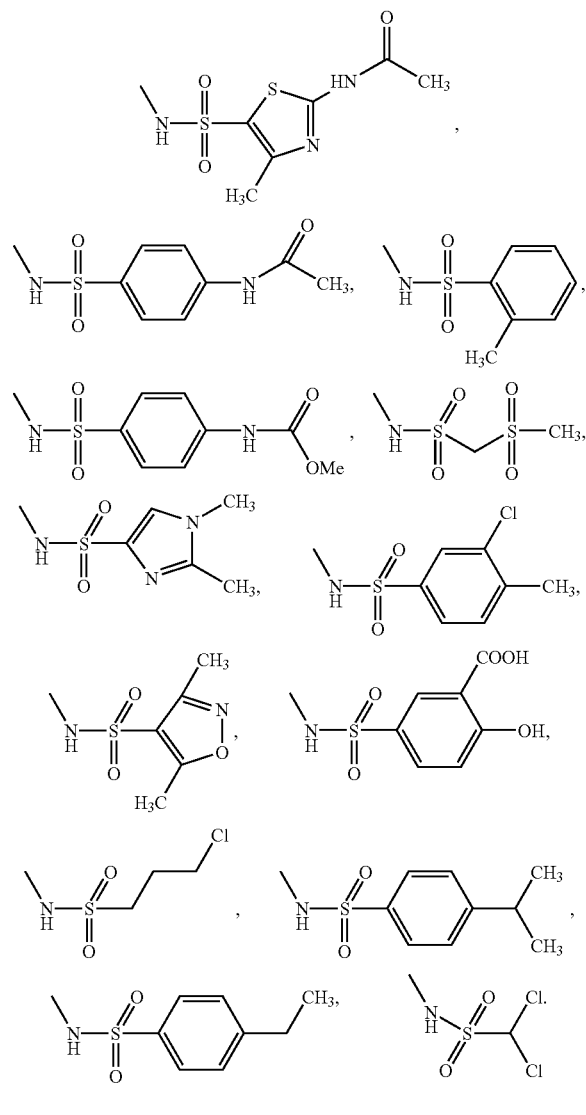
Wherein R₂ is selected from the group consisting of:
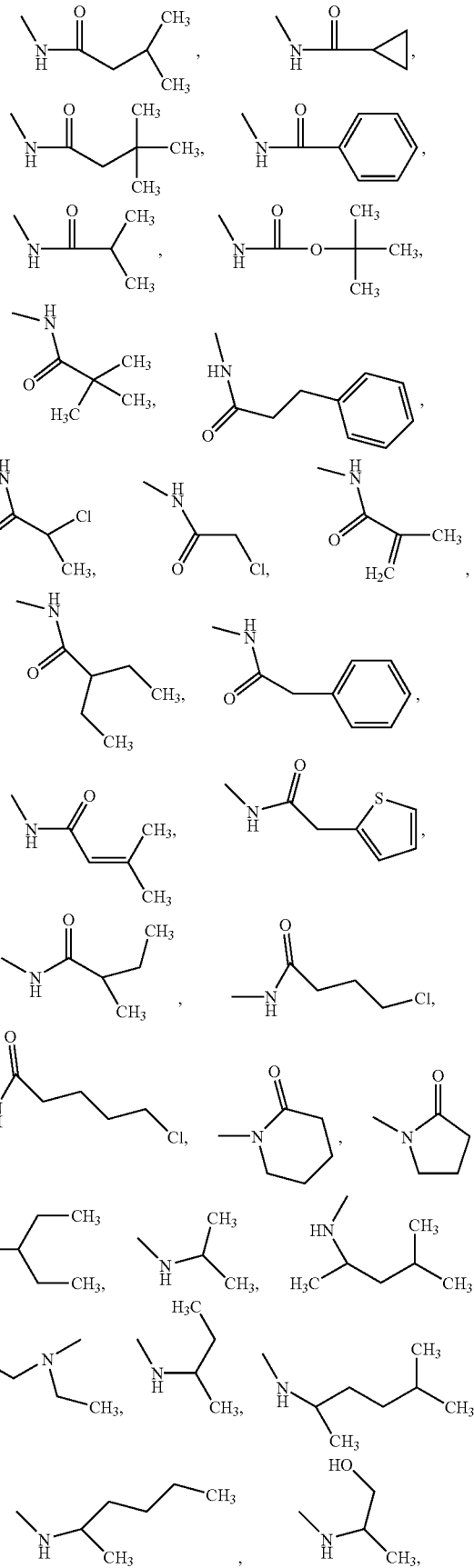
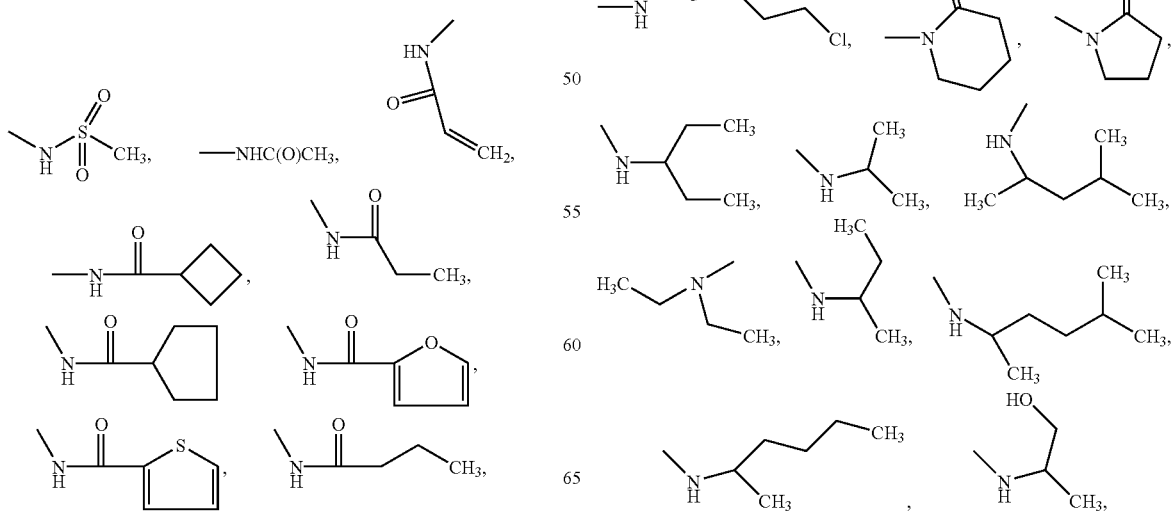

-continued

[Chemical structures: various N-methyl amines including N-methyl-1-phenylpropan-2-amine; N-methyl isobutyl amine; N-methyl neopentyl-type amine; N-methyl isopentyl amine; N-methyl sec-butyl type amine; N-methyl isopropyl branched amine; N-methylpyrrolidine; N-methyl tert-butyl-methyl amine]

11. A method according to claim 7 or 8 represented by the formulae:

[Chemical structure: dihydropyran with AcHN, N₃, CO₂H and C(O)R₁ substituents]

wherein R₁ is selected from the group consisting of:

[Chemical structures: N-methyl-butyl-methyl amine; N-methylbenzylamine; N-methyl isopropyl amine variants]

NHCH₃, N(CH₃)₂.

12. A method according to claim 7 or 8 represented by the formulae:

[Chemical structure: dihydropyran with OH, OH, OH, R₂, R₁ substituents and COOH]

Wherein R₁ is selected from the group consisting of:

[Chemical structures: N-methyl methanesulfonamide; N-methyl benzenesulfonamide]

[Chemical structures: N-methyl phenylmethanesulfonamide; N-methyl thiophene-2-sulfonamide]

Wherein R₂ is: —NHC(O)CH₃.

13. A compound represented by one of the formulas:

[Chemical structure A: six-membered ring with X, R₁, R₁ₐ, R₂, R₂ₐ, R₃, R₃ₐ, R₄, R₄ₐ, R₅, R₅ₐ]

[Chemical structure B: six-membered ring with one double bond, X, R₁, R₂, R₃, R₃ₐ, R₄, R₄ₐ, R₅, R₅ₐ]

[Chemical structure C: six-membered ring with one double bond, X₁, R₁, R₂, R₂ₐ, R₃, R₃ₐ, R₄, R₄ₐ, R₅, R₅ₐ]

wherein X is selected from the group consisting of:
CHR, O, NR, N—OR, NR(O), S, S(O) and S(O)O,
X₁ is selected from the group consisting of CR, N, and N(O);
R is selected from the group consisting of:
H, alkyl, alkene, alkyne, CN, NO₂, N₃, halo and NHR₁₀;
R₁ is selected from the group consisting of:
H, $(CH_2)nCO_2R_{10}$, $(CH_2)$n-tetrazol, $(CH_2)nSO_3H$, $(CH_2)nSO_2H$, $(CH_2)nPO_3H_2$, $(CH_2)nCONR_{10}R_{10a}$, $(CH_2)nNO_2$, and $(CH_2)nCHO$;
R₁ₐ is selected from the group consisting of:
H, $(CH_2)nOR_{10}$, $(CH_2)nCN$, $(CH_2)nNR_{10}R_{10a}$, $(CH_2)nNHC(O)R_{10}$, $(CH_2)nC(O)NR_{10}R_{10a}$, and $(CH_2)nOC(O)R_{10}$;
R₁ and R₁ₐ both cannot be H
each of R₂ and R₂ₐ is independently selected from the group consisting of H, halo, CN, $(CH_2)nCO_2R_{10}$, $(CH_2)nNR_{10}R_{10a}$ and $(CH_2)_n$—OR₁₀;
each of R₃ and R₃ₐ is independently selected from the group consisting of:
H, NHSO₂R₁₀, N(O)—SO₂R₁₀, NR₁₀SO₂R₁₀ₐ, $(CH_2)mYR_{10}$, and $(CH_2)mR_6$; provided that when R₃ or R₃ₐ is $(CH_2)_mYR_{10}$ or $(CH_2)_mR_6$ then m is at least 1 for R₃ or R₃ₐ;
at least one of R₃ and R₃ₐ should be other than H
Y is selected from the group consisting of:
O, NH, NHC(O), C(O)NH, S, S(O), S(O)O, NHS(O)O, S(O)ONH, NHC(O)NH and heterocycle;
R₃ and R₃ₐ together may be
=O, =CHR₆, =CHR₁₀, =NR₁₀, and =N—OR₁₀

$R_4$ is $(CH_2)mYR_{10}$, $R_{4a}$ is selected from the group consisting of:

H, $(CH_2)mYR_{10}$, and $(CH_2)mR_6$, and $R_4$ and $R_{4a}$ together may be:

=O, =CHR$_6$, =CHR$_{10}$, =NR$_{10}$ and =N—OR$_{10}$ each of $R_5$ and $R_{5a}$ is independently selected from the group consisting of $C(R_7)(R_{7a})H$, $C(R_7)(R_{7a})C(R_8)(R_{8a})H$, $C(R_7)(R_{7a})C(R_8)(R_{8a})C(R_9)(R_{9a})H$, $OC(R_7)(R_{7a})H$, $OC(R_7)(R_{7a})C(R_8)(R_{8a})H$, $C(R_7)(R_{7a})OC(R_8)(R_{8a})H$, $N(R_{10})C(R_7)(R_{7a})H$, $N(R_{10})C(R_7)(R_{7a})C(R_8)(R_{8a})H$, $C(R_7)(R_{7a})N(R_{10})C(R_8)(R_{8a})H$, and $C(O)NR_{10}R_{10a}$;

$R_6$ is selected from the group consisting of
H, halo, CN, $NO_2$, $N_3$, $CO_2R_{10}$, $R_{10}$ and $NR_{10}R_{10a}$;

$R_7$, $R_8$, $R_{8a}$, $R_9$ and $R_{9a}$ is selected from the group consisting of:

H, $(CH_2)mYR_{10}$ and $(CH_2)mR_6$ $R_{7a}$ is $(CH_2)mYR_{10}$ each of the $R_{10}$ and $R_{10a}$ is individually selected from the groups consisting of:

H, alkyl, substituted alkyl, aryl, substituted aryl, arylalkyl, substituted arylalkyl, heterocycle, substituted heterocycle, alkenyl, substituted alkenyl, alkynyl, and substituted alkynyl;

Each of m and n is individually 0, 1, 2, 3, or 4;

and pharmaceutically acceptable salt thereof; and pro-drugs thereof.

14. The compound of claim 1 wherein X=O, $R_1$=$CO_2H$, $R_{1a}$=$R_2$=$R_{2a}$=$R_{3a}$=$R_{4a}$=$R_{5a}$=H, $R_3$=$NHSO_2CHCl_2$, $R_4$=NH—$C(O)CH(CH_3)_2$ and $R_5$=$CH(OH)CH(OH)CH_2OH$.

* * * * *